US008551485B2

(12) United States Patent
Bernett et al.

(10) Patent No.: US 8,551,485 B2
(45) Date of Patent: Oct. 8, 2013

(54) ANTI-CD40 ANTIBODIES AND METHODS OF INHIBITING PROLIFERATION OF CD40 EXPRESSING CELLS

(75) Inventors: Matthew J. Bernett, Monrovia, CA (US); Seung Yup Chu, Cypress, CA (US); John R. Desjarlais, Pasadena, CA (US); Sher Bahadur Karki, Pomona, CA (US); Gregory Alan Lazar, Arcadia, CA (US); Erik WeiKing Pong, Temple City, CA (US); Eugene Alexander Zhukovsky, Bethel, CT (US)

(73) Assignee: Xencor, Inc., Monrovia, CA (US)

( * ) Notice: Subject to any disclaimer, the term of this patent is extended or adjusted under 35 U.S.C. 154(b) by 228 days.

(21) Appl. No.: 12/864,075

(22) PCT Filed: Jan. 21, 2009

(86) PCT No.: PCT/US2009/031585
§ 371 (c)(1),
(2), (4) Date: Oct. 6, 2010

(87) PCT Pub. No.: WO2009/094391
PCT Pub. Date: Jul. 30, 2009

(65) Prior Publication Data
US 2011/0027276 A1 Feb. 3, 2011

Related U.S. Application Data

(60) Provisional application No. 61/062,172, filed on Jan. 23, 2008.

(51) Int. Cl.
*A61K 39/395* (2006.01)
*C07K 16/28* (2006.01)
(52) U.S. Cl.
USPC ........... 424/153.1; 424/130.1; 424/133.1; 424/141.1; 424/143.1; 424/144.1; 424/154.1; 424/173.1; 530/387.1; 530/387.3; 530/388.1; 530/388.2; 530/388.22; 530/388.7; 530/388.73
(58) Field of Classification Search
None
See application file for complete search history.

(56) References Cited

U.S. PATENT DOCUMENTS

| 5,874,082 | A | 2/1999 | de Boer | |
|---|---|---|---|---|
| 7,557,190 | B2 * | 7/2009 | Barbosa et al. | 530/387.1 |
| 2006/0003412 | A1 * | 1/2006 | Chamberlain et al. | 435/69.1 |
| 2006/0115479 | A1 * | 6/2006 | Reinscheid et al. | 424/146.1 |
| 2007/0224192 | A1 * | 9/2007 | Lazar et al. | 424/133.1 |
| 2008/0091954 | A1 | 4/2008 | Morris et al. | |
| 2008/0187966 | A1 * | 8/2008 | Simmons | 435/69.3 |

FOREIGN PATENT DOCUMENTS

| EP | 1 707 627 | 10/2006 |
|---|---|---|
| WO | WO 00/75348 | 12/2000 |
| WO | WO 02/28481 | 4/2002 |
| WO | WO 03/029296 | 4/2003 |
| WO | WO 03/074679 | * 9/2003 |
| WO | WO 2006/019447 | 2/2006 |
| WO | WO 2006/047350 | 5/2006 |
| WO | WO 2006/073443 | 7/2006 |
| WO | WO 2007/075326 | 7/2007 |
| WO | WO 2008/091954 | 7/2008 |

OTHER PUBLICATIONS

Vajdos et al., J. Mol. Biol. 320: 415-428, 2002.*
Amit et al., Science 233:747-753, 1986.*
International Search Report dated Apr. 14, 2009, PCT/US2009/031585, 7 pages.
Francisco et al., "Construction, Expression, and Characterization of BD1-G28-5 sFv, a Single Chain anti-CD40 Immunotoxin Containing the Ribosome-inactivating Protein Bryodin 1," *Journal of Biological Chemistry*, American Society of Biolochemical Biologists, Birmingham US, vol. 272, No. 39, Sep. 26, 1997, pp. 24165-24169, XP002081655, ISSN: 0021-9258.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *Journal of Biological Chemistry*, American Society of Biolochemical Biologists, Birmingham US, vol. 278, No. 5, Jan. 31, 2003, pp. 3466-3473, XP002965857, ISSN: 0021-9258.

* cited by examiner

*Primary Examiner* — Phillip Gambel
(74) *Attorney, Agent, or Firm* — Dorsey and Whitney LLP

(57) ABSTRACT

The present invention describes humanized antibodies that target CD40, wherein the antibodies comprise at least one modification relative to a parent antibody, wherein the modification alters affinity to an FcγR or alters effector function as compared to the parent antibody. Also disclosed are methods of using the antibodies of the invention.

27 Claims, 26 Drawing Sheets

Figure 1

> Kappa constant light chain (Cκ) (SEQ ID NO:1)

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

> IgG1 constant heavy chain (CH) (SEQ ID NO:2)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

> IgG2 constant heavy chain (CH) (SEQ ID NO:3)

ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

> IgG3 constant heavy chain (CH) (SEQ ID NO:4)

ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRVELKTPLGDTTHTCPRCPEPKSCD
TPPPCPRCPEPKSCDTPPPCPRCPEPKSCDTPPPCPRCPAPELLGGPSVFLFPPKPKDTL
MISRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVKGF
YPSDIAVEWESSGQPENNYNTTPPMLDSDGSFFLYSKLTVDKSRWQQGNIFSCSVMHEAL
HNRFTQKSLSLSPGK

> IgG4 constant heavy chain (CH) (SEQ ID NO:5)

ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPSCPAPEFLGGPSVFL
FPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVF
SCSVMHEALHNHYTQKSLSLSLGK

Figure 1b

> Hybrid constant heavy chain (CH) (SEQ ID NO:6)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVQFNWYVDGVEVHNAKTKPREEQFNSTF
RVVSVLTVVHQDWLNGKEYKCKVSNKALPAPIEKTISKTKGQPREPQVYTLPPSREEMTKN
QVSLTCLVKGFYPSDIAVEWESNGQPENNYKTTPPMLDSDGSFFLYSKLTVDKSRWQQGN
VFSCSVMHEALHNHYTQKSLSLSPGK

> Hybrid constant heavy chain (CH) with 239D and 332E substitutions (SEQ ID NO:7)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPD
VFLFPPKPKDTLMISRTPEVTCVVVDVSHEDPEVQFNWYVDGVEVHNAKTKPREEQFNSTF
RVVSVLTVVHQDWLNGKEYKCKVSNKALPAPEEKTISKTKGQPREPQVYTLPPSREEMTK
NQVSLTCLVKGFYPSDIAVEWESNGQPENNYKTTPPMLDSDGSFFLYSKLTVDKSRWQQG
NVFSCSVMHEALHNHYTQKSLSLSPGK

Figure 1c

| CH1 EU Index | 118 | 119 | 120 | 121 | 122 | 123 | 124 | 125 | 126 | 127 | 128 | 129 | 130 |
|---|---|---|---|---|---|---|---|---|---|---|---|---|---|
| IgG1 | A | S | T | K | G | P | S | V | F | P | L | A | P |
| IgG2 | A | S | T | K | G | P | S | V | F | P | L | A | P |
| IgG3 | A | S | T | K | G | P | S | V | F | P | L | A | P |
| IgG4 | A | S | T | K | G | P | S | V | F | P | L | A | P |

| EU Index | 131 | 132 | 133 | 134 | 135 | 136 | 137 | 138 | 139 | 140 | 141 | 142 | 143 |
|---|---|---|---|---|---|---|---|---|---|---|---|---|---|
| IgG1 | S | S | K | S | T | S | G | G | T | A | A | L | G |
| IgG2 | C | S | R | S | T | S | E | S | T | A | A | L | G |
| IgG3 | C | S | R | S | T | S | G | G | T | A | A | L | G |
| IgG4 | C | S | R | S | T | S | E | S | T | A | A | L | G |

| EU Index | 144 | 145 | 146 | 147 | 148 | 149 | 150 | 151 | 152 | 153 | 154 | 155 | 156 |
|---|---|---|---|---|---|---|---|---|---|---|---|---|---|
| IgG1 | C | L | V | K | D | Y | F | P | E | P | V | T | V |
| IgG2 | C | L | V | K | D | Y | F | P | E | P | V | T | V |
| IgG3 | C | L | V | K | D | Y | F | P | E | P | V | T | V |
| IgG4 | C | L | V | K | D | Y | F | P | E | P | V | T | V |

| EU Index | 157 | 158 | 159 | 160 | 161 | 162 | 163 | 164 | 165 | 166 | 167 | 168 | 169 |
|---|---|---|---|---|---|---|---|---|---|---|---|---|---|
| IgG1 | S | W | N | S | G | A | L | T | S | G | V | H | T |
| IgG2 | S | W | N | S | G | A | L | T | S | G | V | H | T |
| IgG3 | S | W | N | S | G | A | L | T | S | G | V | H | T |
| IgG4 | S | W | N | S | G | A | L | T | S | G | V | H | T |

| EU Index | 170 | 171 | 172 | 173 | 174 | 175 | 176 | 177 | 178 | 179 | 180 | 181 | 182 |
|---|---|---|---|---|---|---|---|---|---|---|---|---|---|
| IgG1 | F | P | A | V | L | Q | S | S | G | L | Y | S | L |
| IgG2 | F | P | A | V | L | Q | S | S | G | L | Y | S | L |
| IgG3 | F | P | A | V | L | Q | S | S | G | L | Y | S | L |
| IgG4 | F | P | A | V | L | Q | S | S | G | L | Y | S | L |

| EU Index | 183 | 184 | 185 | 186 | 187 | 188 | 189 | 190 | 191 | 192 | 193 | 194 | 195 |
|---|---|---|---|---|---|---|---|---|---|---|---|---|---|
| IgG1 | S | S | V | V | T | V | P | S | S | S | L | G | T |
| IgG2 | S | S | V | V | T | V | P | S | S | N | F | G | T |
| IgG3 | S | S | V | V | T | V | P | S | S | S | L | G | T |
| IgG4 | S | S | V | V | T | V | P | S | S | S | L | G | T |

Figure 1c (continued)

| EU Index | 196 | 197 | 198 | 199 | 200 | 201 | 202 | 203 | 204 | 205 | 206 | 207 | 208 |
|---|---|---|---|---|---|---|---|---|---|---|---|---|---|
| IgG1 | Q | T | Y | - | C | N | V | N | H | K | P | S | N |
| IgG2 | Q | T | Y | T | C | N | V | D | H | K | P | S | N |
| IgG3 | Q | T | Y | T | C | N | V | N | H | K | P | S | N |
| IgG4 | K | T | Y | T | C | N | V | D | H | K | P | S | N |

| EU Index | 209 | 210 | 211 | 212 | 213 | 214 | 215 | 216 | 217 | 218 | 219 | 220 |
|---|---|---|---|---|---|---|---|---|---|---|---|---|
| IgG1 | T | K | V | D | K | K | V | E | P | K | S | C |
| IgG2 | T | K | V | D | K | T | V | E | R | K | C | C |
| IgG3 | T | K | V | D | K | R | V | E | L | K | T | P |
| IgG4 | T | K | V | D | K | R | V | E | S | K | Y | G |

Hinge

| EU Index | 221 | 222 | 223 | 224 | 225 |
|---|---|---|---|---|---|
| IgG1 | D | K | T | H | T |
| IgG2 | - | V | - | E | - |
| IgG3 | L | T | T | H | T |
| IgG4 | - | - | - | P | P |

Fc

| EU Index | 226 | 227 | 228 |
|---|---|---|---|
| IgG1 | C | P | P |
| IgG2 | C | P | P |
| IgG3 | C | P | P |
| IgG4 | C | P | P |

| EU Index | | | | | | | | | | | |
|---|---|---|---|---|---|---|---|---|---|---|---|
| IgG1 | S | C | D | P | P | C | P | A | P | E | L |
| IgG2 | | | | | | | | | | | |
| IgG3 | | | T | | | R | | | | | |
| IgG4 | | | | | | | | | | | |

| EU Index | | | | | | | | | | | |
|---|---|---|---|---|---|---|---|---|---|---|---|
| IgG1 | P | E | K | S | C | D | T | P | P | P | C |
| IgG2 | | | | | | | | | | | |
| IgG3 | | | | | | | | | | P | R |
| IgG4 | | | | | | | | | | | |

| EU Index | 229 | 230 | 231 | 232 | 233 | 234 | 235 | 236 |
|---|---|---|---|---|---|---|---|---|
| IgG1 | C | P | A | P | E | L | L | G |
| IgG2 | C | P | P | P | P | V | A | - |
| IgG3 | C | P | A | P | E | L | L | G |
| IgG4 | C | P | P | P | E | F | L | G |

| EU Index | | | |
|---|---|---|---|
| IgG3 | C | P | R |

Figure 1c (continued)

| CH2 EU Index | 237 | 238 | 239 | 240 | 241 | 242 | 243 | 244 | 245 | 246 | 247 | 248 | 249 | | | |
|---|---|---|---|---|---|---|---|---|---|---|---|---|---|---|---|---|
| IgG1 | G | P | S | V | F | L | F | P | P | K | P | K | D | | | |
| IgG2 | G | P | S | V | F | L | F | P | P | K | P | K | D | | | |
| IgG3 | G | P | S | V | F | L | F | P | P | K | P | K | D | | | |
| IgG4 | G | P | S | V | F | L | F | P | P | K | P | K | D | | | |

| EU Index | 250 | 251 | 252 | 253 | 254 | 255 | 256 | 257 | 258 | 259 | 260 | 261 | 262 | 263 |
|---|---|---|---|---|---|---|---|---|---|---|---|---|---|---|
| IgG1 | T | L | M | I | S | R | T | P | E | V | T | C | V | V |
| IgG2 | T | L | M | I | S | R | T | P | E | V | T | C | V | V |
| IgG3 | T | L | M | I | S | R | T | P | E | V | T | C | V | V |
| IgG4 | T | L | M | I | S | R | T | P | E | V | T | C | V | V |

| EU Index | 264 | 265 | 266 | 267 | 268 | 269 | 270 | 271 | 272 | 273 | 274 | 275 | 276 |
|---|---|---|---|---|---|---|---|---|---|---|---|---|---|
| IgG1 | V | D | V | S | H | E | D | P | E | V | K | F | N |
| IgG2 | V | D | V | S | H | E | D | P | E | V | Q | F | N |
| IgG3 | V | D | V | S | H | E | D | P | E | V | Q | F | K |
| IgG4 | V | D | V | S | Q | E | D | P | E | V | Q | F | N |

| EU Index | 277 | 278 | 279 | 280 | 281 | 282 | 283 | 284 | 285 | 286 | 287 | 288 | 289 | 290 |
|---|---|---|---|---|---|---|---|---|---|---|---|---|---|---|
| IgG1 | W | Y | V | D | G | V | E | V | H | N | A | K | T | K |
| IgG2 | W | Y | V | D | G | V | E | V | H | N | A | K | T | K |
| IgG3 | W | Y | V | D | G | V | E | V | H | N | A | K | T | K |
| IgG4 | W | Y | V | D | G | V | E | V | H | N | A | K | T | K |

| EU Index | 291 | 292 | 293 | 294 | 295 | 296 | 297 | 298 | 299 | 300 | 301 | 302 | 303 |
|---|---|---|---|---|---|---|---|---|---|---|---|---|---|
| IgG1 | P | R | E | E | Q | Y | N | S | T | Y | R | V | V |
| IgG2 | P | R | E | E | Q | F | N | S | T | F | R | V | V |
| IgG3 | P | R | E | E | Q | Y | N | S | T | F | R | V | V |
| IgG4 | P | R | E | E | Q | F | N | S | T | Y | R | V | V |

| EU Index | 304 | 305 | 306 | 307 | 308 | 309 | 310 | 311 | 312 | 313 | 314 | 315 | 316 | 317 |
|---|---|---|---|---|---|---|---|---|---|---|---|---|---|---|
| IgG1 | S | V | L | T | V | L | H | Q | D | W | L | N | G | K |
| IgG2 | S | V | L | T | V | V | H | Q | D | W | L | N | G | K |
| IgG3 | S | V | L | T | V | L | H | Q | D | W | L | N | G | K |
| IgG4 | S | V | L | T | V | L | H | Q | D | W | L | N | G | K |

Figure 1c (continued)

| EU Index | 318 | 319 | 320 | 321 | 322 | 323 | 324 | 325 | 326 | 327 | 328 | 329 | 330 |
|---|---|---|---|---|---|---|---|---|---|---|---|---|---|
| IgG1 | E | Y | K | C | K | V | S | N | K | A | L | P | A |
| IgG2 | E | Y | K | C | K | V | S | N | K | G | L | P | A |
| IgG3 | E | Y | K | C | K | V | S | N | K | A | L | P | A |
| IgG4 | E | Y | K | C | K | V | S | N | K | G | L | P | S |

| EU Index | 331 | 332 | 333 | 334 | 335 | 336 | 337 | 338 | 339 | 340 |
|---|---|---|---|---|---|---|---|---|---|---|
| IgG1 | P | I | E | K | T | I | S | K | A | K |
| IgG2 | P | I | E | K | T | I | S | K | T | K |
| IgG3 | P | I | E | K | T | I | S | K | T | K |
| IgG4 | S | I | E | K | T | I | S | K | A | K |

CH3

| EU Index | 341 | 342 | 343 | 344 | 345 | 346 | 347 | 348 | 349 | 350 | 351 | 352 | 353 |
|---|---|---|---|---|---|---|---|---|---|---|---|---|---|
| IgG1 | G | Q | P | R | E | P | Q | V | Y | T | L | P | P |
| IgG2 | G | Q | P | R | E | P | Q | V | Y | T | L | P | P |
| IgG3 | G | Q | P | R | E | P | Q | V | Y | T | L | P | P |
| IgG4 | G | Q | P | R | E | P | Q | V | Y | T | L | P | P |

| EU Index | 354 | 355 | 356 | 357 | 358 | 359 | 360 | 361 | 362 | 363 | 364 | 365 | 366 | 367 |
|---|---|---|---|---|---|---|---|---|---|---|---|---|---|---|
| IgG1 | S | R | D | E | L | T | K | N | Q | V | S | L | T | C |
| IgG2 | S | R | E | E | M | T | K | N | Q | V | S | L | T | C |
| IgG3 | S | R | E | E | M | T | K | N | Q | V | S | L | T | C |
| IgG4 | S | Q | E | E | M | T | K | N | Q | V | S | L | T | C |

| EU Index | 368 | 369 | 370 | 371 | 372 | 373 | 374 | 375 | 376 | 377 | 378 | 379 | 380 |
|---|---|---|---|---|---|---|---|---|---|---|---|---|---|
| IgG1 | L | V | K | G | F | Y | P | S | D | – | A | V | E |
| IgG2 | L | V | K | G | F | Y | P | S | D | – | A | V | E |
| IgG3 | L | V | K | G | F | Y | P | S | D | – | A | V | E |
| IgG4 | L | V | K | G | F | Y | P | S | D | – | A | V | E |

| EU Index | 381 | 382 | 383 | 384 | 385 | 386 | 387 | 388 | 389 | 390 | 391 | 392 | 393 | 394 |
|---|---|---|---|---|---|---|---|---|---|---|---|---|---|---|
| IgG1 | W | E | S | N | G | Q | P | E | N | N | Y | K | T | T |
| IgG2 | W | E | S | N | G | Q | P | E | N | N | Y | K | T | T |
| IgG3 | W | E | S | S | G | Q | P | E | N | N | Y | N | T | T |
| IgG4 | W | E | S | N | G | Q | P | E | N | N | Y | K | T | T |

Figure 1c (continued)

| EU Index | 395 | 396 | 397 | 398 | 399 | 400 | 401 | 402 | 403 | 404 | 405 | 406 | 407 |
|---|---|---|---|---|---|---|---|---|---|---|---|---|---|
| IgG1 | P | P | V | L | D | S | D | G | S | F | F | L | Y |
| IgG2 | P | P | M | L | D | S | D | G | S | F | F | L | Y |
| IgG3 | P | P | M | L | D | S | D | G | S | F | F | L | Y |
| IgG4 | P | P | V | L | D | S | D | G | S | F | F | L | Y |

| EU Index | 408 | 409 | 410 | 411 | 412 | 413 | 414 | 415 | 416 | 417 | 418 | 419 | 420 | 421 |
|---|---|---|---|---|---|---|---|---|---|---|---|---|---|---|
| IgG1 | S | K | L | T | V | D | K | S | R | W | Q | Q | G | N |
| IgG2 | S | K | L | T | V | D | K | S | R | W | Q | Q | G | N |
| IgG3 | S | K | L | T | V | D | K | S | R | W | Q | Q | G | N |
| IgG4 | S | R | L | T | V | D | K | S | R | W | Q | E | G | N |

| EU Index | 422 | 423 | 424 | 425 | 426 | 427 | 428 | 429 | 430 | 431 | 432 | 433 | 434 |
|---|---|---|---|---|---|---|---|---|---|---|---|---|---|
| IgG1 | V | F | S | C | S | V | M | H | E | A | L | H | N |
| IgG2 | V | F | S | C | S | V | M | H | E | A | L | H | N |
| IgG3 | I | F | S | C | S | V | M | H | E | A | L | H | N |
| IgG4 | V | F | S | C | S | V | M | H | E | A | L | H | N |

| EU Index | 435 | 436 | 437 | 438 | 439 | 440 | 441 | 442 | 443 | 444 | 445 | 446 | 447 |
|---|---|---|---|---|---|---|---|---|---|---|---|---|---|
| IgG1 | H | Y | T | Q | K | S | L | S | L | S | P | G | K |
| IgG2 | H | Y | T | Q | K | S | L | S | L | S | P | G | K |
| IgG3 | R | F | T | Q | K | S | L | S | L | S | P | G | K |
| IgG4 | H | Y | T | Q | K | S | L | S | L | S | L | G | K |

Figure 2a

| Allotype | Allotype | Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |

Figure 2b

| Allotype | Allotype | Position |
|---|---|---|
| | | 282 |
| G2m(23) | G2m(n+) | V |
| | G2m(n-) | M |

Figure 3

| Receptor binding improvement | Receptor binding reduction | Cell activity | Therapeutic activity |
|---|---|---|---|
| Solely I | - | Enhance dendritic cell activity and uptake, and subsequent presentation of antigens; enhance monocyte and macrophage response to antibody | Enhance cell-based immune response against target |
| IIIa | | Enhance ADCC and phagocytosis of broad range of cell types | Increased target cell lysis |
| IIIa | IIb | Enhance ADCC and phagocytosis of broad range of cell types | Increased target cell lysis |
| IIb, IIc | | Reduction of activity of all FcR bearing cell types except NK cells and possible activation of NK cells via IIc receptor signaling | Enhancement of target cell lysis selective for NK cell accessible target cells |
| IIb, IIIa | - | Possible NK cell specific activation and enhancement of NK cell mediated ADCC | Enhancement of target cell lysis selective for NK cell accessible target cells |
| IIIb | | Neutrophil mediated phagocytosis enhancement | Enhanced target cell destruction for neutrophil accessible cells |
| FcαR | | Neutrophil mediated phagocytosis enhancement | Enhanced target cell destruction for neutrophil accessible cells |
| I,IIa,IIIa | IIb | Enhance dendritic cell activity and uptake, and subsequent presentation of antigens to T cells; enhance monocyte and macrophage response to antibody | Enhance cell-based immune response against target |
| IIb | IIIa,IIa,I | Reduction in activity of monocytes, macrophages, neutrophils, NK, dendritic and other gamma receptor bearing cells | Eliminate or reduce cell-mediated cytotoxicity against target bearing cells |

Figure 4

> Human CD40 isoform 1 (SEQ ID NO:8).

MVRLPLQCVLWGCLLTAVHPEPPTACREKQYLINSQCCSLCQPGQKLVSDCTEFTETECLP
CGESEFLDTWNRETHCHQHKYCDPNLGLRVQQKGTSETDTICTCEEGWHCTSEACESCV
LHRSCSPGFGVKQIATGVSDTICEPCPVGFFSNVSSAFEKCHPWTSCETKDLVVQQAGTNK
TDVVCGPQDRLRALVVIPIIFGILFAILLVLVFIKKVAKKPTNKAPHPKQEPQEINFPDDLPGSN
TAAPVQETLHGCQPVTQEDGKESRISVQER

> Human CD40 isoform 2 (SEQ ID NO:9).

MVRLPLQCVLWGCLLTAVHPEPPTACREKQYLINSQCCSLCQPGQKLVSDCTEFTETECLP
CGESEFLDTWNRETHCHQHKYCDPNLGLRVQQKGTSETDTICTCEEGWHCTSEACESCV
LHRSCSPGFGVKQIATGVSDTICEPCPVGFFSNVSSAFEKCHPWTRSPGSAESPGGDPHH
LRDPVCHPLGAGLYQKGGQEANQ

Figure 5a

> WT S2C6 VH (H0) (SEQ ID NO:10)

EVQLQQSGPDLVKPGASVKISCKASGYSFTGYYIHWVKQSHGKSLEWIGRVIPNNGGTSYN
QKFKGKAILTVDKSSSTAYMELRSLTSEDSAVYYCAREGIYWWGHGTTLTVSS

> WT S2C6 VL (L0) (SEQ ID NO:11)

DVVVTQTPLSLPVSLGAQASISCRSSQSLVHSNGNTFLHWYLQKPGQSPKLLIYTVSNRFS
GVPDRFSGSGSGTDFTLKISRVEAEDLGVYFCSQTTHVPWTFGGGTKLEIQ

> WT G28-5 VH (H0) (SEQ ID NO:12)

DIQLQQSGPGLVKPSQSLSLTCSVTGYSITTNYNWNWIRQFPGNKLEWMGYIRYDGTSEYT
PSLKNRVSITRDTSMNQFFLRLTSVTPEDTATYYCARLDYWGQGTSVTVSS

> WT G28-5 VL (L0) (SEQ ID NO:13)

DAVMTQNPLSLPVSLGDEASISCRSSQSLENSNGNTFLNWFFQKPGQSPQLLIYRVSNRFS
GVPDRFSGSGSGTDFTLKISRVEAEDLGVYFCLQVTHVPYTFGGGTTLEIK

> WT 5D12 VH (H0) (SEQ ID NO:14)

QVKLEESGPGLVAPSQSLSITCTVSGFSLSRYSVYWVRQPPGKGLEWLGMMWGGGSTDY
NSALKSRLSISKDTSKSQVFLKMNSLQTDDTAMYYCVRTDGDYWGQGTSVTVSS

> WT 5D12 VL (L0) (SEQ ID NO:15)

ELQLTQSPLSLPVSLGDQASISCRSSQSLVNSNGNTYLHWYLQKPGQSPKLLIYKVSNRFS
GVPDRFSGSGSGTDFTLKISRVEAEDLGVYFCSQSTHVPWTFGGGTKLEIK

Figure 5b

> WT S2C6 VH CDR1 (SEQ ID NO:16)
YSFTGYY
> WT S2C6 VH CDR2 (SEQ ID NO:17)
IPNNGG
>WT S2C6 VH CDR3 (SEQ ID NO:18)
EGIYW
> WT S2C6 VL CDR1 (SEQ ID NO:19)
QSLVHSNGNTF
> WT S2C6 VL CDR2 (SEQ ID NO:20)
TVSNRFS
> WT S2C6 VL CDR3 (SEQ ID NO:21)
TTHVPWT

Figure 5c

> WT G28-5 VH CDR1 (SEQ ID NO:22)
YSITTNYN
> WT G28-5 VH CDR2 (SEQ ID NO:23)
RYDGT
> WT G28-5 VH CDR3 (SEQ ID NO:24)
LDY
> WT G28-5 VL CDR1 (SEQ ID NO:25)
QSLENSNGNTF
> WT G28-5 VL CDR2 (SEQ ID NO:26)
RVSNRFS
> WT G28-5 VL CDR3 (SEQ ID NO:27)
VTHVPYT

Figure 5d

> WT 5D12 VH CDR1 (SEQ ID NO:28)

FSLSRYSVY

> WT 5D12 VH CDR2 (SEQ ID NO:29)

GGS

> WT 5D12 VH CDR3 (SEQ ID NO:30)

TDGDY

> WT 5D12 VL CDR1 (SEQ ID NO:31)

QSLVNSNGNTY

> WT 5D12 VL CDR2 (SEQ ID NO:32)

KVSNRFS

> WT 5D12 VL CDR3 (SEQ ID NO:33)

STHVPWT

Figure 6a
- ● S2C6 Hybrid S239D/I332E (anti-CD40)
- ▲ S2C6 IgG1 (anti-CD40)
- ■ rituximab Hybrid S239D/I332E (anti-CD20)
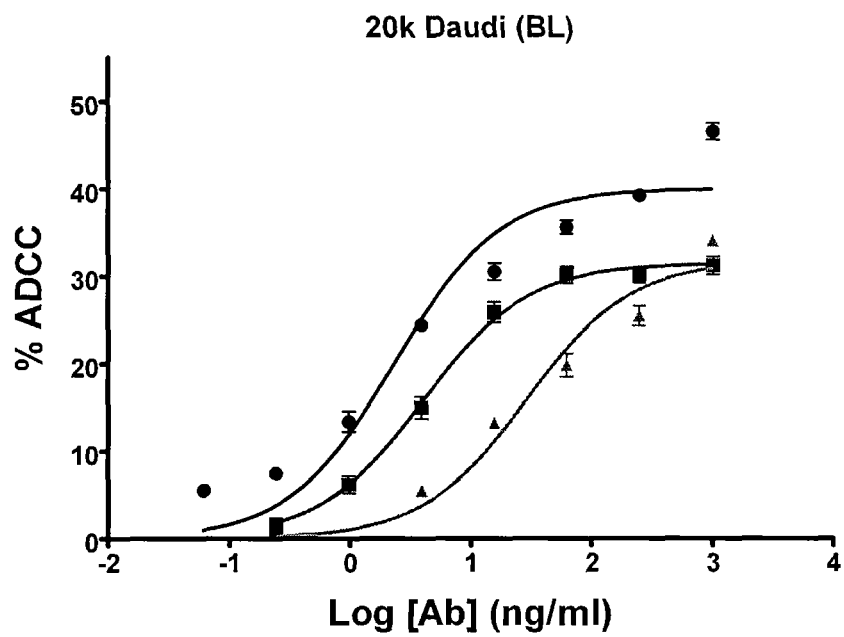
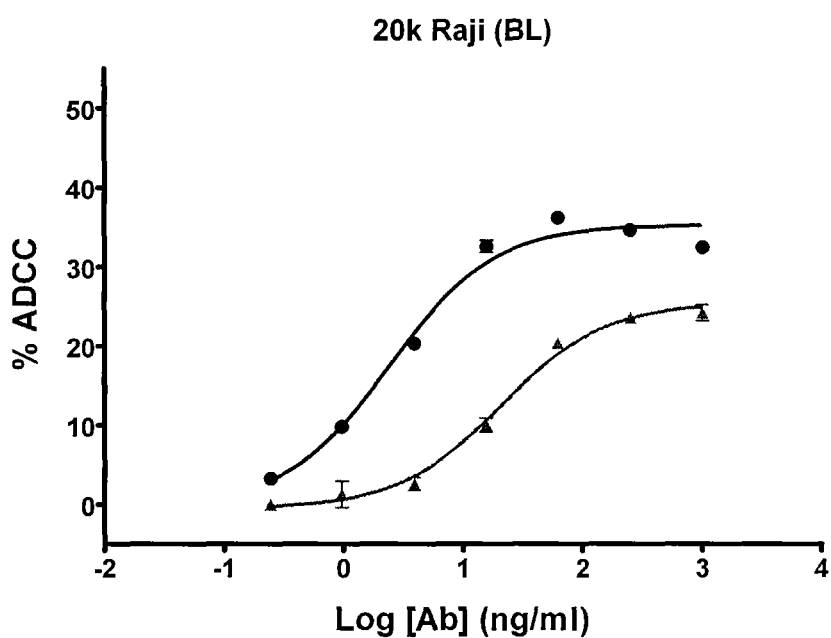

Figure 6a - continued
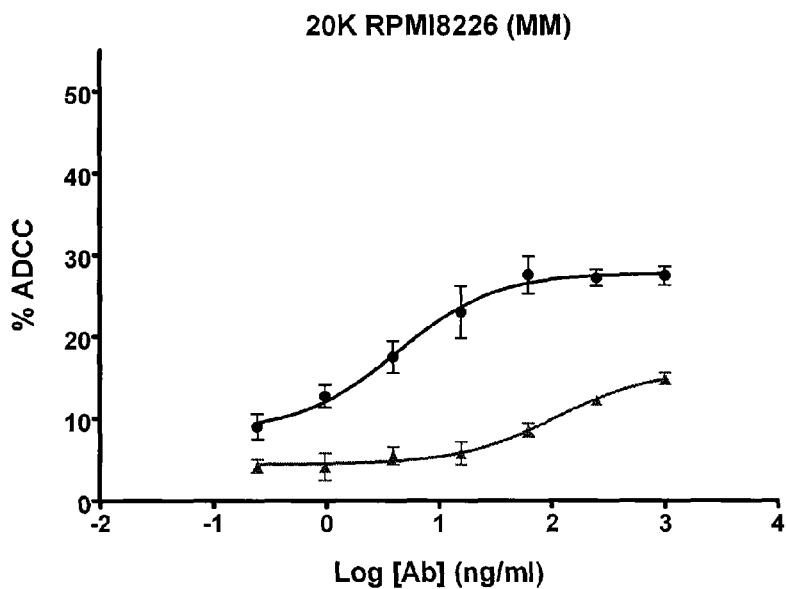
20K RPMI8226 (MM)
Figure 6b
● 5D12 Hybrid S239D/I332 (anti-CD40)
▲ 5D12 IgG1 (anti-CD40)
■ rituximab Hybrid S239D/I332E (anti-CD20)
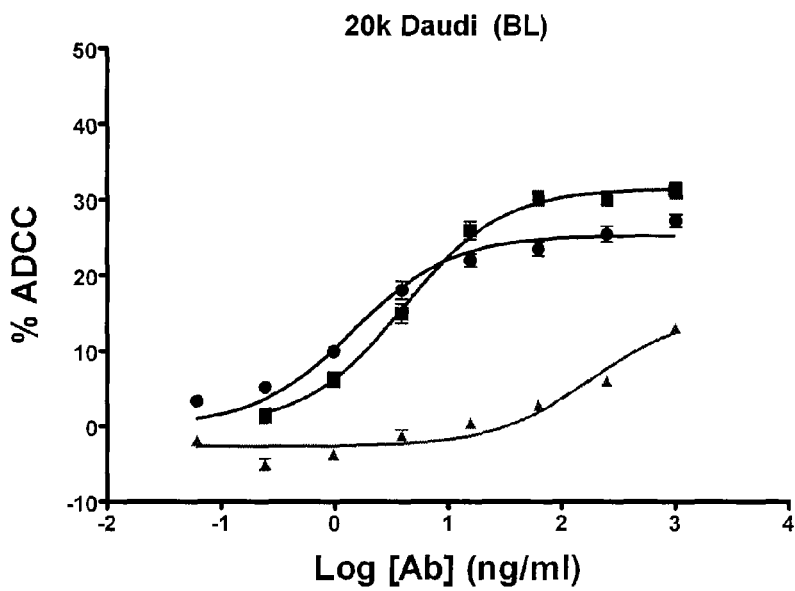
20k Daudi (BL)

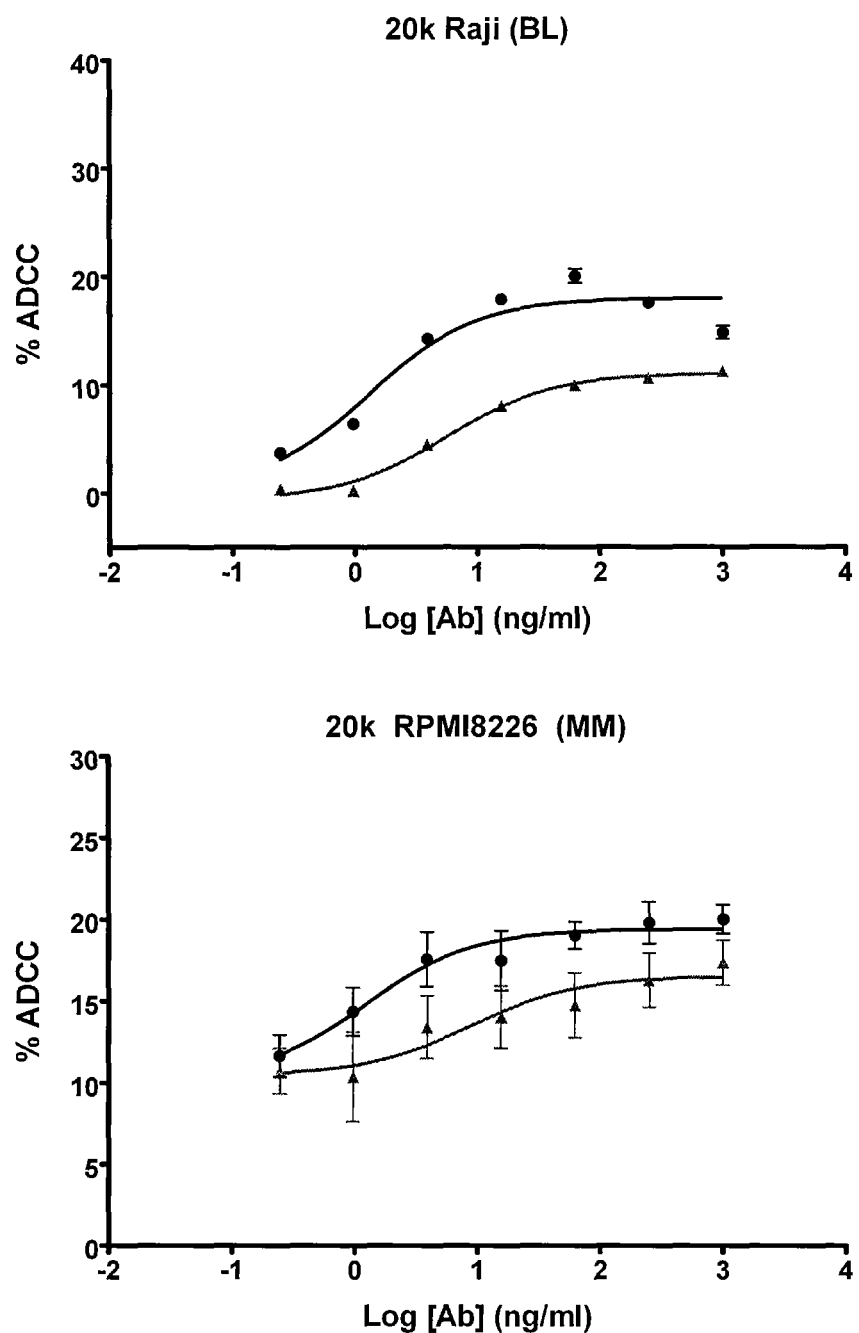
Figure 6b - Continued

Figure 6c
- ● G28-5 Hybrid S239D/I332E (anti-CD40)
- ▲ G28-5 IgG1 (anti-CD40)
- ■ rituximab Hybrid S239D/I332E (anti-CD20)
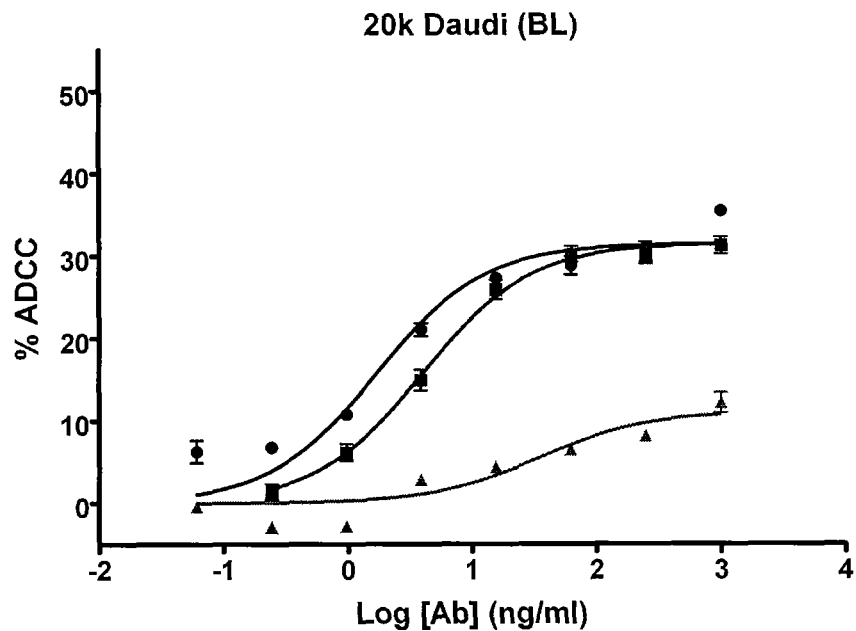
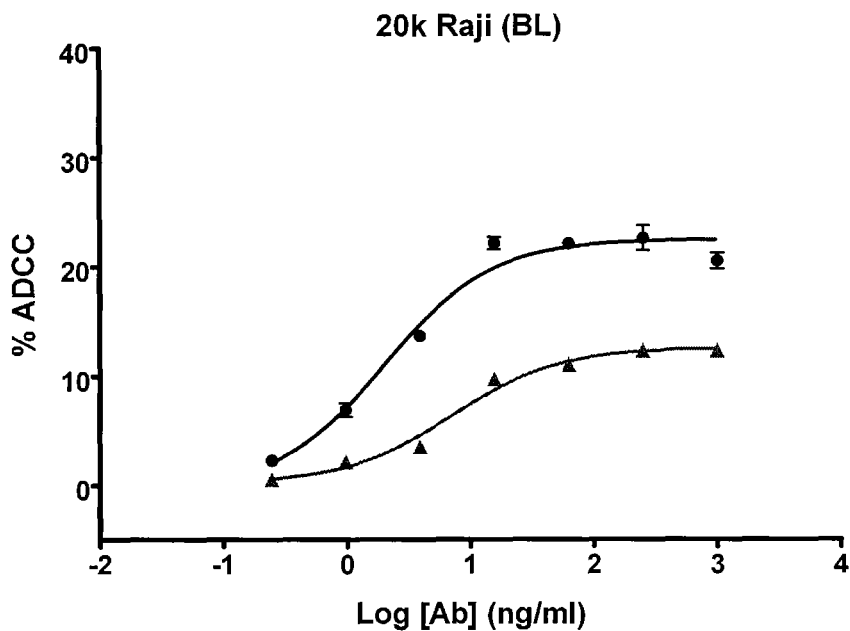

Figure 6c - Continued
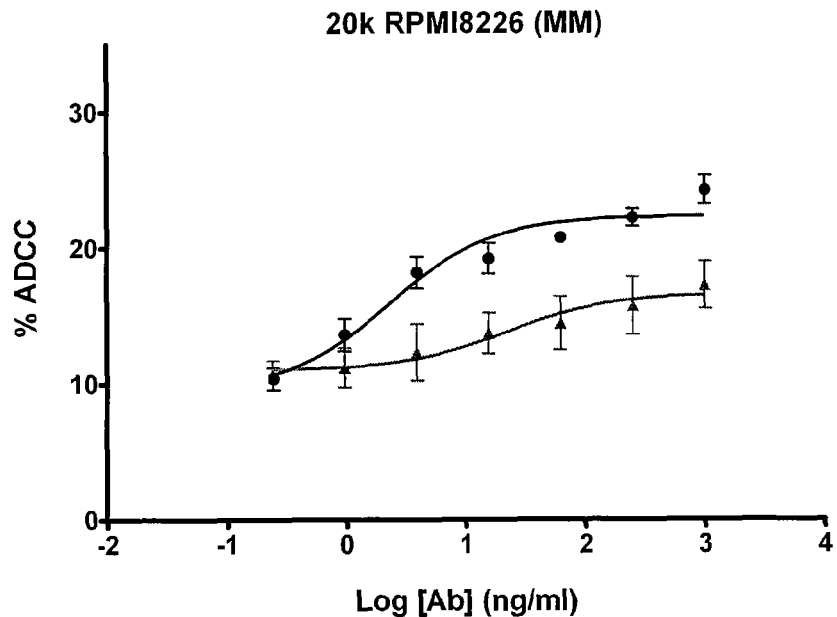
Figure 7
—▲— S2C6 IgG1 (anti-CD40)
—●— S2C6 Hybrid S239D/I332E (anti-CD40)
—■— IV.3 (mouse anti-human FcgRIIa)
—▲— hIgG (isotype control)
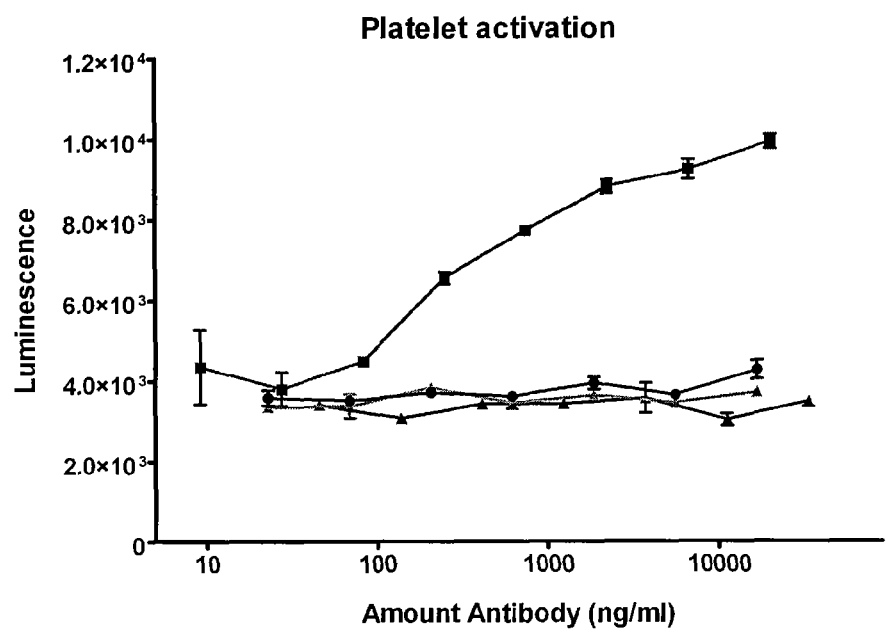

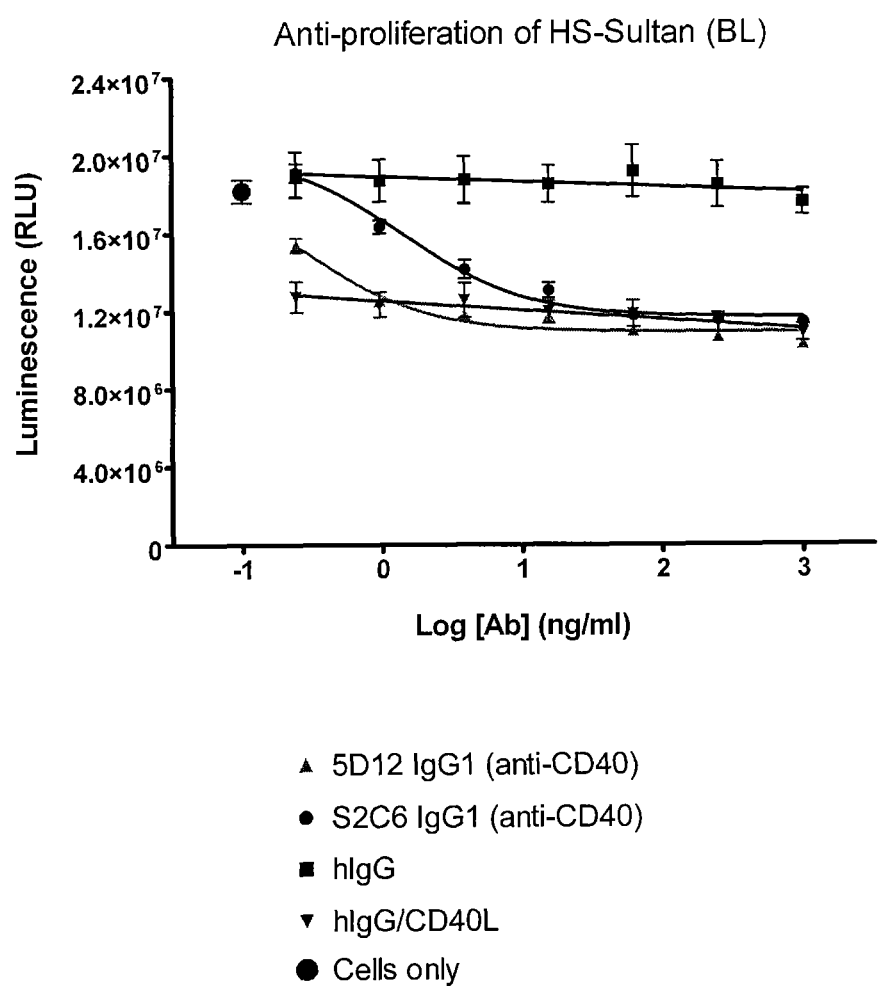

Figure 9

> S2C6 VH (H1) (SEQ ID NO:34)

QVQLVQSGAEVKKPGASVKVSCKASGYSFTGYYIHWVRQAPGQSLEWMGRVIPNNG
GTSYNQKFQGRVTISVDKSISTAYMELSSLRSEDTAVYYCAREGIYWWGHGTLVTVSS

> S2C6 VH (H2) (SEQ ID NO:35)

EVQLVQSGAEVKKPGESLKISCKASGYSFTGYYIHWVRQAPGKSLEWMGRVIPNNGGTSY
NPSLKSRVTISVDKSISTAYMELSSLRSEDTAVYYCAREGIYWWGHGTLVTVSS

> S2C6 VH (H3) (SEQ ID NO:36)

EVQLVQSGAEVKKPGASVKVSCKASGYSFTGYYIHWVRQAPGKSLEWMGRVIPNNG
GTSYNPSLKSRVTISVDKSISTAYLQWSSLKASDTAMYYCAREGIYWWGHGTLVTVSS

> S2C6 VH (H4) (SEQ ID NO:37)

EVQLLESGGGLVQPGGSLRLSCAASGYSFTGYYIHWVRQAPGKSLEWVSRVIPNNG
GTSYNPSLKSRVTISVDKSISTAYLQISSLKAEDTAVYYCAREGIYWWGHGTLVTVSS

Figure 10

> S2C6 VL (L1) (SEQ ID NO:38)

DVVVTQSPLSLPVTPGEPASISCRSSQSLVHSNGNTFLHWYLQKPGQSPQLLIYTVSNR
FSGVPDRFSGSGSGTDFTLKISRVEAEDVGVYFCSQTTHVPWTFGGGTKLEIK

> S2C6 VL (L2) (SEQ ID NO:39)

DVVVTQSPATLSLSPGERATLSCRSSQSLVHSNGNTFLHWYQQKPDQSPKLLIYTVSNRFS
GVPDRFSGSGSGTDFTLTISRLEPEDFAVYFCSQTTHVPWTFGGGTKLEIK

> S2C6 VL (L3) (SEQ ID NO:40)

DVVVTQSPDSLAVSLGERATINCKSSQSLVHSNGNTFLHWYLQKPGQSPQLLIYTVSNRFS
GVPDRFSGSGSGTDFTLTISSLQAEDVGVYFCSQTTHVPWTFGGGTKLEIK

Figure 11
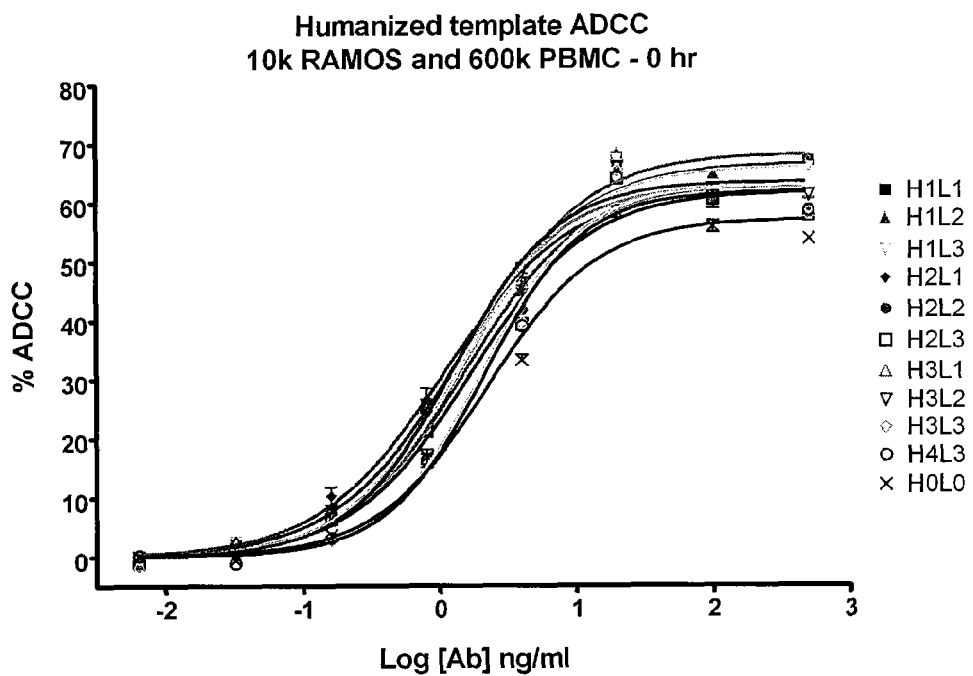
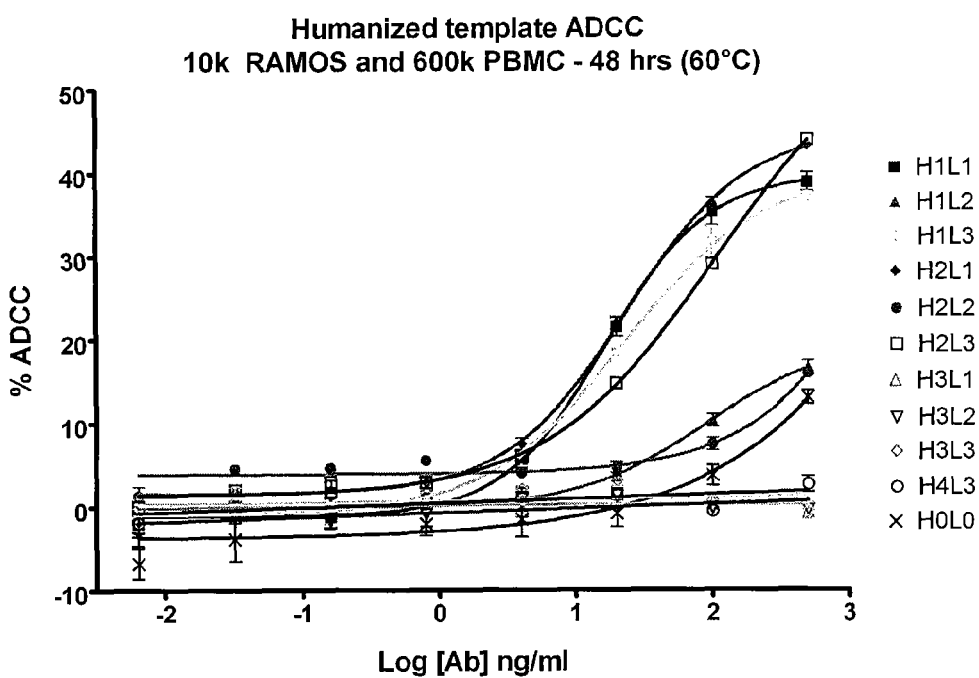

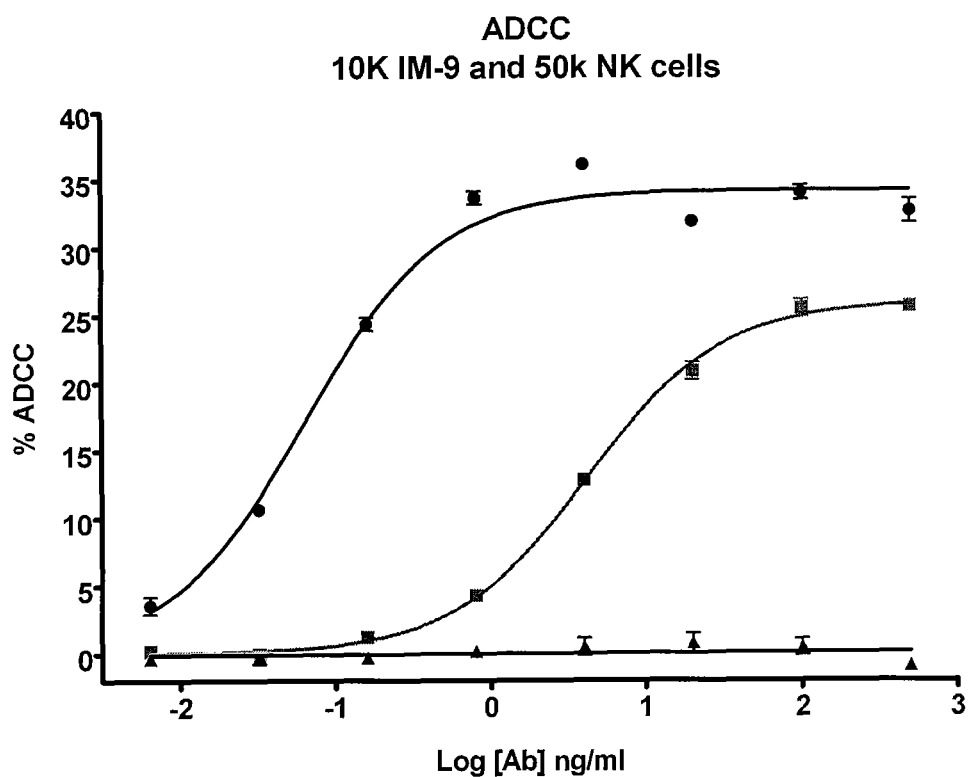

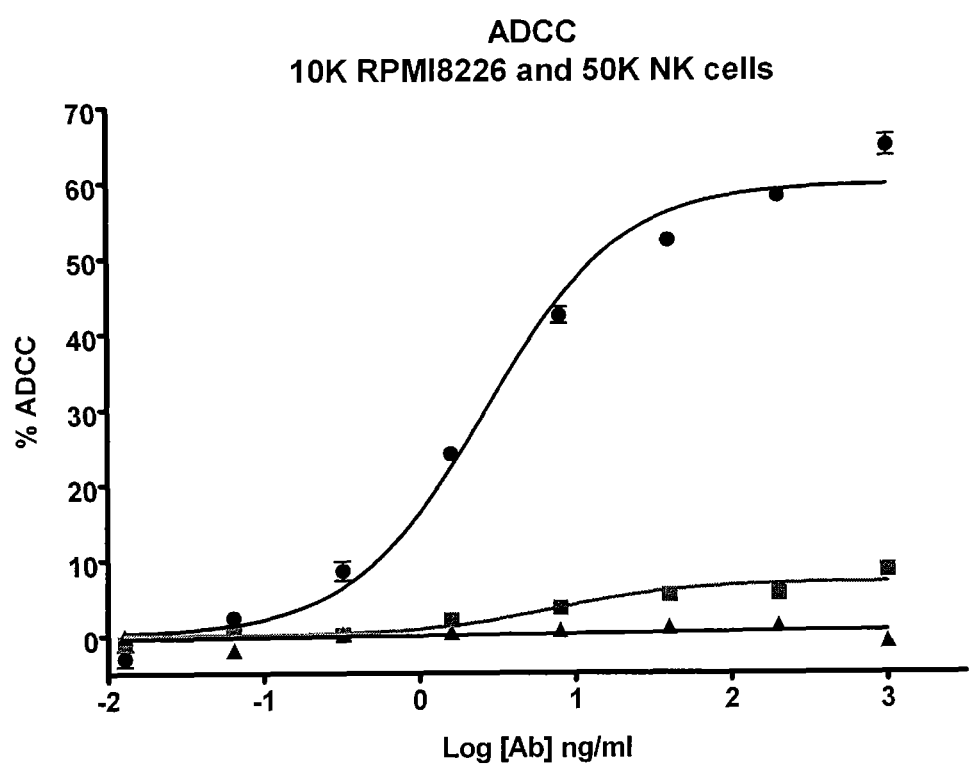

ANTI-CD40 ANTIBODIES AND METHODS OF INHIBITING PROLIFERATION OF CD40 EXPRESSING CELLS

CROSS REFERENCE TO RELATED APPLICATIONS

This patent application is the national stage application of PCT Patent Application No. PCT/US2009/031585, filed Jan. 21, 2009, and entitled "Optimized CD40 Antibodies and Methods of Using the Same," which claims priority to U.S. provisional application No. 61/062,172, filed on Jan. 23, 2008, and entitled "Optimized CD40 Antibodies and Methods of Using the Same," the contents of which are incorporated herein by reference in their entirety.

FIELD OF THE INVENTION

The present invention relates to optimized proteins that target CD40, and their application, particularly for therapeutic purposes.

BACKGROUND

B Cells:

B cells are lymphocytes that play a large role in the humoral immune response. They are produced in the bone marrow of most mammals, and represent 5-15% of the circulating lymphoid pool. The principal function of B cells is to make antibodies against various antigens, and are an essential component of the adaptive immune system.

The human body makes millions of different types of B cells each day that circulate in the blood and lymph performing the role of immune surveillance. B cells, also referred to as B lymphocytes, do not produce antibodies until they become fully activated. Each B cell has a unique receptor protein (referred to as the B cell receptor (BCR)) on its surface that will bind to one particular antigen. The BCR is a membrane-bound immunoglobulin, and it is this molecule that allows the distinction of B cells from other types of lymphocytes, as well as being the main receptor involved in B-cell activation. Once a B cell encounters its cognate antigen and receives an additional signal from a T helper cell, it can further differentiate into the various types of B cells listed below. The B cell may either become one of these cell types directly or it may undergo an intermediate differentiation step, the germinal center reaction, where the B cell will hypermutate the variable region of its immunoglobulin gene and possibly undergo class switching.

B-cell development occurs through several stages, each stage representing a change in the genome content at the antibody loci. The stages of B-cell development include Progenitor B cells, Early Pro-B cells, Late Pro-B cells, Large Pre-B cells, Small Pre-B cells, Immature B cells, and Mature B cells.

Mature B Cells can be Divided into Four Major Types:

B-1 cells express CD5, a marker usually found on T cells. B-1 cells also express IgM in greater quantities than IgG. They secrete natural low affinity polyreactive antibodies found in the serum and often have specificities directed toward self-antigens, and common bacterial polysaccharides. B-1 cells are present in low numbers in the lymph nodes and spleen and are instead found predominantly in the peritoneal and pleural cavities.

B-2 cells are the conventional B cells to which most texts refer. They reside in bone marrow, spleen, and lymph nodes. They are short-lived, and when triggered by antigens may differentiate into IgG-producing memory B cells. In the course of these antibody responses IgG may undergo substantial affinity maturation.

Plasma B cells (also known as plasma cells) are large B cells that have been exposed to antigen and produce and secrete large amounts of antibodies, which assist in the destruction of microbes by binding and facilitating targeting by phagocytes, as well as activation of the complement system. Plasma cells are sometimes referred to as antibody factories.

Memory B cells are formed from activated B cells that are specific to the antigen encountered during the primary immune response. These cells live for a long time, and can respond quickly following a second exposure to the same antigen.

When a B cell fails in any step of the maturation process, it will die by a mechanism called apoptosis. If it recognizes self-antigen during the maturation process, the B cell will become suppressed (known as anergy) or undergo apoptosis. B cells are continuously produced in the bone marrow, but only a small portion of newly made B cells survive to participate in the long-lived peripheral B-cell pool.

In recent years, data have emerged suggesting that B lymphocytes play a broader role in immune responses and are not merely the passive recipients of signals that result in differentiation into antibody-producing plasma cells. Along with their traditional roles as antigen presenting cells and precursors of antibody-producing plasma cells, B cells have also been found to regulate antigen presenting cells (APCs) and T-cell functions, produce cytokines, and express receptor/ligand pairs that previously had been thought to be restricted to other cell types. Described herein are novel antibodies that have been optimized against B cells and methods of using them.

SUMMARY OF THE INVENTION

The present invention is directed to antibodies and methods of using the same. In certain aspects, the antibodies include a variant Fc region. In further embodiments, the antibodies are humanized. The present invention is further directed to methods of using the antibodies in various disease indications.

In one aspect, the present invention is directed to an antibody that binds CD40, wherein said antibody comprises at least one modification in the constant region relative to a parent antibody. In one embodiment, the antibody of the invention binds with altered affinity to an Fc receptor or alters effector function as compared to the parent antibody.

In certain aspects, the modification is an amino acid. The modification can be at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. The amino acid modification can be a substitution selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292I, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330D, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In further aspects, the amino acid modification can be at a position selected from the group consisting of 221, 222, 223, 224, 225, 227, 228, 230, 231, 232, 233, 234, 235, 236, 237, 238, 239, 240, 241, 243, 245, 246, 247, 249, 255, 258, 260, 262, 263, 264, 265, 266, 267, 268, 269, 270, 271, 272, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 324, 325, 326, 327, 328, 329, 330, 331, 332, 333, 334, 335, 336, and 337. In additional aspects, the substitution can be selected from the group consisting of 221K, 222Y, 223E, 223K, 224E, 224Y, 225E, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233F, 233H, 233I, 233K, 233L, 233M, 233N, 233Q, 233R, 233S, 233T, 233V, 233W, 233Y, 234D, 234E, 234F, 234G, 234H, 234I, 234K, 234M, 234N, 234P, 234Q, 234R, 234S, 234T, 234W, 234Y, 235D, 235F, 235G, 235H, 235I, 235K, 235M, 235N, 235Q, 235R, 235S, 235T, 235V, 235W, 235Y, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240M, 240T, 241D, 241E, 241R, 241S, 241W, 241Y, 243E, 243H, 243Q, 243R, 243W, 243Y, 245A, 246D, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267V, 267W, 267Y, 268F, 268G, 268I, 268M, 268P, 268T, 268V, 268W, 269F, 269G, 269H, 269I, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272F, 272G, 272H, 272I, 272K, 272L, 272M, 272P, 272R, 272S, 272T, 272V, 272W, 272Y, 274D, 274E, 274F, 274G, 274H, 274I, 274L, 274M, 274P, 274R, 274T, 274V, 274W, 274Y, 275W, 276D, 276E, 276F, 276G, 276H, 276I, 276L, 276M, 276P, 276R, 276S, 276T, 276V, 276W, 278D, 278E, 278G, 278H, 278I, 278K, 278L, 278M, 278N, 278P, 278Q, 278R, 278S, 278T, 278V, 278W, 280G, 280P, 280W, 281E, 281K, 281N, 281P, 281Y, 282G, 282P, 282Y, 283G, 283H, 283K, 283L, 283P, 283R, 283Y, 284L, 284N, 284Q, 284T, 284Y, 285K, 285Q, 285W, 285Y, 286G, 286P, 286Y, 288Y, 290H, 290L, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296I, 296K, 296L, 296M, 296N, 296Q, 296R, 296S, 296T, 296V, 297D, 297E, 297F, 297G, 297H, 291I, 297K, 297L, 297M, 297P, 297Q, 297R, 297S, 297T, 297V, 297W, 297Y, 298E, 298F, 298H, 298I, 298K, 298M, 298Q, 298R, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301Y, 302I, 303D, 303E, 303Y, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326L, 326P, 326T, 327D, 327E, 327F, 327H, 327I, 327K, 327L, 327M, 327P, 327R, 327V, 327W, 327Y, 328A, 328D, 328E, 328F, 328G, 328H, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330H, 330I, 330L, 330M, 330N, 330P, 330W, 330Y, 331D, 331F, 331H, 331I, 331L, 331M, 331Q, 331R, 331T, 331V, 331W, 331Y, 332A, 332F, 332H, 332L, 332M, 332N, 332P, 332Q, 332S, 332T, 332V, 332W, 332Y, 333F, 333H, 333I, 333L, 333M, 333P, 333T, 333Y, 334F, 334P, 334T, 335D, 335F, 335G, 335H, 335I, 335L, 335M, 335P, 335R, 335S, 335V, 335W, 335Y, 336E, 336K, 336Y, 337H, and 337N.

In further aspects, the modification is at a position selected from the group consisting of 221, 222, 223, 224, 225, 228, 230, 231, 232, 240, 244, 245, 247, 262, 263, 266, 271, 273, 275, 281, 284, 291, 299, 302, 304, 313, 323, 325, 328, 332, 336, wherein the positional numbering is according to the EU index. In additional aspects, the modification is selected from the group consisting of 221K, 221Y, 222E, 222Y, 223E, 223K, 224E, 224Y, 225E, 225K, 225W, 228E, 228G, 228K, 228Y, 230A, 230E, 230G, 230Y, 231E, 231G, 231K, 231P, 231Y, 232E, 232G, 232K, 232Y, 240A, 240I, 240M, 240T, 244H, 245A, 247G, 247V, 262A, 262E, 262F, 262I, 262T, 263A, 263I, 263M, 263T, 266A, 266I, 266M, 266T, 271A, 271D, 271E, 271F, 271G, 271H, 271I, 271K, 271L, 271M, 271N, 271Q, 271R, 271S, 271T, 271V, 271W, 271Y, 273I, 275L, 275W, 281D, 281E, 281K, 281N, 281P, 281Q, 281Y, 284D, 284E, 284L, 284N, 284Q, 284T, 284Y, 291D, 291E, 291G, 291H, 291I, 291Q, 291T, 299A, 299D, 299E, 299F, 299G, 299H, 299I, 299K, 299L, 299M, 299N, 299P, 299Q, 299R, 299S, 299V, 299W, 299Y, 304D, 304H, 304L, 304N, 304T, 313F, 323I, 325A, 325D, 325E, 325F, 325G, 325H, 325I, 325K, 325L, 325M, 325P, 325Q, 325R, 325S, 325T, 325V, 325W, 325Y, 328A, 328D, 328E, 328F, 328G, 328H, 328I, 328K, 328M, 328N, 328P, 328Q, 328R, 328S, 328T, 328V, 328W, 328Y, 332A, 332D, 332E, 332F, 332H, 332K, 332L, 332M, 332N, 332P, 332Q, 332R, 332S, 332T, 332V, 332W, 332Y, 336E, 336K, and 336Y.

The antibody can further include a second amino acid modification at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. The second amino acid modification can be a substitution selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In further aspects, the amino acid modification is 332E. The second amino acid modification can be selected from the group consisting of: 236A, 239D, 332E, 268D, 268E, 330Y, and 330L. In certain embodiments, the second amino acid modification is 239D.

In other aspects, the modification is a glycoform modification that reduces the level of fucose relative to the parent antibody. In still other aspects, the invention is directed to a composition including a plurality of glycosylated antibodies, wherein about 80-100% of the glycosylated antibodies in the composition comprise a mature core carbohydrate structure which lacks fucose.

In a further embodiment, the antibody reduces binding to FcγRIIb as compared to the parent anti-CD40 antibody.

In another aspect, the invention is directed to an antibody that binds CD40, includes a heavy chain and/or a light chain, and has an increased affinity to the FcγRIIIa receptor as compared to the parent antibody. The heavy chain has a CDR1 comprising the amino acid sequence selected from the group consisting of SEQ ID NOs: 16, 22, and 28, a CDR2 comprising an amino acid sequence selected from the group consisting of SEQ ID NOs: 17, 23, and 29, and a CDR3 comprising an amino acid sequence selected from the group consisting of SEQ ID NOs: 18, 24, and 30. The light chain has a CDR1 comprising an amino acid sequence selected from the group consisting of SEQ ID NOs: 19, 25, and 31, a CDR2 comprising an amino acid sequence selected from the group consisting of SEQ ID NOs: 20, 26, and 32, and a CDR3 comprising an amino acid sequence selected from the group consisting of SEQ ID NOs: 21, 27, and 33.

In further variations, the antibody has a variable heavy chain sequence selected from the group consisting of SEQ ID NOs: 10, 12, 14, and 16-19 and/or a variable light chain sequence selected from the group consisting of SEQ ID NOs: 11, 13, 15 and 20-22.

In various additional aspects, the invention is directed to a nucleic acid sequence encoding any of the antibodies disclosed herein.

In further aspects, the invention is directed to a method of treating a B-cell related disease by administering an antibody according to claim 1. In certain variations, the disease is selected from non-Hodgkin's lymphomas (NHL), chronic lymphocytic leukemia (CLL), B-cell acute lymphoblastic leukemia/lymphoma (B-ALL), mantle cell lymphoma (MCL), and multiple myeloma (MM). In certain aspects, the disease is an autoimmune disease, such as rheumatoid arthritis (RA), systemic lupus erythematosus (SLE or lupus), multiple sclerosis, Sjogren's syndrome, and idiopathic thrombocytopenia purpura (ITP).

In further aspects, the invention is directed to a composition comprising an antibody described herein and an acceptable carrier.

In one aspect, the invention is directed toward an antibody that binds CD40, wherein the antibody comprises a means for optimizing effector function. In one embodiment, the means allows for antibody binding with increased affinity to the FcγRIIIa receptor as compared to the parent antibody. In another embodiment, the means is an amino acid modification. In some embodiments, the means is a positional means for optimizing effector function, e.g., modification of an amino acid at one or more of the following heavy chain constant region positions: 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. In other embodiments, the means is a substitutional means for optimizing effector function, e.g., one or more of the following amino acid substitutions in the heavy chain constant region positions: 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In other embodiments, the means for optimizing effector function is a positional means, e.g., modification of an amino acid at one or more of the following positions: 221, 222, 223, 224, 225, 228, 230, 231, 232, 240, 244, 245, 247, 262, 263, 266, 271, 273, 275, 281, 284, 291, 299, 302, 304, 313, 323, 325, 328, 332, 336, wherein the positional numbering is according to the EU index. In some embodiments, the means for optimizing effector function is a substitutional means, e.g., one or more of the following substitutions: 221K, 221Y, 222E, 222Y, 223E, 223K, 224E, 224Y, 225E, 225K, 225W, 228E, 228G, 228K, 228Y, 230A, 230E, 230G, 230Y, 231E, 231G, 231K, 231P, 231Y, 232E, 232G, 232K, 232Y, 240A, 240I, 240M, 240T, 244H, 245A, 247G, 247V, 262A, 262E, 262F, 262I, 262T, 263A, 263I, 263M, 263T, 266A, 266I, 266M, 266T, 271A, 271D, 271E, 271F, 271G, 271H, 271I, 271K, 271L, 271M, 271N, 271Q, 271R, 271S, 271T, 271V, 271W, 271Y, 273I, 275L, 275W, 281D, 281E, 281K, 281N, 281P, 281Q, 281Y, 284D, 284E, 284L, 284N, 284Q, 284T, 284Y, 291D, 291E, 291G, 291H, 291I, 291Q, 291T, 299A, 299D, 299E, 299F, 299G, 299H, 299I, 299K, 299L, 299M, 299N, 299P, 299Q, 299R, 299S, 299V, 299W, 299Y, 304D, 304H, 304L, 304N, 304T, 313F, 323I, 325A, 325D, 325E, 325F, 325G, 325H, 325I, 325K, 325L, 325M, 325P, 325Q, 325R, 325S, 325T, 325V, 325W, 325Y, 328A, 328D, 328E, 328F, 328G, 328H, 328I, 328K, 328M, 328N, 328P, 328Q, 328R, 328S, 328T, 328V, 328W, 328Y, 332A, 332D, 332E, 332F, 332H, 332K, 332L, 332M, 332N, 332P, 332Q, 332R, 332S, 332T, 332V, 332W, 332Y, 336E, 336K, and 336Y. In other embodiments, the means for optimizing effector function includes a modification at a second amino acid, e.g., at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. For example, the means for optimizing effector function may include a substitution at a second amino acid, e.g., one or more of the following substitutions: 221K, 221 Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In another embodiment, the means for optimizing effector function is the amino acid modification 332E. In some embodiments, the means for optimizing effector function is the amino acid modification 332E and one or more of the following amino acid modifications: 236A, 239D, 332E, 268D, 268E, 330Y, and 330L, e.g., 239D.

In other embodiments, an antibody of the invention has a reduced level of fucose relative to the parent antibody. For example, a composition of the invention may comprise a plurality of glycosylated antibodies, wherein about 80-100% of the glycosylated antibodies have a reduced level of fucose.

In other embodiments, an antibody of the invention comprises a means to reduce binding to FcγRIIb as compared to the parent anti-CD40 antibody.

BRIEF DESCRIPTION OF THE DRAWINGS

The following drawings further illustrate aspects of the invention, and are not meant to constrain the present invention to any particular application or theory of operation.

FIG. 1. Sequences of the natural antibody constant regions, including the kappa constant light chain, and the gamma constant heavy chains for IgG1, IgG2, IgG3, and IgG4. Also provided is the sequence of a Hybrid IgG constant chain, and a Hybrid IgG constant chain comprising the substitutions 239D and 1332E.

FIG. 1b. Alignment of the amino acid sequences of the human IgG immunoglobulins IgG1, IgG2, IgG3, and IgG4 (SEQ ID NO:2-5, respectively). FIG. 1b provides the sequences of the CH1 (Cγ1) and hinge domains, and FIG. 1c provides the sequences of the CH2 (Cγ2) and CH3 (Cγ3) domains. Positions are numbered according to the EU index of the IgG1 sequence, and differences between IgG1 and the other immunoglobulins IgG2, IgG3, and IgG4 are shown in gray. Allotypic polymorphisms exist at a number of positions, and thus slight differences between the presented sequences and sequences in the prior art may exist. The possible beginnings of the Fc region are labeled, defined herein as either EU position 226 or 230.

FIG. 1c. Alignment of the amino acid sequences of the human IgG immunoglobulins IgG1, IgG2, IgG3, and IgG4. FIG. 1c provides the sequences of the CH1 (Cγ1), hinge domain, CH2 (Cγ2) domain and CH3 (Cγ3) domain. Positions are numbered according to the EU index of the IgG1 sequence, and differences between IgG1 and the other immunoglobulins IgG2, IgG3, and IgG4 are shown in grey. Polymorphisms exist at a number of positions (Kim et al., 2001, J. Mol. Evol. 54:1-9, incorporated herein by reference in its entirety), and thus slight differences between the presented sequences and sequences in the prior art may exist. The possible beginnings of the Fc region are labeled, defined herein as either EU position 226 or 230.

FIGS. 2a and 2b. The common haplotypes of the gamma chain of human IgG1 (FIG. 2a) and IgG2 (FIG. 2b) showing the positions and the relevant amino acid substitutions.

FIG. 3. Embodiments of receptor binding profiles that include increases to, reductions to, or no effect on the binding to various receptors, where such changes may be beneficial in certain contexts.

FIG. 4: Amino acid sequences of the CD40 antigen targeted by the antibodies of the invention. FIG. 4 provides the sequence of both isoforms of Homo sapiens CD40.

FIGS. 5a-5d. Sequences encoding the murine anti-CD40 antibody variable regions. FIG. 5a provides the light and heavy chain variable region sequences of the anti-CD40 antibodies S2C6, G28-5, and 5D12, respectively. CDRs are underlined. FIGS. 5b-5d describe the CDR sequences of S2C6, G28-5, and 5D12, respectively.

FIGS. 6a-6c. ADCC assay comparing WT IgG1, Hybrid S239D/I332E (effector function enhanced) anti-CD40 antibodies, and the anti-CD20 antibody rituximab on the Burkitt's Lymphoma cell lines Daudi and Raji, and the multiple myeloma cell line RPMI8226. FIG. 6a shows results for S2C6, FIG. 6b shows results for 5D12, and FIG. 6c shows results for G28-5.

FIG. 7. Platelet activation assay with anti-CD40 antibody S2C6. Samples included in the assay were S2C6 IgG1, S2C6 Hybrid S239D/I332E, positive control antibody IV.3 (mouse anti-human IgG FcgRIIa specific antibody), and isotype control antibody.

FIG. 8. Anti-proliferation assay of anti-CD40 antibodies on the Burkitt's Lymphoma cell line HS-Sultan. Samples included in the assay were 5D12 IgG1, S2C6 IgG1, and human IgG with and without CD40 ligand and cells only were used as controls.

FIG. 9. Amino acid sequences of humanized heavy chain S2C6 variants.

FIG. 10. Amino acid sequences of humanized light chain S2C6 variants.

FIG. 11. ADCC of humanized S2C6 templates incubated at 60° C. at 0 and 48 hrs on RAMOS cells in order to assess the relative stability of each template.

FIGS. 12a-12d. ADCC of several humanized S2C6 templates on three different cell lines. FIG. 12a shows ADCC with S2C6 H3L1 Hybrid S239D/I332E, rituximab (anti-CD20), and isotype control (Hybrid S239D/I332E) on the Burkitt's Lymphoma cell line Ramos. FIG. 12b shows ADCC with S2C6 H4L3 Hybrid S239D/I332E, rituximab (anti-CD20), and isotype control (Hybrid S239D/I332E) on the Burkitt's Lymphoma cell line Namalwa. FIG. 12c shows ADCC with S2C6 H1L1 Hybrid S239D/I332E, S2C6 H1L1 IgG1, and isotype control (Hybrid S239D/I332E) on the B-lymphoblastoid cell line IM-9. FIG. 12d shows ADCC with S2C6 H1L1 Hybrid S239D/I332E, S2C6 H1L1 IgG1, and isotype control (Hybrid S239D/I332E) on the multiple myeloma cell line RPMI8226.

FIG. 13 shows a Kaplan-Myer graph delineating the survival of SCID mice injected intravenously (i.v.) with $5\times10^6$ human Ramos Burkitt's lymphoma cells and treated with PBS, isotype control (Hybrid S239D/I332E Fc), 6 mg/kg S2C6 H1L1 Hybrid S239D/I332E (anti-CD40), 2 mg/kg S2C6 H1L1 Hybrid S239D/I332E (anti-CD40), or 0.6 mg/kg S2C6 H1L1 Hybrid S239D/I332E (anti-CD40).

DETAILED DESCRIPTION OF THE INVENTION

Figure 12A:
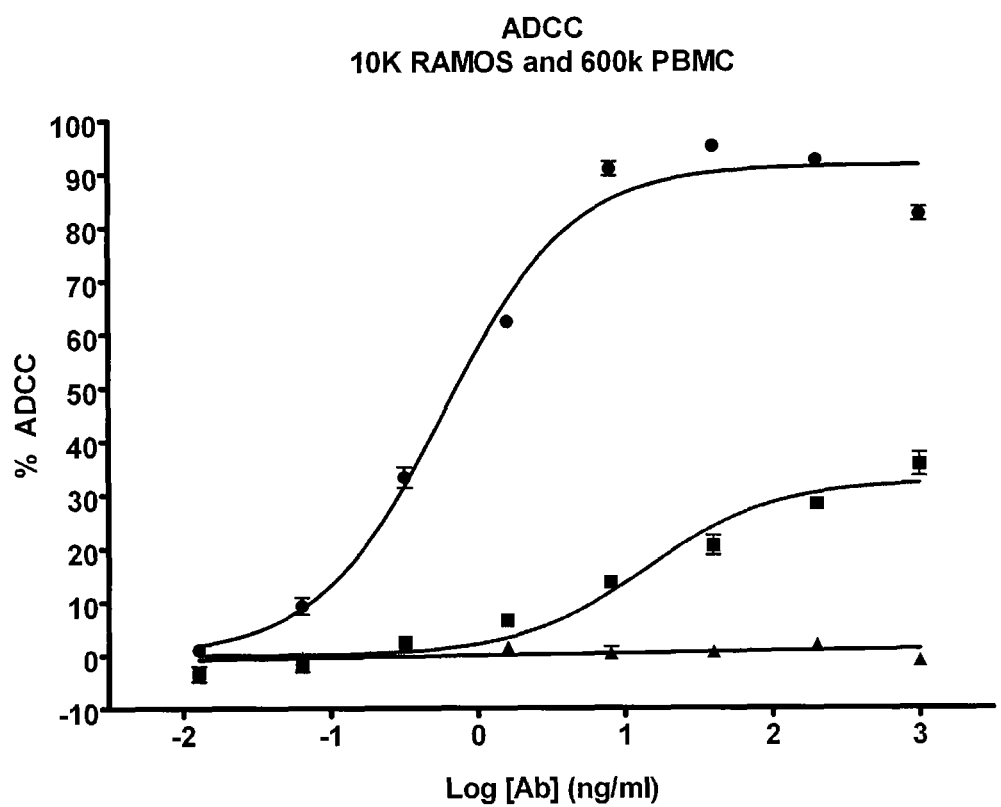

B-Cell Disorders:

Because of their critical role in regulating the immune system, disregulation of B cells is associated with a variety of disorders. B-cell disorders, also referred to herein as B-cell related diseases, are divided into excessive or uncontrolled proliferation (lymphomas, leukemias), and defects of B-cell development/immunoglobulin production (immunodeficiencies). The majority (80%) of lymphoma cases are of B-cell origin. These include non-Hodgkin's lymphoma (NHL), acute lymphoblastic leukemia (ALL), and autoimmune related diseases.

NHL is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years of age, with the incidence increasing with age. NHL is characterized by a clonal proliferation of lymphocytes that accumulate in the lymph nodes, blood, bone marrow and spleen, although any major organ may be involved.

The diagnosis and histologic characterization of NHL is made using a combination of morphologic and immunophenotype criteria. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. For consistency the present document will also use a similar division. The indolent NHL group is comprised primarily of follicular subtypes, small lymphocytic lymphoma, MALT, and marginal zone; indolent encompasses approximately 50% of newly diagnosed B-cell NHL patients. Aggressive NHL includes patients with histologic diagnoses of primarily diffuse large B cell (40% of all newly diagnosed patients have diffuse large cell), Burkitt's, and mantle cell. The clinical course of NHL is highly variable. A major determinant of clinical course is the histologic subtype. Most indolent types of NHL are considered to be incurable diseases. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); cyclophosphamide, adriamycin, vincristine, prednisone (CHOP); or the purine analog, fludarabine. Approximately 70% to 80% of patients will respond to their initial chemotherapy, duration of remissions last on the order of 2-3 years. Ultimately the majority of patients relapse. The discovery and clinical use of the anti-CD20 antibody, rituximab, has provided significant improvements in response and survival rate. The current standard of care for most patients is rituximab+CHOP (R-CHOP) or rituximab+CVP (R-CVP). Interferon is approved for initial treatment of NHL in combination with alkylating agents, but has limited use in the U.S.

Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete response rate in relapsed population), and a continued pattern of relapse. Finally, many B cells do not express CD20, and thus many B-cell disorders are not treatable using anti-CD20 antibody therapy. Antibodies against antigens other than CD20 may have anti-lymphoma effects that could overcome anti-CD20 resistance or augment the activity of anti-CD20 therapy.

In addition to NHL there are several types of leukemias that result from disregulation of B cells. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review).

CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Although the purine analogue fludarabine was shown to give superior response rates than chlorambucil as primary therapy, there is no evidence that early use of fludarabine improves overall survival. Combination chemotherapy regimens such as fludarabine with cyclophosphamide, FCR (fludarabine, cyclophosphamide and rituximab) and CHOP are effective in both newly-diagnosed and relapsed CLL. Allogeneic bone marrow (stem cell) transplantation is rarely used as a first-line treatment for CLL due to its risk.

"Refractory" CLL is a disease that no longer responds favorably to treatment. In this case more aggressive therapies, including bone marrow (stem cell) transplantation, are considered. The monoclonal antibody alemtuzumab, directed against CD52, may be used in patients with refractory, bone marrow-based disease.

Another type of leukemia is acute lymphoblastic leukemia (ALL), also known as acute lymphocytic leukemia. ALL is characterized by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than those of other ages. Currently, at least 80% of childhood ALL are considered curable. Under 4,000 cases are diagnosed every year and the mortality rate is almost 1,500 a year (American Cancer Society, 2006; and SEER Cancer Statistics Review).

Multiple myeloma (MM) is a B-cell malignancy with terminally differentiated plasma cells. The disease subsequently attacks bone and bone marrow, which results in multiple tumors and lesions throughout the skeletal system. It is the second most common hematologic malignancy in the United States, afflicting approximately 55,000 people there alone. The annual incidence rate for multiple myeloma is 3 to 4 cases per 100,000 people, making it the most common bone tumor cancer in adults. Current treatment protocols which include a combination of chemotherapeutic agents yield a complete remission rate of only about 5%, with a median survival of approximately 36-48 months from the time of diagnosis. Treatment regimens are limited by a low cell proliferation rate and the development of multi-drug resistance. Therefore, alternative treatment regimens using therapeutic antibodies targeting surface antigens on plasma cells would be of great benefit.

Autoimmunity results from a breakdown of self-tolerance involving humoral and/or cell-mediated immune mechanisms. The consequences of failure in central and/or peripheral tolerance include survival and activation of self-reactive B cells and T cells. Examples of autoimmune diseases include, for example, rheumatoid arthritis (RA), systemic lupus erythematosus (SLE or lupus), multiple sclerosis (MS), Sjogren's syndrome, and idiopathic thrombocytopenia purpura (ITP). The pathogenesis of most autoimmune diseases is coupled to the production of autoantibodies against self antigens, leading to a variety of associated pathologies. Autoantibodies are produced by terminally differentiated plasma cells that are derived from naïve or memory B cells. Furthermore, B cells can have other effects on autoimmune pathology, as antigen-presenting cells (APCs) that can interact with and stimulate helper T cells, further stimulating the cycle of anti-self immune response. Depletion of B cells can have direct impact on the production of autoantibodies. Indeed, treatment of RA and SLE with B-cell depletion therapies such as rituximab has been demonstrated to have clinical benefit for both disease classes (Edwards & Cambridge, Nat. Rev. Immunol. 2006; Dass et al., Future Rheumatol. 2006; Martin & Chan, Annu. Rev. Immunol. 2006, each incorporated herein it its entirety by reference).

Antibodies as Therapeutics to Treat B-Cell Disorders and Solid Tumors

Monoclonal antibodies are a class of therapeutic proteins that may be used to treat B-cell disorders. A number of favorable properties of antibodies, including but not limited to specificity for target, ability to mediate immune effector mechanisms, and long half-life in serum, make antibodies powerful therapeutics. The present invention describes antibodies against the B-cell and solid tumor antigen CD40.

CD40:

The CD40 antigen is a cell surface glycoprotein which belongs to the tumor necrosis factor receptor (TNF-R) family and is expressed on the surface of all mature B cells, most mature B-cell malignancies, some early B-cell acute lymphocytic leukemias, and ~70% of all solid tumors. CD40 is also expressed on dendritic cells, monocytes, endothelial cells, epithelial cells, fibroblasts, smooth muscle cells, and many human solid tumors, including melanoma and carcinomas. Signaling via CD40 activates antigen-presenting cells, including B-cells and dendritic cells. CD154, which is the natural ligand of CD40, is expressed on the surface of activated T-lymphocytes and provides a large component of T-cell triggering for immune responses. Consequently, CD40 agonists trigger immune responses against many tumor-associated antigens. Because of these properties, and its expression on many B-cell malignancies and solid tumors, therapeutic anti-CD40 antibodies would be of great value in treating disease.

CD40 is a 50-kd type I transmembrane protein of the TNFR family that includes TNFR-1, TNFR-2, CD30, CD27, 4-1BB, OX40, and Fas. The gene-encoding CD40 is located at chromosome 20 in humans and chromosome 2 in mice. Correlated with its immune regulatory function in various cell types, CD40 is expressed widely on B cells, DCs, monocytes and macrophages, thymic epithelial cells, endothelial cells, mast cells, fibroblasts, and smooth muscle cells. CD40 ligand (CD154) is produced as a type II transmembrane protein with an apparent molecular mass of 32 to 33 kd. It is a member of the TNF family, which also includes TNF-α, CD153, CD70, 4-1BBL, OX40L, and FasL. Soluble forms of CD154 exist as 31 or 18-kd proteins, both of which retain the biologic activities of the membrane-bound CD154, and can potentially act as cytokines on distal CD40+ cells. The gene-encoding CD154 is located on the X chromosome in both humans and mice. Mutations in the CD154 gene result in the X-linked hyper-immunoglobulin (Ig) M syndrome in humans. CD154 expression, originally thought to be restricted to activated T cells, mainly of the CD4 lineage, has now been identified on CD8+T cells, B cells, eosinophils, mast cells, basophils, DCs, and other cell types. Recently, platelets were found to express CD154 as well.

Originally identified as the molecular interaction between T and B cells, the CD154-CD40 pathway plays a key role in regulating thymus-dependent humoral responses. Indeed, patients with X-linked hyper-IgM syndrome have elevated IgM levels but low levels of IgA, IgG, and IgE; are devoid of the germinal centers; and are unable to mount thymus-dependent humoral responses. In mice, CD154-CD40 signaling was shown to be critical in regulating B-cell proliferation, Ig production, Ig class switching, rescue of B cells from apoptosis, germinal center formation, generation of B-cell memory, and clonal expansion and deletion of B cells.

Most APC at the resting stage express low levels of costimulatory molecules, such as CD80 or CD86. CD40 ligation by CD154 from T cells represents a key step in APC activation to enhance costimulatory molecule expression, which enables them to be competent to fully activate T cells. Induction of proinflammatory cytokines, including interleukin (IL) 12 by DCs, is another outcome of this APC interaction, which is critical for the development of TH1-type immune responses. Thus blockade of the CD154-CD40 pathway will result in a deficiency of APC activation, which will obviously also lead to the global failure of T-cell activation. However, this indirect impact on T cells is not the only reason for ineffective T-cell responses after CD154 blockade. It is now realized that CD154-CD40 interaction is bidirectional. Because in vitro CD154 ligation on T cells significantly enhances cytokine production, particularly of the TH2 type, cross-linking of CD154 on CD4 T cells in vivo contributes to the generation of helper function and germinal center. CD154-CD40 interaction provides the molecular basis for CD4 help in activation of cytotoxic CD8+ T cells, with DCs serving as a bridge between the 2 cell types. Although the molecular details of this 3-cell interaction have not been fully elucidated, it is now clear that activated CD4+ T cells stimulate DCs via CD154-CD40 and enable DCs to subsequently activate CD8+ T cells to differentiate into cytotoxic effectors.

CD40 is expressed on many nonhematopoietic cells, particularly under the proinflammatory conditions. Cross-linking of CD40 on vascular endothelial cells activates these cells and increases expression of adhesion molecules, such as CD62E, CD106, CD54, and chemokines and cytokines, including IL-6 and IL-8. This may promote extravasation and accumulation of activated T cells at the sites of inflammation. In addition to activated T cells, platelets may provide another source of endothelial activation. Indeed, thrombin-activated platelets rapidly up-regulate CD154 expression, which may then interact with CD40 on endothelial cells and thus contribute to chemotactic effects from endothelial activation or damage, independently of T cells. This may have contributed, at least in part, to unexpected thromboembolic complications recently detected in primates and humans treated with some CD154 antibodies.

CD154/CD40 signaling is also crucially important for controlling immunity and inflammation. The emerging picture indicates that ligation of the receptor CD40 via CD154, most potently in its trimeric form, functions in two ways. CD154 modulates physiologic processes, such as T cell-mediated effector functions and general immune responses required for appropriate host defense, but also triggers the expression of pro-inflammatory mediators, such as cytokines, adhesion molecules, and matrix degrading activities, all of which are associated with the pathogenesis of chronic inflammatory diseases, e.g., autoimmune disorders, arthritis, atherosclerosis, and cancer. Accordingly, CD40/CD154 interactions have advanced as a potential therapeutic target for these diseases, whereby two opposing strategies, interruption as well as enhancement of CD40 signaling, are explored for beneficial outcomes. Besides their crucial role in T-cell-dependent humoral immunity, CD40-CD40L interactions have thus been implicated in autoimmune diseases, such as atherosclerosis, asthma, systemic lupus erythematosus, multiple sclerosis, graft versus host disease, experimental autoimmune encephalitis and rheumatoid arthritis.

Fc Optimization of Antibodies May Provide Improved Clinical Performance

The clinical success of antibodies directed against CD40 will depend heavily on their potential mechanism(s) of action. There are a number of possible mechanisms by which antibodies mediate cellular effects, including anti-proliferation via blockage of needed growth pathways, intracellular signaling leading to apoptosis, enhanced down regulation and/or turnover of receptors, complement-dependent cytotoxicity (CDC), antibody-dependent cell-mediated cytotoxicity (ADCC), antibody-dependent cell-mediated phagocytosis (ADCP) and promotion of an adaptive immune response (Cragg at al., 1999, Curr Opin Immunol 11:541-547; Glennie et al., 2000, Immunol Today 21:403-410, each incorporated herein it its entirety by reference). Antibody efficacy may be due to a combination of these mechanisms, and their relative importance in clinical therapy for oncology appears to be cancer dependent.

The importance of FcγR-mediated effector functions for the activity of some antibodies has been demonstrated in mice (Clynes et al., 1998, Proc Natl Acad Sci USA 95:652-656; Clynes et al., 2000, Nat Med 6:443-446, each incorporated herein it its entirety by reference), and from observed correlations between clinical efficacy in humans and their allotype of high (V158) or low (F158) affinity polymorphic forms of FcγRIIIa (Cartron et al., 2002, Blood 99:754-758; Weng & Levy, 2003, Journal of Clinical Oncology, 21:3940-3947, each incorporated herein it its entirety by reference). Together these data suggest that an antibody that is optimized for binding to certain FcγRs may better mediate effector functions, and thereby destroy target cells more effectively in patients. Thus a promising means for enhancing the anti-tumor potency of antibodies is via enhancement of their ability to mediate cytotoxic effector functions such as ADCC, ADCP, and CDC. Additionally, antibodies can mediate anti-tumor mechanism via growth inhibitory or apoptotic signaling that may occur when an antibody binds to its target on tumor cells. Such signaling may be potentiated when antibodies are presented to tumor cells bound to immune cells via FcγR. Therefore increased affinity of antibodies to FcγRs may result in enhanced anti-proliferative effects.

Some success has been achieved at modifying antibodies with selectively enhanced binding to FcγRs to provide enhanced effector function. Antibody engineering for optimized effector function has been achieved using amino acid modifications (see for example U.S. Ser. No. 10/672,280 and U.S. Ser. No. 11/124,620 and references cited therein, each incorporated herein it its entirety by reference), and engineered glycoforms (see for example Umana et al., 1999, Nat Biotechnol 17:176-180; Shinkawa et al., 2003, J Biol Chem 278:3466-3473, Yamane-Ohnuki et al., 2004, Biotechnology and Bioengineering 87(5):614-621, each incorporated herein it its entirety by reference).

Unfortunately, it is not known a priori which mechanisms of action may be optimal for a given target antigen. Furthermore, it is not known which antibodies may be capable of mediating a given mechanism of action against a target cell. In some cases a lack of antibody activity, either Fv-mediated or Fc-mediated, may be due to the targeting of an epitope on the target antigen that is poor for mediating such activity. In other cases, the targeted epitope may be amenable to a desired Fv-mediated or Fc-mediated activity, yet the affinity (affinity of the Fv region for antigen or affinity of the Fc region for Fc receptors) may be insufficient. Towards addressing this problem, the present invention describes modifications to anti-CD40 antibodies that provide optimized Fv- and Fc-mediated activities.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid" and "amino acid identity" as used herein is meant one of the 20 naturally occurring amino acids or any non-natural analogues that may be present at a specific, defined position. Thus "amino acid" as used herein is both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In a embodiment, the amino acids are in the (S) or L-configuration. If non-naturally occurring side chains are used, non-amino acid substituents may be used, for example to prevent or retard in vivo degradation.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "B cell" or "B lymphocyte" as used herein is meant a type of lymphocyte developed in bone marrow that circulates in the blood and lymph, and provides humoral immunity. B cells recognize free antigen molecules and differentiate or mature into plasma cells that secrete immunoglobulin (antibodies) that inactivate the antigens. Memory cells are also generated that make the specific Immunoglobulin (antibody) on subsequent encounters with such antigen. B cells are also known as "Beta cells" in the islet of Langerhans.

By "B-cell antigen" or "B-cell marker" as used herein is meant any protein that is expressed on B cells. B-cell markers of the invention include CD40.

By "CD40" as used herein is meant the protein encoded by the gene designated CD40. CD40 is also known as Tumor necrosis factor receptor superfamily member 5 (TNFRSF5), CD40L receptor, CD154 receptor, B-cell surface antigen CD40, CDw40, and Bp50. Human CD40 is designated GeneID:958 by Entrez Gene (Maglott et al., 2005, Nucleic Acids Res 33(Database Issue):D54-D58, and HGNC:11919 by HUGO (The Human Genome Organisation) Gene Nomenclature Committee (HGNC) (Wain et al., 2004, Genew: the Human Gene Nomenclature Database, 2004 updates, Nucleic Acids Res 32 Database issue:D255-7. The use of CD40 herein is meant to encompass all known or as yet undiscovered alleles and polymorphic forms of CD40. The sequence of human CD40 antigen used in the present study is provided in FIG. 4, SEQ ID NO: 8.

By "CDC" or "complement dependent cytotoxicity" as used herein is meant the reaction wherein one or more complement protein components recognize bound antibody on a target cell and subsequently cause lysis of the target cell.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ or Cλ, wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, incorporated herein it its entirety by reference), as well as any undiscovered human FcγRs or FcγR isoforms or allotypes. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes. An FcγR may be from any organism, including but not limited to humans, mice, rats, rabbits, and monkeys.

By "Fc ligand" or "Fc receptor" as used herein is meant a molecule, e.g., a polypeptide, from any organism that binds to the Fc region of an antibody to form an Fc-ligand complex. Fc ligands include but are not limited to FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, *Immunological Reviews* 190:123-136, incorporated herein it its entirety by reference). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoqlobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoqlobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "modification" herein is meant an alteration in the physical, chemical, or sequence properties of a protein, polypeptide, antibody, or immunoglobulin. Modifications of the invention are amino acid modifications and glycoform modifications.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution I332E refers to a variant polypeptide, in this case a constant heavy chain variant, in which the isoleucine at position 332 is replaced with glutamic acid. The WT residue may or may not be designated. For the preceding example, 332E indicates the substitution of position 332 with a glutamic acid. For the purposes herein, multiple substitutions are typically separated by a slash. For example, 239D/332E refers to a double variant comprising the substitutions 239D and 332E. By "amino acid insertion" or "insertion" as used herein is meant the addition of an amino acid at a particular position in a parent polypeptide sequence. For example, insert –236G designates an insertion of glycine at position 236. By "amino acid deletion" or "deletion" as used herein is meant the removal of an amino acid at a particular position in a parent polypeptide sequence. For example, G236– designates the deletion of glycine at position 236.

By "glycoform modification" or "modified glycoform" or "engineered glycoform" as used herein is meant a carbohydrate composition that is covalently attached to a protein, for example an antibody, wherein the carbohydrate composition differs chemically from that of a parent protein. Modified glycoform typically refers to the different carbohydrate or oligosaccharide; thus for example an antibody may comprise a modified glycoform. Alternatively, modified glycoform may refer to the antibody that comprises the different carbohydrate or oligosaccharide.

By "parent polypeptide", "parent protein", "precursor polypeptide", or "precursor protein" as used herein is meant a polypeptide that is subsequently modified to generate a variant, e.g., any polypeptide which serves as a template and/or basis for at least one amino acid modification described herein. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent antibody" or "parent immunoglobulin" as used herein is meant an antibody or immunoglobulin that is modified to generate a variant (e.g., a parent antibody may include, but is not limited to, a protein comprising the constant region of a naturally occurring Ig).

By "protein" or "polypeptide" as used herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids.

By "position" as used herein is meant a location in the sequence of a protein. Positions may be numbered sequentially, or according to an established format, for example the EU index as in Kabat. Corresponding positions are determined as outlined herein, generally through alignment with other parent sequences.

By "residue" as used herein is meant a position in a protein and its associated amino acid identity. For example, Asparagine 297 (also referred to as Asn297 and N297) is a residue at position 297 in the human antibody IgG1.

By "target antigen" or "target" or "antigen" as used herein is meant the molecule that is bound specifically by the variable region of a given antibody. A target antigen may be a protein, carbohydrate, lipid, or other chemical compound. By "target cell" as used herein is meant a cell that expresses a target antigen.

By "variable region" as used herein is meant the region of an immunoglobulin that comprises one or more Ig domains substantially encoded by any of the Vκ, Vλ, and/or $V_H$ genes that make up the kappa, lambda, and heavy chain immunoglobulin genetic loci respectively.

By "variant protein", "protein variant", "variant polypeptide", or "polypeptide variant" as used herein is meant a polypeptide sequence that differs from that of a parent polypeptide sequence by virtue of at least one amino acid modification or at least one glycoform modification. Variant polypeptide may refer to the polypeptide itself, a composition comprising the polypeptide, or the amino sequence that encodes it. In one embodiment, the variant polypeptide has at least one amino acid modification compared to the parent polypeptide, e.g. from about one to about ten amino acid modifications, e.g., from about one to about five amino acid modifications compared to the parent. The variant polypeptide sequence herein may possess at least about 80% homology with a parent polypeptide sequence, e.g., at least about 90% homology, at least about 95% homology, etc. Accordingly, by "variant antibody" or "antibody variant" as used herein is meant an antibody sequence that differs from that of a parent antibody sequence by virtue of at least one amino acid modification or at least one glycoform modification. Variant antibody or antibody variant may refer to the antibody polypeptide itself, compositions comprising the antibody variant polypeptide, or the amino acid sequence that encodes it. Accordingly, by "constant heavy chain variant" or "constant light chain variant" or "Fc variant" as used herein is meant a constant heavy chain, constant light chain, or Fc region polypeptide or sequence, respectively, that differs in sequence from that of a parent sequence by virtue of at least one amino acid modification or at least one glycoform modification.

By "wild type or WT" herein is meant an amino acid sequence or a nucleotide sequence that is found in nature, including allelic variations. A WT protein, polypeptide, antibody, immunoglobulin, IgG, etc., has an amino acid sequence or a nucleotide sequence that has not been intentionally modified.

For all immunoglobulin heavy chain constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, incorporated herein it its entirety by reference). The "EU index as in Kabat" refers to the residue numbering of the human IgG1 EU antibody, as described in Edelman et al., 1969, Biochemistry 63:78-85, incorporated herein it its entirety by reference.

Antibodies

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Natural antibody structural units typically comprise a tetramer. Each tetramer is typically composed of two identical pairs of polypeptide chains, each pair having one "light" chain (typically having a molecular weight of about 25 kDa) and one "heavy" chain (typically having a molecular weight of about 50-70 kDa). Each of the light and heavy chains are made up of two distinct regions, referred to as the variable and constant regions. For the IgG class of immunoglobulins, the heavy chain is composed of four immunoglobulin domains linked from N- to C-terminus in the order $V_H$-CH1-CH2-CH3, referring to the heavy chain variable domain, heavy chain constant domain 1, heavy chain constant domain 2, and heavy chain constant domain 3 respectively (also referred to as $V_H$-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order $V_L$-$C_L$, referring to the light chain variable domain and the light chain constant domain respectively. The constant regions show less sequence diversity, and are responsible for binding a number of natural proteins to elicit important biochemical events.

The variable region of an antibody contains the antigen binding determinants of the molecule, and thus determines the specificity of an antibody for its target antigen. The variable region is so named because it is the most distinct in sequence from other antibodies within the same class. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated $V_H$CDR1, $V_H$CDR2, $V_H$CDR3, $V_L$ CDR1, $V_L$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, and the conserved features of antibodies are disclosed, for example, in Maynard et al., 2000, Annu Rev Biomed Eng 2:339-376, each incorporated herein it its entirety by reference.

Antibodies are grouped into classes, also referred to as isotypes, as determined genetically by the constant region. Human constant light chains are classified as kappa (Cκ) and lambda (Cλ) light chains. Human heavy chains are classified as mu, delta, gamma, alpha, or epsilon, and define the antibody's isotype as IgM, IgD, IgG, IgA, and IgE, respectively. The IgG class is the most commonly used for therapeutic purposes. By "IgG" as used herein is meant a polypeptide belonging to the class of antibodies that are substantially encoded by a recognized immunoglobulin gamma gene. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. FIG. 1 provides the sequences of the human light chain kappa and heavy chain gamma constant chains. FIGS. 1b & 1c shows an alignment of the human IgG constant heavy chains.

Also useful for the invention may be IgGs that are hybrid compositions of the natural human IgG isotypes. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (Michaelsen et al., 1992, Molecular Immunology, 29(3): 319-326, entirely incorporated by reference). A number of studies have explored IgG1, IgG2, IgG3, and IgG4 variants in order to investigate the determinants of the effector function differences between them. See for example Canfield & Morrison, 1991, J. Exp. Med. 173: 1483-1491; Chappel et al., 1991, Proc. Natl. Acad. Sci. USA 88(20): 9036-9040; Chappel et al., 1993, Journal of Biological Chemistry 268:25124-25131; Tao et al., 1991, J. Exp. Med. 173: 1025-1028; Tao et al., 1993, J. Exp. Med. 178: 661-667; Redpath et al., 1998, Human Immunology, 59, 720-727, all entirely incorporated by reference.

As described in U.S. Ser. No. 11/256,060, filed Oct. 21, 2005, entitled "IgG Immunoglobulin Variants with Optimized Effector Function", herein expressly incorporated by reference, it is possible to engineer amino acid modifications in an antibody that comprise constant regions from other immunoglobulin classes, for example as those illustrated in the alignments in FIG. 1. Such engineered hybrid IgG compositions may provide improved effector function properties, including improved ADCC, phagocytosis, CDC, and serum half-life. For example, as illustrated by FIG. 1, an IgG1/IgG3 hybrid variant may be constructed by substituting IgG1 positions in the CH2 and CH3 region with the amino acids from IgG3 at positions where the two isotypes differ. Thus a hybrid variant IgG antibody may be constructed that comprises one or more substitutions selected from the group consisting of: 274Q, 276K, 300F, 339T, 356E, 358M, 384S, 392N, 397M, 422I, 435R, and 436F, wherein numbering is according to the EU index. Such variant may provide alternate and/or improved effector function properties.

As another example, relatively poor effector function of IgG2 may be improved by replacing key FcγR binding residues with the corresponding amino acids in an IgG with better effector function. For example, key residue differences between IgG2 and IgG1 with respect to FcγR binding may include P233, V234, A235, –236 (referring to a deletion in IgG2 relative to IgG1), and G327. Thus one or more amino acid modifications in the parent IgG2 wherein one or more of these residues is replaced with the corresponding IgG1 amino acids, P233E, V234L, A235L, -236G (referring to an insertion of a glycine at position 236), and G327A, may provide enhanced effector function. The sequence of such an IgG, comprising a hybrid of residues from IgG1 and IgG2, referred to herein as "Hybrid", is provided in FIG. 1.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem. Immunol. 65:88-110; Gorman & Clark, 1990, Semin. Immunol. 2(6):457-66, each incorporated herein it its entirety by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; E. van Loghem, 1986, Allotypic markers, Monogr Allergy 19: 40-51, each incorporated herein it its entirety by reference). Additionally, other polymorphisms have been characterized (Kim, et al., 2001, J. Mol. Evol. 54:1-9, incorporated herein it its entirety by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, each incorporated herein it its entirety by reference). Allotypes that are inherited in fixed combinations are called Gm haplotypes. FIG. 2 shows common haplotypes of the gamma chain of human IgG1 (FIG. 2a) and IgG2 (FIG. 2b) showing the positions and the relevant amino acid substitutions. The antibodies of the present invention may be substantially encoded by any allotype, isoallotype, or haplotype of any immunoglobulin gene.

Antibodies of the present invention may be substantially encoded by genes from any organism, e.g., mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In one embodiment, the antibodies of the present invention are substantially human. The antibodies of the present invention may be substantially encoded by immunoglobulin genes belonging to any of the antibody classes. In one embodiment, the antibodies of the present invention comprise sequences belonging to the IgG class of antibodies, including human subclasses IgG1, IgG2, IgG3, and IgG4. In an alternate embodiment, the antibodies of the present invention comprise sequences belonging to the IgA (including human subclasses IgA1 and IgA2), IgD, IgE, IgG, or IgM classes of antibodies. The antibodies of the present invention may comprise more than one protein chain. That is, the present invention may find use in an antibody that is a monomer or an oligomer, including a homo- or hetero-oligomer.

In one embodiment, the antibodies of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgD, IgM, and the like. It is contemplated that, although the antibodies of the present invention are engineered in the context of one parent antibody, the variants may be engineered in or "transferred" to the context of another, second parent antibody. This is done by determining the "equivalent" or "corresponding" residues and substitutions between the first and second antibodies, typically based on sequence or structural homology between the sequences of the two antibodies. In order to establish homology, the amino acid sequence of a first antibody outlined herein is directly compared to the sequence of a second antibody. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first antibody are defined. Alignment of conserved residues may conserve 100% of such residues. However, alignment of greater than 75% or as little as 50% of conserved residues is also adequate to define equivalent residues. Equivalent residues may also be defined by determining structural homology between a first and second antibody that is at the level of tertiary structure for antibodies whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm, e.g., 0.1 nm, after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent antibody in which the antibodies are made, what is meant to be conveyed is that the antibodies discovered by the present invention may be engineered into any second parent antibody that has significant sequence or structural homology with the antibody. Thus for example, if a variant antibody is generated wherein the parent antibody is human IgG1, by using the methods described above or other methods for determining equivalent residues, the variant antibody may be engineered in a human IgG2 parent antibody, a human IgA parent antibody, a mouse IgG2a or IgG2b parent antibody, and the like. Again, as described above, the context of the parent antibody does not affect the ability to transfer the antibodies of the present invention to other parent antibodies. For example, the variant antibodies that are engineered in a human IgG1 antibody that targets one antigen epitope may be transferred into a human IgG2 antibody that targets a different antigen epitope, and so forth.

In the IgG class of immunoglobulins, there are several immunoglobulin domains in the heavy chain. By "immunoglobulin (Ig) domain" herein is meant a region of an immunoglobulin having a distinct tertiary structure. Of interest in the present invention are the domains of the constant heavy chain, including, the constant heavy (CH) domains and the hinge. In the context of IgG antibodies, the IgG isotypes each have three CH regions: "CH1" refers to positions 118-220, "CH2" refers to positions 237-340, and "CH3" refers to positions 341-447 according to the EU index as in Kabat. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. The constant heavy chain, as defined herein, refers to the N-terminus of the CH1 domain to the C-terminus of the CH3 domain, thus comprising positions 118-447, wherein numbering is according to the EU index. The constant light chain comprises a single domain, and as defined herein refers to positions 108-214 of Cκ or Cλ, wherein numbering is according to the EU index.

Specifically included within the definition of "antibody" are full-length antibodies. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

Alternatively, the antibodies can be a variety of structures, including, but not limited to antibody fragments. Antibody fragments include but are not limited to bispecific antibodies, minibodies, domain antibodies, synthetic antibodies, antibody mimetics, chimeric antibodies, antibody fusions (sometimes referred to as "antibody conjugates"), and fragments of each, respectively. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable region, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (viii) bispecific single chain Fv dimers and (ix) "diabodies" or "triabodies", multivalent or multispecific fragments constructed by gene fusion. The antibody fragments may be modified. For example, the molecules may be stabilized by the incorporation of disulfide bridges linking the VH and VL domains. Examples of antibody formats and architectures are described in Holliger & Hudson, 2006, Nature Biotechnology 23(9): 1126-1136, and Carter 2006, Nature Reviews Immunology 6:343-357 and references cited therein, all expressly incorporated by reference.

Antibodies of the invention may include multispecific antibodies, notably bispecific antibodies, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

In one embodiment, the antibody of the invention is an antibody fragment. Of particular interest are antibodies that comprise Fc regions, Fc fusions, and the constant region of the heavy chain (CH1-hinge-CH2-CH3). Antibodies of the present invention may comprise Fc fragments. An Fc fragment of the present invention may comprise from 1-90% of the Fc region, e.g., 10-90%, 30-90%, etc. Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contain extra polypeptide sequence.

Chimeric, Humanized, and Fully Human Antibodies

Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. Thus in one embodiment, protein engineering is used to reduce the immunogenicity of the antibodies of the present invention.

In some embodiments, the scaffold components can be a mixture from different species. Such antibody may be a chimeric antibody and/or a humanized antibody. In general, both "chimeric antibodies" and "humanized antibodies" refer to antibodies that combine regions from more than one species. "Chimeric antibodies" traditionally comprise variable region(s) from a mouse (or rat, in some cases) and the constant region(s) from a human (Morrison et al., 1984, *Proc Natl Acad Sci USA* 81: 6851-6855, incorporated herein it its entirety by reference).

By "humanized" antibody as used herein is meant an antibody comprising a human framework region (FR) and one or more complementarity determining regions (CDRs) from a non-human (usually mouse or rat) antibody. The non-human antibody providing the CDRs is called the "donor" and the human immunoglobulin providing the framework is called the "acceptor". Humanization relies principally on the grafting of donor CDRs onto acceptor (human) VL and VH frameworks (Winter U.S. Pat. No. 5,225,539, incorporated herein it its entirety by reference). This strategy is referred to as "CDR grafting". "Backmutation" of selected acceptor framework residues to the corresponding donor residues is often required to regain affinity that is lost in the initial grafted construct (U.S. Pat. No. 5,693,762, incorporated herein it its entirety by reference). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, each incorporated herein it its entirety by reference). Humanization or other methods of reducing the immunogenicity of nonhuman antibody variable regions may include resurfacing methods, as described for example in Roguska et al., 1994, Proc. Natl. Acad. Sci. USA 91:969-973, incorporated herein it its entirety by reference. In one embodiment, selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084, incorporated herein it its entirety by reference. Structure-based methods may be employed for humanization and affinity maturation, for example as described in U.S. Ser. No. 10/153,159 and related applications, each incorporated herein it its entirety by reference.

In certain variations, the immunogenicity of the antibody is reduced using a method described in U.S. Ser. No. 11/004, 590, entitled "Methods of Generating Variant Proteins with Increased Host String Content and Compositions Thereof", filed on Dec. 3, 2004, incorporated herein it its entirety by reference.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody of the present invention. See for example U.S. Ser. No. 09/903,378, U.S. Ser. No. 10/754,296, U.S. Ser. No. 11/249,692, and references cited therein, all expressly incorporated by reference.

In an alternate embodiment, the antibodies of the present invention may be fully human, that is the sequences of the antibodies are completely or substantially human. "Fully human antibody" or "complete human antibody" refers to a human antibody having the gene sequence of an antibody derived from a human chromosome with the modifications outlined herein. A number of methods are known in the art for generating fully human antibodies, including the use of transgenic mice (Bruggemann et al., 1997, *Curr Opin Biotechnol* 8:455-458,) or human antibody libraries coupled with selection methods (Griffiths et al., 1998, *Curr Opin Biotechnol* 9:102-108), each incorporated herein it its entirety by reference.

Antibodies that Target CD40

The antibodies of the present invention may be virtually any antibody that binds to CD40, e.g., may comprise the variable regions (e.g., the CDRs) of any known or undiscovered anti-CD40 antibody. Antibodies of the invention may display selectivity for CD40. Examples include full-length versus splice variants, cell-surface vs. soluble forms, selectivity for various polymorphic variants, or selectivity for specific conformational forms of a target. An antibody of the present invention may bind any epitope or region on CD40 and may be specific for fragments, mutant forms, splice forms, or aberrant forms of the antigens. A number of useful antibodies have been discovered that target CD40 that may find use in the present invention.

Suitable CD40 antibodies or immunoadhesins include the CD40 antibodies or immunoadhesins S2C6 (Paulie et al., Cancer Immunol. Immunother., Vol 17, No 3, (1984) pp. 173-179), SGN-14 (chimeric S2C6; U.S. Pat. No. 6,843,989), CHIR-12.12 (US Pub. No. 2007/0218060, filed Nov. 4, 2004), 5D12 (U.S. Pat. No. 5,874,082; de Boer M. et al., 1992. J Immunol Methods. 152:15-23), 3A8 (ATCC cat#HB-12024-hybridoma), and G28-5 (ATCC cat#HB-9110 hybridoma; Clark E. A. et al., 1988. Eur J Immunol. 18:451-457).

The antibodies of the present invention may find use in a wide range of products. In one embodiment the antibody of the invention is a therapeutic, a diagnostic, or a research reagent. In one embodiment, an antibody of the invention is a therapeutic. Alternatively, the antibody of the present invention may be used for agricultural or industrial uses. An antibody of the present invention may find use in an antibody composition that is monoclonal or polyclonal. The antibodies of the present invention may be agonists, antagonists, neutralizing, inhibitory, or stimulatory. In one embodiment, the antibodies of the present invention are used to kill target cells that bear the target antigen, for example cancer cells. In an alternate embodiment, the antibodies of the present invention are used to block, antagonize, or agonize the target antigen. In an alternate embodiment, the antibodies of the present invention are used to block, antagonize, or agonize the target antigen and kill the target cells that bear the target antigen.

It will be recognized that the sequences identified as S2C6 VH (H0-H4) and S2C6 VL (L0-L3) can be combined in any combination in an antibody. Further, these sequences may be independently modified by adding all or part of an Fc region or Fc variant as disclosed herein. The modified sequences can also be combined in any combination in an antibody.

Modifications for Optimizing Effector Function

The present invention is directed to antibodies comprising modifications, wherein the modifications alter affinity to one or more Fc receptors, and/or alter the ability of the antibody to mediate one or more effector functions. Modifications of the invention include amino acid modifications and glycoform modifications.

Amino Acid Modifications

As described in U.S. Ser. No. 11/124,620, filed May 5, 2005, entitled "Optimized Fc Variants", and incorporated herein it its entirety by reference, amino acid modifications at heavy chain constant region positions 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, allow modification of FcγR binding properties, effector function, and potentially clinical properties of antibodies.

In particular, variants that alter binding to one or more human Fc receptors may comprise an amino acid modification in the heavy chain constant region, as described herein, selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286Q, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

As described in U.S. Ser. No. 11/090,981, filed Mar. 24, 2005, entitled "Immunoglobulin variants outside the Fc region", and incorporated herein it its entirety by reference, amino acid modifications at heavy chain constant region positions 118, 119, 120, 121, 122, 124, 126, 129, 131, 132, 133, 135, 136, 137, 138, 139, 147, 148, 150, 151, 152, 153, 155, 157, 159, 160, 161, 162, 163, 164, 165, 166, 167, 168, 169, 171, 172, 173, 174, 175, 176, 177, 178, 179, 180, 183, 187, 188, 189, 190, 191, 192, 193, 194, 195, 196, 197, 198, 199, 201, 203, 205, 206, 207, 208, 209, 210, 211, 212, 213, 214, 216, 217, 218, 219, 221, 222, 223, 224, 225, 226, 227, 228, 229, 230, 231, 232, 233, 234, 235, and 236, allow modification of FcγR binding properties, effector function, and potentially clinical properties of antibodies.

As described in U.S. Ser. No. 11/090,981, filed Mar. 24, 2005, entitled "Immunoglobulin variants outside the Fc region", and incorporated herein it its entirety by reference, amino acid modifications at light chain constant region positions 108, 109, 110, 111, 112, 114, 116, 121, 122, 123, 124, 125, 126, 127, 128, 129, 131, 137, 138, 140, 141, 142, 143, 145, 147, 149, 150, 151, 152, 153, 154, 155, 156, 157, 159, 160, 161, 162, 163, 164, 165, 166, 167, 168, 169, 170, 171, 172, 173, 174, 176, 180, 181, 182, 183, 184, 185, 187, 188, 189, 190, 191, 193, 195, 197, 199, 200, 202, 203, 204, 205, 206, 207, 208, 210, 211, 212, 213, allow modification of FcγR binding properties, effector function, and potentially clinical properties of antibodies.

In particular, variants that alter binding to one or more human Fc receptors may comprise an amino acid modification in the heavy chain constant region, as described herein, selected from the group consisting of 118K, 118E, 118Y, 119R, 119E, 119Y, 120R, 120E, 120I, 121E, 121Y, 121H, 122E, 122R, 124K, 124E, 124Y, 126K, 126D, 129L, 129D, 131G, 131T, 132D, 132R, 132L, 133R, 133E, 133L, 135I, 135E, 135K, 136E, 136K, 136I, 137E, 138S, 138R, 138D, 139I, 139E, 139K, 147A, 147E, 148Y, 148K, 150L, 150K, 150E, 151A, 151D, 152L, 152K, 153L, 153D, 155E, 155K, 155I, 157E, 157K, 157Y, 159K, 159D, 159L, 160K, 160E, 160Y, 161D, 162D, 162K, 162Y, 163R, 164R, 164E, 164Y, 165D, 165R, 165Y, 166D, 167A, 168L, 169E, 171G, 171H, 172K, 172L, 172E, 173T, 173D, 174E, 174K, 174Y, 175D, 175L, 176D, 176R, 176L, 177R, 177E, 177Y, 178D, 179K, 179Y, 179E, 180K, 180L, 180E, 183T, 187I, 187K, 187E, 188I, 189D, 189G, 190I, 190K, 190E, 191D, 191R, 191Y, 192N, 192R, 192L, 193F, 193E, 194R, 194D, 195R, 195D, 195Y, 196K, 196D, 196L, 197R, 197E, 197Y, 198L, 199T, 199D, 199K, 201E, 201K, 201L, 203D, 203L, 203K, 205D, 205L, 206A, 206E, 207K, 207D, 208R, 208E, 208Y, 209E, 209K, 209Y, 210L, 210E, 210Y, 211R, 211E, 211Y, 212Q, 212K, 212H, 212L, 212Y, 213N, 213E, 213H, 213L, 213Y, 214N, 214E, 214H, 214L, 214Y, 216N, 216K, 216H, 216L, 216Y, 217D, 217H, 217A, 217V, 217G, 218D, 218E, 218Q, 218T, 218H, 218L, 218Y, 219D, 219E, 219Q, 219K, 219T, 219H, 219L, 219I, 219Y, 205A, 210A, 213A, 214A, 218A, 221K, 221Y, 221E, 221N, 221Q, 221R, 221S, 221T, 221H, 221A, 221V, 221L, 221I, 221F, 221M, 221W, 221P, 221G, 222E, 222Y, 222D, 222N, 222Q, 222R, 222S, 222T, 222H, 222V, 222L, 222I, 222F, 222M, 222W, 222P, 222G, 222A, 223D, 223N, 223Q, 223R, 223S, 223H, 223A, 223V, 223L, 223I, 223F, 223M, 223Y, 223W, 223P, 223G, 223E, 223K, 224D, 224N, 224Q, 224K, 224R, 224S, 224T, 224V, 224L, 224I, 224F, 224M, 224W, 224P, 224G, 224E, 224Y, 224A, 225D, 225N, 225Q, 225R, 225S, 225H, 225A, 225V, 225L, 225I, 225F, 225M, 225Y, 225P, 225G, 225E, 225K, 225W, 226S, 227E, 227K, 227Y, 227G, 227D, 227N, 227Q, 227R, 227S, 227T, 227H, 227A, 227V, 227L, 227I, 227F, 227M, 227W, 228K, 228Y, 228G, 228D, 228N, 228Q, 228R, 228T, 228H, 228A, 228V, 228L, 228I, 228F, 228M, 228W, 229S, 230A, 230E, 230Y, 230G, 230D, 230N, 230Q, 230K, 230R, 230S, 230T, 230H, 230V, 230L, 230I, 230F, 230M, 230W, 231K, 231P, 231D, 231N, 231Q, 231R, 231S, 231T, 231H, 231V, 231L, 231I, 231F, 231M, 231W, 232E, 232K, 232Y, 232G, 232D, 232N, 232Q, 232R, 232S, 232T, 232H, 232A, 232V, 232L, 232I, 232F, 232M, 232W, 233D, 233N, 233Q, 233R, 233S, 233T, 233H, 233A, 233V, 233L, 233I, 233F, 233M, 233Y, 233W, 233G, 234D, 234E, 234N, 234Q, 234T, 234H, 234Y, 234I, 234V, 234F, 234K, 234R, 234S, 234A, 234M, 234G, 235D, 235S, 235N, 235Q, 235T, 235H, 235Y, 235I, 235V, 235F, 235E, 235K, 235R, 235A, 235M, 235W, 235P, 235G, 236D, 236E, 236N, 236Q, 236K, 236R, 236S, 236T, 236H, 236A, 236V, 236L, 236I, 236F, 236M, 236Y, 236W, and 236P, wherein numbering is according to the EU index.

In particular, variants that alter binding to one or more human Fc receptors may comprise an amino acid modification in the light chain constant region, as described herein, selected from the group consisting of: 108D, 108I, 108Q, 109D, 109P, 109R, 110E, 110I, 110K, 111E, 111K, 111L, 112E, 112R, 112Y, 114D, 114I, 114K, 116T, 121D, 122R, 122S, 122Y, 123L, 123R, 124E, 125E, 125K, 126D, 126L, 126Q, 127A, 127D, 127K, 128N, 129E, 129I, 129K, 131T, 137K, 137S, 138D, 138K, 138L, 140E, 140H, 140K, 141E, 141K, 142D, 142G, 142L, 143A, 143L, 143R, 145D, 145T, 145Y, 147A, 147E, 147K, 149D, 149Y, 150A, 151I, 151K, 152L, 152R, 152S, 153D, 153H, 153S, 154E, 154R, 154V, 155E, 155I, 155K, 156A, 156D, 156R, 157N, 158D, 158L, 158R, 159E, 159K, 159L, 160K, 160V, 161K, 161L, 162T, 163E, 163K, 163T, 164Q, 165K, 165P, 165Y, 166E, 166M, 166S, 167K, 167L, 168K, 168Q, 168Y, 169D, 169H, 169S, 170I, 170N, 170R, 171A, 171N, 171V, 172E, 172I, 172K, 173K, 173L, 173Q, 174A, 176T, 180E, 180K, 180S, 181K, 182E, 182R, 182T, 183D, 183L, 183P, 184E, 184K, 184Y, 185I, 185Q, 185R, 187K, 187Y, 188E, 188S, 188Y, 189D, 189K, 189Y, 190E, 190L, 190R, 191E, 191R, 191S, 193E, 193K, 193S, 195I, 195K, 195Q, 197E, 197K, 197L, 199E, 199K, 199Y, 200S, 202D, 202R, 202Y, 203D, 203L, 203R, 204T, 205E, 205K, 206E, 206I, 206K, 207A, 207E, 207L, 208E, 208K, 208T, 210A, 210E, 210K, 211A, 211E, 211P, 212E, 212K, 212T, 213L, 213R, wherein numbering is according to the EU index.

Additional substitutions that may also be used in the present invention include other substitutions that modulate Fc receptor affinity, FcγR-mediated effector function, and/or complement mediated effector function include but are not limited to 298A, 298T, 326A, 326D, 326E, 326W, 326Y, 333A, 333S, 334L, and 334A (U.S. Pat. No. 6,737,056; Shields et al, Journal of Biological Chemistry, 2001, 276(9): 6591-6604; U.S. Pat. No. 6,528,624; Idusogie et al., 2001, J. Immunology 166:2571-2572), 247L, 255L, 270E, 392T, 396L, and 421K (U.S. Ser. No. 10/754,922; U.S. Ser. No. 10/902,588), and 280H, 280Q, and 280Y (U.S. Ser. No. 10/370,749), each incorporated herein it its entirety by reference.

In other embodiments, antibodies of the present invention may be combined with constant heavy chain variants that alter FcRn binding. These include modifications that modify FcRn affinity in a pH-specific manner. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. No. 10/822,300, U.S. Ser. No. 10/687,118, PCT/US2004/034440, U.S. Ser. No. 10/966,673, each incorporated herein it its entirety by reference), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. No. 11/429,793, U.S. Ser. No. 11/429,786, PCT/US2005/029511, U.S. Ser. No. 11/208,422, each incorporated herein it its entirety by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328, each incorporated herein it its entirety by reference), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. No. 11/274,065, U.S. Ser. No. 11/436,266, each incorporated herein it its entirety by reference) 204D, 284E, 285E, 286D, and 290E (PCT/US2004/037929 incorporated herein it its entirety by reference).

In some embodiments of the invention, antibodies may comprise isotypic modifications, that is modifications in a parent IgG to the amino acid type in an alternate IgG. For example as illustrated in FIG. 1, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions selected from the group consisting of: 274Q, 276K, 300F, 339T, 356E, 358M, 384S, 392N, 397M, 422I, 435R, and 436F. In other embodiments of the invention, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more modifications selected from the group consisting of 233E, 234L, 235L, −236G (referring to an insertion of a glycine at position 236), and 327A.

Means for Optimizing Effector Function

The present invention is directed to antibodies comprising means for altering affinity to one or more Fc receptors, and/or alter the ability of the antibody to mediate one or more effector functions. Means of the invention include amino acid modifications (e.g., positional means for optimizing effector function, substitutional means for optimizing effector function, etc.) and glycoform modifications (e.g., means for glycoform modifications).

Amino Acid Modifications

As described in U.S. Ser. No. 11/124,620, filed May 5, 2005, entitled "Optimized Fc Variants", and incorporated herein it its entirety by reference, positional means for optimizing effector function include but is not limited to, modification of an amino acid at one or more heavy chain constant region positions (e.g., at positions 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337) which allow modification of FcγR binding properties, effector function, and potentially clinical properties of antibodies.

In particular, substitutional means for optimizing effector functions, for altering binding to one or more human Fc receptors, include, but is not limited to, a substitution of an amino acid at one or more heavy chain constant region positions, e.g., one or more of the following amino acid substitutions in the heavy chain constant region positions: 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

As described in U.S. Ser. No. 11/090,981, filed Mar. 24, 2005, entitled "Immunoglobulin variants outside the Fc region", and incorporated herein it its entirety by reference, positional means for optimizing effector function include, but is not limited to, modification of an amino acid at one or more heavy chain constant region positions (e.g., at positions 118, 119, 120, 121, 122, 124, 126, 129, 131, 132, 133, 135, 136, 137, 138, 139, 147, 148, 150, 151, 152, 153, 155, 157, 159, 160, 161, 162, 163, 164, 165, 166, 167, 168, 169, 171, 172, 173, 174, 175, 176, 177, 178, 179, 180, 183, 187, 188, 189, 190, 191, 192, 193, 194, 195, 196, 197, 198, 199, 201, 203, 205, 206, 207, 208, 209, 210, 211, 212, 213, 214, 216, 217, 218, 219, 221, 222, 223, 224, 225, 226, 227, 228, 229, 230, 231, 232, 233, 234, 235, and 236) which allow modification of FcγR binding properties, effector function, and potentially clinical properties of antibodies.

As described in U.S. Ser. No. 11/090,981, filed Mar. 24, 2005, entitled "Immunoglobulin variants outside the Fc region", and incorporated herein it its entirety by reference, positional means for optimizing effector function, include but is not limited to, modification of an amino acid at one or more light chain constant region positions (e.g., at positions 108, 109, 110, 111, 112, 114, 116, 121, 122, 123, 124, 125, 126, 127, 128, 129, 131, 137, 138, 140, 141, 142, 143, 145, 147, 149, 150, 151, 152, 153, 154, 155, 156, 157, 159, 160, 161, 162, 163, 164, 165, 166, 167, 168, 169, 170, 171, 172, 173, 174, 176, 180, 181, 182, 183, 184, 185, 187, 188, 189, 190, 191, 193, 195, 197, 199, 200, 202, 203, 204, 205, 206, 207, 208, 210, 211, 212, 213) which allow modification of FcγR binding properties, effector function, and potentially clinical properties of antibodies.

In particular, substitutional means for altering binding to one or more human Fc receptors include, but is not limited to, a substitution of an amino acid at one or more heavy chain constant region positions, e.g., one or more of the following substitutions: 118K, 118E, 118Y, 119R, 119E, 119Y, 120R, 120E, 120I, 121E, 121Y, 121H, 122E, 122R, 124K, 124E, 124Y, 126K, 126D, 129L, 129D, 131G, 131T, 132D, 132R, 132L, 133R, 133E, 133L, 135I, 135E, 135K, 136E, 136K, 136I, 137E, 138S, 138R, 138D, 139I, 139E, 139K, 147A, 147E, 148Y, 148K, 150L, 150K, 150E, 151A, 151D, 152L, 152K, 153L, 153D, 155E, 155K, 155I, 157E, 157K, 157Y, 159K, 159D, 159L, 160K, 160E, 160Y, 161D, 162D, 162K, 162Y, 163R, 164R, 164E, 164Y, 165D, 165R, 165Y, 166D, 167A, 168L, 169E, 171G, 171H, 172K, 172L, 172E, 173T, 173D, 174E, 174K, 174Y, 175D, 175L, 176D, 176R, 176L, 177R, 177E, 177Y, 178D, 179K, 179Y, 179E, 180K, 180L, 180E, 183T, 187I, 187K, 187E, 188I, 189D, 189G, 190I, 190K, 190E, 191D, 191R, 191Y, 192N, 192R, 192L, 193F, 193E, 194R, 194D, 195R, 195D, 195Y, 196K, 196D, 196L, 197R, 197E, 197Y, 198L, 199T, 199D, 199K, 201E, 201K, 201L, 203D, 203L, 203K, 205D, 205L, 206A, 206E, 207K, 207D, 208R, 208E, 208Y, 209E, 209K, 209Y, 210L, 210E, 210Y, 211R, 211E, 211Y, 212Q, 212K, 212H, 212L, 212Y, 213N, 213E, 213H, 213L, 213Y, 214N, 214E, 214H, 214L, 214Y, 216N, 216K, 216H, 216L, 216Y, 217D, 217H, 217A, 217V, 217G, 218D, 218E, 218Q, 218T, 218H, 218L, 218Y, 219D, 219E, 219Q, 219K, 219T, 219H, 219L, 219I, 219Y, 205A, 210A, 213A, 214A, 218A, 221K, 221Y, 221E, 221N, 221Q, 221R, 221S, 221T, 221H, 221A, 221V, 221L, 221I, 221F, 221M, 221W, 221P, 221G, 222E, 222Y, 222D, 222N, 222Q, 222R, 222S, 222T, 222H, 222V, 222L, 222I, 222F, 222M, 222W, 222P, 222G, 222A, 223D, 223N, 223Q, 223R, 223S, 223H, 223A, 223V, 223L, 223I, 223F, 223M, 223Y, 223W, 223P, 223G, 223E, 223K, 224D, 224N, 224Q, 224K, 224R, 224S, 224T, 224V, 224L, 224I, 224F, 224M, 224W, 224P, 224G, 224E, 224Y, 224A, 225D, 225N, 225Q, 225R, 225S, 225H, 225A, 225V, 225L, 225I, 225F, 225M, 225Y, 225P, 225G, 225E, 225K, 225W, 226S, 227E, 227K, 227Y, 227G, 227D, 227N, 227Q, 227R, 227S, 227T, 227H, 227A, 227V, 227L, 227I, 227F, 227M, 227W, 228K, 228Y, 228G, 228D, 228N, 228Q, 228R, 228T, 228H, 228A, 228V, 228L, 228I, 228F, 228M, 228W, 229S, 230A, 230E, 230Y, 230G, 230D, 230N, 230Q, 230K, 230R, 230S, 230T, 230H, 230V, 230L, 230I, 230F, 230M, 230W, 231K, 231P, 231D, 231N, 231Q, 231R, 231S, 231T, 231H, 231V, 231L, 231I, 231F, 231M, 231W, 232E, 232K, 232Y, 232G, 232D, 232N, 232Q, 232R, 232S, 232T, 232H, 232A, 232V, 232L, 232I, 232F, 232M, 232W, 233D, 233N, 233Q, 233R, 233S, 233T, 233H, 233A, 233V, 233L, 233I, 233F, 233M, 233Y, 233W, 233G, 234D, 234E, 234N, 234Q, 234T, 234H, 234Y, 234I, 234V, 234F, 234K, 234R, 234S, 234A, 234M, 234G, 235D, 235S, 235N, 235Q, 235T, 235H, 235Y, 235I, 235V, 235F, 235E, 235K, 235R, 235A, 235M, 235W, 235P, 235G, 236D, 236E, 236N, 236Q, 236K, 236R, 236S, 236T, 236H, 236A, 236V, 236L, 236I, 236F, 236M, 236Y, 236W, and 236P, wherein numbering is according to the EU index.

In particular, substitutional means for altering binding to one or more human Fc receptors include, but is not limited to, a substitution of an amino acid modification at one or more light chain constant region positions, e.g., one or more of the following amino acid substitutions in the light chain constant region positions: 108D, 108I, 108Q, 109D, 109P, 109R, 110E, 110I, 110K, 111E, 111K, 111L, 112E, 112R, 112Y, 114D, 114I, 114K, 116T, 121D, 122R, 122S, 122Y, 123L, 123R, 124E, 125E, 125K, 126D, 126L, 126Q, 127A, 127D, 127K, 128N, 129E, 129I, 129K, 131T, 137K, 137S, 138D, 138K, 138L, 140E, 140H, 140K, 141E, 141K, 142D, 142G, 142L, 143A, 143L, 143R, 145D, 145T, 145Y, 147A, 147E, 147K, 149D, 149Y, 150A, 151I, 151K, 152L, 152R, 152S, 153D, 153H, 153S, 154E, 154R, 154V, 155E, 155I, 155L, 156A, 156D, 156R, 157N, 158D, 158L, 158R, 159E, 159K, 159L, 160K, 160V, 161K, 161L, 162T, 163E, 163K, 163T, 164Q, 165K, 165P, 165Y, 166E, 166M, 166S, 167K, 167L, 168K, 168Q, 168Y, 169D, 169H, 169S, 170I, 170N, 170R, 171A, 171N, 171V, 172E, 172I, 172K, 173K, 173L, 173Q, 174A, 176T, 180E, 180K, 180S, 181K, 182E, 182R, 182T, 183D, 183L, 183P, 184E, 184K, 184Y, 185I, 185Q, 185R, 187K, 187Y, 188E, 188S, 188Y, 189D, 189K, 189Y, 190E, 190L, 190R, 191E, 191R, 191S, 193E, 193K, 193S, 195I, 195K, 195Q, 197E, 197K, 197L, 199E, 199K, 199Y, 200S, 202D, 202R, 202Y, 203D, 203L, 203R, 204T, 205E, 205K, 206E, 206I, 206K, 207A, 207E, 207L, 208E, 208K, 208T, 210A, 210E, 210K, 211A, 211E, 211P, 212E, 212K, 212T, 213L, 213R, wherein numbering is according to the EU index.

Additional substitutional means that may also be used in the present invention include substitutional means for modulating Fc receptor affinity, FcγR-mediated effector function, and/or complement mediated effector function, e.g., one or more of the following amino acid substitutions: 298A, 298T, 326A, 326D, 326E, 326W, 326Y, 333A, 333S, 334L, and 334A (U.S. Pat. No. 6,737,056; Shields et al, Journal of Biological Chemistry, 2001, 276(9):6591-6604; U.S. Pat. No. 6,528,624; Idusogie et al., 2001, J. Immunology 166:2571-2572), 247L, 255L, 270E, 392T, 396L, and 421K (U.S. Ser. No. 10/754,922; U.S. Ser. No. 10/902,588), and 280H, 280Q, and 280Y (U.S. Ser. No. 10/370,749), each incorporated herein it its entirety by reference.

In other embodiments, antibodies of the present invention may be combined with means for altering FcRn binding, e.g., antibodies of the present invention may be combined with constant heavy chain variants. These include means for modifying FcRn affinity in a pH-specific manner. In particular, substitutional means for increasing Fc binding to FcRn include, but are not limited to, one or more of the following amino acid substitutions: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. No. 10/822,300, U.S. Ser. No. 10/687,118, PCT/US2004/034440, U.S. Ser. No. 10/966,673, each incorporated herein it its entirety by reference), 256A, 272A, 286A, 305A, 0 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. No. 11/429,793, U.S. Ser. No. 11/429,786, PCT/US2005/029511, U.S. Ser. No. 11/208,422, each incorporated herein it its entirety by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169: 5171-5180, U.S. Pat. No. 7,083,784, PCT/US97/03321, U.S. Pat. No. 6,821,505, PCT/US01/48432, U.S. Ser. No. 11/397,328, each incorporated herein it its entirety by reference), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. No. 11/274,065, U.S. Ser. No. 11/436,266, each incorporated herein it its entirety by reference) 204D, 284E, 285E, 286D, and 290E (PCT/US2004/037929 incorporated herein it its entirety by reference).

In some embodiments of the invention, antibodies may comprise means for isotypic modifications, that is modifications in a parent IgG to the amino acid type in an alternate IgG. For example as illustrated in FIG. 1, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, -236G (referring to an insertion of a glycine at position 236), and 327A.

Glycoform Modifications

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation. (Lifely et al., 1995, Glycobiology 5(8): 813-822), incorporated herein it its entirety by reference.

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32, each incorporated herein it its entirety by reference). For human IgG, the core oligosaccharide normally consists of $GlcNAc_2Man_3GlcNAc$, with differing numbers of outer residues.

The carbohydrate moieties of the present invention will be described with reference to commonly used nomenclature for the description of oligosaccharides. A review of carbohydrate chemistry which uses this nomenclature is found in Hubbard et al. 1981, Ann. Rev. Biochem. 50:555-583, incorporated herein it its entirety by reference. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" is the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of the present invention occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991, incorporated herein it its entirety by reference).

For the purposes herein, a "mature core carbohydrate structure" refers to a processed core carbohydrate structure attached to an Fc region which generally consists of the following carbohydrate structure $GlcNAc(Fucose)-GlcNAc-Man-(Man-GlcNAc)_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

The present invention contemplates antibodies that comprise modified glycoforms or engineered glycoforms. By "modified glycoform" or "engineered glycoform" as used herein is meant a carbohydrate composition that is covalently attached to a protein, for example an antibody, wherein the carbohydrate composition differs chemically from that of a parent protein. Engineered glycoforms may be useful for a variety of purposes, including but not limited to enhancing or reducing FcγR-mediated effector function. In one embodiment, the antibodies of the present invention are modified to control the level of fucosylated and/or bisecting oligosaccharides that are covalently attached to the Fc region.

Historically, antibodies produced in Chinese Hamster Ovary Cells (CHO), one of the most commonly used industrial hosts, contain about 2 to 6% in the population that are nonfucosylated. YB2/0 (rat myeloma) and Lec13 cell line (a lectin mutant of CHO line which has a deficient GDP-mannose 4,6 dehydratase leading to the deficiency of GDP-fucose or GDP-sugar intermediates that are the substrate of α1,6-fucosyltransferase (Ripka et al., 1986), however, can produce antibodies with 78% to 98% nonfucosylated species. Unfortunately, the yield of antibody from these cells is extremely poor and therefore these cell lines are not useful to make therapeutic antibody products commercially. The FUT8 gene encodes the α1,6-fucosyltransferase enzyme that catalyzes the transfer of a fucosyl residue from GDP-fucose to position 6 of Asn-linked (N-linked) GlcNac of an N-glycan (Yanagidani et al., 1997, J Biochem 121:626-632). It is known that the α1,6-fucosyltransferase is the only enzyme responsible for adding fucose to the N-linked biantennary carbohydrate at Asn297 in the CH2 domain of the IgG antibody.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); Yamane-Ohnuki et al., 2004, Biotechnology and Bioengineering 87(5):614-621; (Potelligent™ technology [Biowa, Inc., Princeton, N.J.]; GlycoMAb™ glycosylation engineering technology [GLYCART biotechnology AG, Zurich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed.

Other methods for modifying glycoforms of the antibodies of the invention include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). Methods for modifying glycoforms include but are not limited to using a glycoengineered strain of yeast *Pichia pastoris* (Li et al., 2006, Nature Biotechnology 24(2):210-215), a glycoengineered strain of the moss *Physcomitrella patens* wherein the enzymes β1,2-xylosyltransferase and/or α1,3-fucosyltransferase are knocked out in (Nechansky et al., 2007, Mol. Immunol. 44(7):1826-8), and the use of RNA interference to inhibit endogenous alpha-1,3-fucosyltransferase and/or beta-1,2-xylosyltransferase in the aquatic plant Lemna minor (Cox et al., 2006, Nat. Biotechnol. 24(12): 1591-7).

Engineered glycoform typically refers to the different carbohydrate or oligosaccharide; thus for example an antibody may comprise an engineered glycoform. Alternatively, engineered glycoform may refer to the antibody that comprises the different carbohydrate or oligosaccharide. For the purposes of modified glycoforms described herein, a "parent antibody" is a glycosylated antibody having the same amino acid sequence and mature core carbohydrate structure as an engineered glycoform of the present invention, except that fucose is attached to the mature core carbohydrate structure of the parent antibody. For instance, in a composition comprising the parent glycoprotein about 50-100% or about 70-100% of the parent glycoprotein comprises a mature core carbohydrate structure having fucose attached thereto.

The present invention provides a composition comprising a glycosylated antibody having an Fc region, wherein about 51-100% of the glycosylated antibody in the composition comprises a mature core carbohydrate structure which lacks fucose, attached to the Fc region of the antibody. In one embodiment, about 80-100% of the antibody in the composition comprises a mature core carbohydrate structure which lacks fucose. In another embodiment about 90-99% of the antibody in the composition lacks fucose attached to the mature core carbohydrate structure. In another embodiment, the antibody in the composition both comprises a mature core carbohydrate structure that lacks fucose and additionally comprises at least one amino acid modification in the Fc region. In another embodiment, the combination of engineered glycoform and amino acid modification provides optimal Fc receptor binding properties to the anti-CD40 antibody.

Optimized Properties of Antibodies

The present invention provides variant antibodies that are optimized for a number of therapeutically relevant properties. A variant antibody comprises one or more amino acid modifications or glycoform modifications relative to a parent antibody, wherein the amino acid modification(s) provide one or more optimized properties. Thus the antibodies of the present invention are variant antibodies. An antibody of the present invention differs in amino acid sequence from its parent antibody by virtue of at least one amino acid or glycoform modification. Thus variant antibodies of the present invention have at least one amino acid or glycoform modification compared to the parent. Alternatively, the variant antibodies of the present invention may have more than one amino acid modification as compared to the parent, for example from about one to fifty amino acid modifications, e.g., from about one to ten amino acid modifications, from about one to about five amino acid modifications, etc., compared to the parent. Thus the sequences of the variant antibodies and those of the parent antibodies are substantially homologous. For example, the variant antibody sequences herein will possess about 80% homology with the parent antibody sequence, e.g., at least about 90% homology, e at least about 95% homology, etc.

In another embodiment, the antibodies of the present invention comprise amino acid modifications that provide optimized effector function properties relative to the parent. Substitutions and optimized effector function properties are described in U.S. Ser. No. 10/672,280, PCT US03/30249, and U.S. Ser. No. 10/822,231, and U.S. Ser. No. 60/627,774, filed Nov. 12/2004 and entitled "Optimized Fc Variants". Properties that may be optimized include but are not limited to enhanced or reduced affinity for an FcγR. In one embodiment, the antibodies of the present invention are optimized to possess enhanced affinity for a human activating FcγR, e.g., FcγRI, FcγRIIa, FcγRIIc, FcγRIIIa, and FcγRIIIb. In one embodiment, an antibody of the invention are optimized to possess enhanced affinity for a human FcγRIIIa. In an alternate embodiment, the antibodies are optimized to possess reduced affinity for the human inhibitory receptor FcγRIIb. These embodiments are anticipated to provide antibodies with enhanced therapeutic properties in humans, for example enhanced effector function and greater anti-cancer potency. In an alternate embodiment, the antibodies of the present invention are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide antibodies with enhanced therapeutic properties in humans, for example reduced effector function and reduced toxicity. In other embodiments, antibodies of the present invention provide enhanced affinity for one or more FcγRs, yet reduced affinity for one or more other FcγRs. For example, an antibody of the present invention may have enhanced binding to FcγRIIIa, yet reduced binding to FcγRIIb. Alternately, an antibody of the present invention may have enhanced binding to FcγRIIa and FcγRI, yet reduced binding to FcγRIIb. In yet another embodiment, an antibody of the present invention may have enhanced affinity for FcγRIIb, yet reduced affinity to one or more activating FcγRs.

The modifications of the invention may enhance binding affinity for one or more FcγRs. By "greater affinity" or "improved affinity" or "enhanced affinity" or "better affinity" than a parent immunoglobulin, as used herein is meant that an Fc variant binds to an Fc receptor with a significantly higher equilibrium constant of association ($K_a$) or lower equilibrium constant of dissociation ($K_d$) than the parent polypeptide when the amounts of variant and parent polypeptide in the binding assay are essentially the same. For example, the Fc variant with improved FcγR binding affinity may display from about 5 fold to about 1000 fold, e.g. from about 10 fold to about 500 fold improvement in Fc receptor binding affinity compared to the parent polypeptide, where Fc receptor binding affinity is determined, for example, as disclosed in the Examples herein. Accordingly, by "reduced affinity" as compared to a parent Fc polypeptide as used herein is meant that an Fc variant binds an Fc receptor with significantly lower $K_a$ or higher $K_d$ than the parent polypeptide.

Embodiments comprise optimization of Fc binding to a human FcγR, however in alternate embodiments the antibodies of the present invention possess enhanced or reduced affinity for FcγRs from nonhuman organisms, including but not limited to rodents and non-human primates. Antibodies that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies that comprise antibodies that are optimized for one or more mouse FcγRs, may provide valuable information with regard to the efficacy of the protein, its mechanism of action, and the like. The antibodies of the present invention may also be optimized for enhanced functionality and/or solution properties in aglycosylated form. In one embodiment, the aglycosylated antibodies of the present invention bind an Fc ligand with greater affinity than the aglycosylated form of the parent antibody. The Fc ligands include but are not limited to FcγRs, C1q, FcRn, and proteins A and G, and may be from any source including but not limited to human, mouse, rat, rabbit, or monkey. In an alternate embodiment, the antibodies are optimized to be more stable and/or more soluble than the aglycosylated form of the parent antibody.

Antibodies of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136, incorporated herein it its entirety by reference).

In one embodiment, the Fc ligand specificity of the antibody of the present invention will determine its therapeutic utility. The utility of a given antibody for therapeutic purposes will depend on the epitope or form of the target antigen and the disease or indication being treated. For some targets and indications, enhanced FcγR-mediated effector functions may be desirable. This may be particularly favorable for anti-cancer antibodies. Thus antibodies may be used that comprise antibodies that provide enhanced affinity for activating FcγRs and/or reduced affinity for inhibitory FcγRs. For some targets and indications, it may be further beneficial to utilize antibodies that provide differential selectivity for different activating FcγRs; for example, in some cases enhanced binding to FcγRIIa and FcγRIIIa may be desired, but not FcγRI, whereas in other cases, enhanced binding only to FcγRIIa may be desired. For certain targets and indications, it may be desirable to utilize antibodies that enhance both FcγR-mediated and complement-mediated effector functions, whereas for other cases it may be advantageous to utilize antibodies that enhance either FcγR-mediated or complement-mediated effector functions. For some targets or cancer indications, it may be advantageous to reduce or ablate one or more effector functions, for example by knocking out binding to C1q, one or more FcγR's, FcRn, or one or more other Fc ligands. For other targets and indications, it may be desirable to utilize antibodies that provide enhanced binding to the inhibitory FcγRIIb, WT level, reduced, or ablated binding to activating FcγRs. This may be particularly useful, for example, when the goal of an antibody is to inhibit inflammation or auto-immune disease, or modulate the immune system in some way.

Clearly an important parameter that determines the most beneficial selectivity of a given antibody to treat a given disease is the context of the antibody, that is what type of antibody is being used. Thus the Fc ligand selectivity or specificity of a given antibody will provide different properties depending on whether it composes an antibody or an antibodies with a coupled fusion or conjugate partner. For example, toxin, radionucleotide, or other conjugates may be less toxic to normal cells if the antibody that comprises them has reduced or ablated binding to one or more Fc ligands. As another example, in order to inhibit inflammation or auto-immune disease, it may be desirable to utilize an antibody with enhanced affinity for activating FcγRs, such as to bind these FcγRs and prevent their activation. Conversely, an antibody that comprises two or more Fc regions with enhanced FcγRIIb affinity may co-engage this receptor on the surface of immune cells, thereby inhibiting proliferation of these cells. Whereas in some cases an antibodies may engage its target antigen on one cell type yet engage FcγRs on separate cells from the target antigen, in other cases it may be advantageous to engage FcγRs on the surface of the same cells as the target antigen. For example, if an antibody targets an antigen on a cell that also expresses one or more FcγRs, it may be beneficial to utilize an antibody that enhances or reduces binding to the FcγRs on the surface of that cell. This may be the case, for example when the antibody is being used as an anti-cancer agent, and co-engagement of target antigen and FcγR on the surface of the same cell promote signaling events within the cell that result in growth inhibition, apoptosis, or other anti-proliferative effect. Alternatively, antigen and FcγR co-engagement on the same cell may be advantageous when the antibody is being used to modulate the immune system in some way, wherein co-engagement of target antigen and FcγR provides some proliferative or anti-proliferative effect. Likewise, antibodies that comprise two or more Fc regions may benefit from antibodies that modulate FcγR selectivity or specificity to co-engage FcγRs on the surface of the same cell.

The Fc ligand specificity of the antibodies of the present invention can be modulated to create different effector function profiles that may be suited for particular antigen epitopes, indications or patient populations. FIG. 3 describes several embodiments of receptor binding profiles that include improvements to, reductions to or no effect to the binding to various receptors, where such changes may be beneficial in certain contexts. The receptor binding profiles in the figure could be varied by degree of increase or decrease to the specified receptors. Additionally, the binding changes specified could be in the context of additional binding changes to other receptors such as C1q or FcRn, for example by combining with ablation of binding to C1q to shut off complement activation, or by combining with enhanced binding to C1q to increase complement activation. Other embodiments with other receptor binding profiles are possible, the listed receptor binding profiles are exemplary.

The presence of different polymorphic forms of FcγRs provides yet another parameter that impacts the therapeutic utility of the antibodies of the present invention. Whereas the specificity and selectivity of a given antibody for the different classes of FcγRs significantly affects the capacity of an antibody to target a given antigen for treatment of a given disease, the specificity or selectivity of an antibody for different polymorphic forms of these receptors may in part determine which research or pre-clinical experiments may be appropriate for testing, and ultimately which patient populations may or may not respond to treatment. Thus the specificity or selectivity of antibodies of the present invention to Fc ligand polymorphisms, including but not limited to FcγR, C1q, FcRn, and FcRH polymorphisms, may be used to guide the selection of valid research and pre-clinical experiments, clinical trial design, patient selection, dosing dependence, and/or other aspects concerning clinical trials.

Other Modifications

Antibodies of the present invention may comprise one or more modifications that provide optimized properties that are not specifically related to effector function per se. The modifications may be amino acid modifications, or may be modifications that are made enzymatically or chemically. Such modification(s) likely provide some improvement in the antibody, for example an enhancement in its stability, solubility, function, or clinical use. The present invention contemplates a variety of improvements that made be made by coupling the antibodies of the present invention with additional modifications.

In one embodiment, the variable region of an antibody of the present invention may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen.

Antibodies of the invention may comprise one or more modifications that provide reduced or enhanced internalization of an antibody. In one embodiment, antibodies of the present invention can be utilized or combined with additional modifications in order to reduce the cellular internalization of an antibody that occurs via interaction with one or more Fc ligands. This property might be expected to enhance effector function, and potentially reduce immunogenicity of the antibodies of the invention. Alternatively, antibodies of the present antibodies of the present invention can be utilized directly or combined with additional modifications in order to enhance the cellular internalization of an antibody that occurs via interaction with one or more Fc ligands. For example, in one embodiment, an antibody is used that provides enhanced binding to FcγRI, which is expressed on dendritic cells and active early in immune response. This strategy could be further enhanced by combination with additional modifications, either within the antibody or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, *Immunol Rev.* 172:279-84, incorporated herein it its entirety by reference), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In one embodiment, modifications are made to improve biophysical properties of the antibodies of the present invention, including but not limited to stability, solubility, and oligomeric state. Modifications can include, for example, substitutions that provide more favorable intramolecular interactions in the antibody such as to provide greater stability, or substitution of exposed nonpolar amino acids with polar amino acids for higher solubility. A number of optimization goals and methods are described in U.S. Ser. No. 10/379,392, incorporated herein it its entirety by reference, that may find use for engineering additional modifications to further optimize the antibodies of the present invention. The antibodies of the present invention can also be combined with additional modifications that reduce oligomeric state or size, such that tumor penetration is enhanced, or in vivo clearance rates are increased as desired.

Other modifications to the antibodies of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, J. Exp. Med. 176:1191-1195, and Shopes, 1992, J. Immunol. 148(9): 2918-22, each incorporated herein it its entirety by reference. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15, each incorporated herein it its entirety by reference. Additional modifications include modifications in the hinge and CH3 domains, in which the modifications reduce the propensity to form dimers.

In further embodiments, the antibodies of the present invention comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particularly useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated herein it its entirety by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The antibodies of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, each incorporated herein it its entirety by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the antibodies. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the antibodies of the present invention.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies of the invention comprises the addition of one or more labels. The term "labeling group" is any detectable label. In some embodiments, the labeling group is coupled to the antibody via spacer arms of various lengths to reduce potential steric hindrance. Various methods for labeling proteins are known in the art and may be used in performing the present invention. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in performing the present invention. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

Antibody Conjugates and Fusions

In one embodiment, the antibodies of the invention are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated herein it its entirety by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the antibody. Thus, for example, the conjugation of a toxin to an antibody targets the delivery of the toxin to cells expressing the target antigen. As will be appreciated by one skilled in the art, in reality the concepts and definitions of fusion and conjugate are overlapping. The designation of an antibody as a fusion or conjugate is not meant to constrain it to any particular embodiment of the present invention. Rather, these terms are used loosely to convey the broad concept that any antibody of the present invention may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, incorporated herein it its entirety by reference.

In one embodiment, the antibodies of the present invention are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated herein it its entirety by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the antibodies of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71, incorporated herein it its entirety by reference. Small molecule toxins include but are not limited to calicheamicin, maytansine (U.S. Pat. No. 5,208,020, incorporated herein it its entirety by reference), trichothene, and CC1065. In one embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, *Cancer Research* 52: 127-131, incorporated herein it its entirety by reference) to generate a maytansinoid-antibody conjugate. Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma l^1$, PSAG, and $\Theta^1_1$, (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773,001, each incorporated herein it its entirety by reference). Dolastatin 10 analogs such as auristatin E (AE) and monomethylauristatin E (MMAE) may find use as conjugates for the antibodies of the present invention (Doronina et al., 2003, Nat Biotechnol 21(7):778-84; Francisco et al., 2003 Blood 102(4):1458-65, each incorporated herein it its entirety by reference). Useful enzymatically active toxins include but are not limited to diphtheria A chain, nonbinding active fragments of diphtheria toxin, exotoxin A chain (from Pseudomonas aeruginosa), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, PCT WO 93/21232, incorporated herein it its entirety by reference. The present invention further contemplates a conjugate between an antibody of the present invention and a compound with nucleolytic activity, for example a ribonuclease or DNA endonuclease such as a deoxyribonuclease (Dnase).

In an alternate embodiment, an antibody of the present invention may be fused, conjugated, or operably linked to a radioisotope to form a radioconjugate. A variety of radioactive isotopes are available for the production of radioconjugate antibodies. Examples include, but are not limited to, At211, I131, I125, Y90, Re186, Re188, Sm153, Bi212, P32, and radioactive isotopes of Lu.

In yet another embodiment, an antibody of the present invention may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145, incorporated herein it its entirety by reference) to an active anti-cancer drug. See, for example, PCT WO 88/07378 and U.S. Pat. No. 4,975,278, each incorporated herein it its entirety by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, *Nature* 328: 457-458, incorporated herein it its entirety by reference). Antibody-abzyme conjugates can be prepared for delivery of the abzyme to a tumor cell population. A variety of additional conjugates are contemplated for the antibodies of the present invention. A variety of chemotherapeutic agents, anti-angiogenic agents, tyrosine kinase inhibitors, and other therapeutic agents are described below, which may find use as antibody conjugates.

Also contemplated as fusion and conjugate partners are Fc polypeptides. Thus an antibody may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab's and Fc's may be linked by thioether bonds originating at cysteine residues in the hinges, generating molecules such as $FabFc_2$. Fc regions may be linked using disulfide engineering and/or chemical cross-linking. In one embodiment, Fc regions may be linked genetically. In one embodiment, Fc regions in an antibody are linked genetically to generated tandemly linked Fc regions as described in U.S. Ser. No. 11/022,289, filed Dec. 21, 2004, entitled "Fc polypeptides with novel Fc ligand binding sites," incorporated herein it its entirety by reference. Tandemly linked Fc polypeptides may comprise two or more Fc regions, e.g., one to three, two, etc., Fc regions. It may be advantageous to explore a number of engineering constructs in order to obtain homo- or hetero-tandemly linked antibodies with the most favorable structural and functional properties. Tandemly linked antibodies may be homo-tandemly linked antibodies, that is an antibody of one isotype is fused genetically to another antibody of the same isotype. It is anticipated that because there are multiple FcγR, C1q, and/or FcRn binding sites on tandemly linked Fc polypeptides, effector functions and/or pharmacokinetics may be enhanced. In an alternate embodiment, antibodies from different isotypes may be tandemly linked, referred to as hetero-tandemly linked antibodies. For example, because of the capacity to target FcγR and FcαRI receptors, an antibody that binds both FcγRs and FcαRI may provide a significant clinical improvement.

In addition to antibodies, an antibody-like protein that is finding an expanding role in research and therapy is the Fc fusion (Chamow et al., 1996, *Trends Biotechnol* 14:52-60; Ashkenazi et al., 1997, *Curr Opin Immunol* 9:195-200, each incorporated herein it its entirety by reference). "Fc fusion" is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends also to Fc.

Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, e.g., an extracellular receptor, that is implicated in disease.

Fusion and conjugate partners may be linked to any region of an antibody of the present invention, including at the N- or C-termini, or at some residue in-between the termini. In one embodiment, a fusion or conjugate partner is linked at the N- or C-terminus of the antibody, e.g., the N-terminus. A variety of linkers may find use in the present invention to covalently link antibodies to a fusion or conjugate partner. By "linker", "linker sequence", "spacer", "tethering sequence" or grammatical equivalents thereof, herein is meant a molecule or group of molecules (such as a monomer or polymer) that connects two molecules and often serves to place the two molecules in a desirable configuration. Linkers are known in the art; for example, homo- or hetero-bifunctional linkers as are well known (see, 1994 Pierce Chemical Company catalog, technical section on cross-linkers, pages 155-200, incorporated herein it its entirety by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length, with linkers of 1 to 20 amino acids in length being desirable. Useful linkers include glycine-serine polymers (including, for example, (GS)n, (GSGGS)n (GGGGS)n and (GGGS)n, where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the antibodies of the present invention to a fusion or conjugate partner, or to link the antibodies of the present invention to a conjugate.

Production of Antibodies

The present invention provides methods for producing and experimentally testing antibodies. The described methods are not meant to constrain the present invention to any particular application or theory of operation. Rather, the provided methods are meant to illustrate generally that one or more antibodies may be produced and experimentally tested to obtain variant antibodies. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988, each incorporated herein it its entirety by reference.

In one embodiment of the present invention, nucleic acids are created that encode the antibodies, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons), each incorporated herein it its entirety by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries of the present invention. Such methods that may find use in the present invention are described or referenced in U.S. Pat. No. 6,403,312; U.S. Ser. No. 09/782,004; U.S. Ser. No. 09/927,790; U.S. Ser. No. 10/218,102; PCT WO 01/40091; and PCT WO 02/25588, each incorporated herein it its entirety by reference. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode antibodies.

The antibodies of the present invention may be produced by culturing a host cell transformed with nucleic acid, e.g., an expression vector, containing nucleic acid encoding the antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In one embodiment, the antibodies are expressed in mammalian expression systems, including systems in which the expression constructs are introduced into the mammalian cells using virus such as retrovirus or adenovirus. Any mammalian cells may be used, e.g., human, mouse, rat, hamster, primate cells, etc. Suitable cells also include known research cells, including but not limited to Jurkat T cells, NIH3T3, CHO, BHK, COS, HEK293, PER C.6, HeLa, Sp2/0, NSO cells and variants thereof. In an alternate embodiment, library proteins are expressed in bacterial cells. Bacterial expression systems are well known in the art, and include *Escherichia coli* (*E. coli*), *Bacillus subtilis*, *Streptococcus cremoris*, and *Streptococcus lividans*. In alternate embodiments, antibodies are produced in insect cells (e.g. Sf21/Sf9, *Trichoplusia ni* Bti-Tn5b1-4) or yeast cells (e.g. *S. cerevisiae, Pichia*, etc). In an alternate embodiment, antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used Antibodies may be operably linked to a fusion partner to enable targeting of the expressed protein, purification, screening, display, and the like. Fusion partners may be linked to the antibody sequence via a linker sequence. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an antibody may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen antibodies (see below). Fusion partners that enable a variety of selection methods are well-known in the art, and all of these find use in the present invention. For example, by fusing the members of an antibody library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated herein it its entirety by reference). Fusion partners may enable antibodies to be labeled. Alternatively, a fusion partner may bind to a specific sequence on the expression vector, enabling the fusion partner and associated antibody to be linked covalently or noncovalently with the nucleic acid that encodes them.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, antibodies are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. Protein Purification: Principles and Practice, $3^{rd}$ Ed., Scopes, Springer-Verlag, NY, 1994, incorporated herein it its entirety by reference. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins. Thus, for example, if a library of antibodies is made into a phage display library, protein purification may not be performed.

In Vitro Experimentation

Antibodies may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the antibodies of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of antibodies are screened in an in vitro assay. In vitro assays may allow a broad dynamic range for screening properties of interest. Properties of antibodies that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In one embodiment, the screen is a binding assay for measuring binding to the target antigen. In an alternate embodiment, the screen is an assay for binding of antibodies to an Fc ligand, including but not limited to the family of FcγRs, the neonatal receptor FcRn, the complement protein C1q, and the bacterial proteins A and G. The Fc ligands may be from any organism, e.g., humans, mice, rats, rabbits, monkeys, etc. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as Biacore™), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

The biophysical properties of antibodies, for example stability and solubility, may be screened using a variety of methods known in the art. Protein stability may be determined by measuring the thermodynamic equilibrium between folded and unfolded states. For example, antibodies of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use in the present invention for characterizing the biophysical properties of antibodies include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

In one embodiment, the library is screened using one or more cell-based or in vitro assays. For such assays, antibodies, purified or unpurified, are typically added exogenously such that cells are exposed to individual variants or groups of variants belonging to a library. These assays are typically, but not always, based on the biology of the ability of the antibody to bind to antigen and mediate some biochemical event, for example effector functions like cellular lysis, phagocytosis, ligand/receptor binding inhibition, inhibition of growth and/or proliferation, apoptosis, etc. Such assays often involve monitoring the response of cells to antibody, for example cell survival, cell death, cellular phagocytosis, cell lysis, change in cellular morphology, or transcriptional activation such as cellular expression of a natural gene or reporter gene. For example, such assays may measure the ability of antibodies to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rats, rabbits, monkeys, etc. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation, or activation to be monitored. In one embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies.

In vitro assays include but are not limited to binding assays, ADCC, CDC, phagocytosis, cytotoxicity, proliferation, apoptosis, necrosis, cell cycle arrest, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the antibodies of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. With respect to the antibodies of the present invention, a particular challenge arises when using animal models to evaluate the potential for in-human efficacy of candidate polypeptides—this is due, at least in part, to the fact that antibodies that have a specific effect on the affinity for a human Fc receptor may not have a similar affinity effect with the orthologous animal receptor. These problems can be further exacerbated by the inevitable ambiguities associated with correct assignment of true orthologs (Mechetina et al., *Immunogenetics,* 2002 54:463-468, incorporated herein it its entirety by reference), and the fact that some orthologs simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the antibody to reduce or inhibit cancer growth and metastasis. An alternative approach is the use of a SCID murine model in which immune-deficient mice are injected with human Periferal Blood Lymphocytes (PBLs), conferring a semi-functional and human immune system—with an appropriate array of human FcRs—to the mice that have subsequently been injected with antibodies or Fc-polypeptides that target injected human tumor cells. In such a model, the Fc-polypeptides that target the desired antigen (such as her2/neu on SkOV3 ovarian cancer cells) interact with human PBLs within the mice to engage tumoricidal effector functions. Such experimentation may provide meaningful data for determination of the potential of the antibody to be used as a therapeutic. Any organism, e.g., mammals, may be used for testing. For example because of their genetic similarity to humans, monkeys can be suitable therapeutic models, and thus may be used to test the efficacy, toxicity, pharmacokinetics, or other property of the antibodies of the present invention. Tests of the antibodies of the present invention in humans are ultimately required for approval as drugs, and thus of course these experiments are contemplated. Thus the antibodies of the present invention may be tested in humans to determine their therapeutic efficacy, toxicity, pharmacokinetics, and/or other clinical properties.

The antibodies of the present invention may confer superior performance on Fc-containing therapeutics in animal models or in humans. The receptor binding profiles of such antibodies, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an antibody with reduced binding to FcγRIIIa, FcγRI and FcγRIIa can be selected to eliminate most cell-mediated effector function, or an antibody with reduced binding to C1q may be selected to limit complement-mediated effector functions. In some contexts, such effector functions are known to have potential toxic effects, therefore eliminating them may increase the safety of the Fc-bearing drug and such improved safety may be characterized in animal models. In some contexts, such effector functions are known to mediate the desirable therapeutic activity, therefore enhancing them may increase the activity or potency of the Fc-bearing drug and such improved activity or potency may be characterized in animal models.

Optimized antibodies can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intraorgan (e.g. pancreas, prostate or mammary gland) injection of human tumor cells or fragments of donor patients.

In some embodiments, antibodies of the present invention may be assessed for efficacy in clinically relevant animal models of various human diseases. In many cases, relevant models include various transgenic animals for specific tumor antigens.

Relevant transgenic models such as those that express human Fc receptors (e.g., CD16 including the gamma chain, FcγR1, RIIa/b, and others) could be used to evaluate and test antibodies and Fc-fusions in their efficacy. The evaluation of antibodies by the introduction of human genes that directly or indirectly mediate effector function in mice or other rodents may enable physiological studies of efficacy in tumor toxicity or other diseases such as autoimmune disorders and RA. Human Fc receptors such as FcγRIIIa may possess polymorphisms such as that in position 158 V or F which would further enable the introduction of specific and combinations of human polymorphisms into rodents. The various studies involving polymorphism-specific FcRs are not limited to this section, however, and encompasses all discussions and applications of FcRs in general as specified in throughout this application. antibodies of the present invention may confer superior activity on Fc-containing drugs in such transgenic models, in particular variants with binding profiles optimized for human FcγRIIIa mediated activity may show superior activity in transgenic CD16 mice. Similar improvements in efficacy in mice transgenic for the other human Fc receptors, e.g. FcγRIIa, FcγRI, etc., may be observed for antibodies with binding profiles optimized for the respective receptors. Mice transgenic for multiple human receptors would show improved activity for antibodies with binding profiles optimized for the corresponding multiple receptors, for example as outlined in FIG. 3.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules may mimic—in the animal system—the FcR and/or complement biology of a corresponding candidate human antibody. This mimicry is most likely to be manifested by relative association affinities between specific antibodies and animal vs. human receptors. For example, if one were using a mouse model to assess the potential in-human efficacy of an antibody that has enhanced affinity for human FcγRIIIa, an appropriate proxy variant would have enhanced affinity for mouse FcγRIII-2 (mouse CD16-2). Alternatively if one were using a mouse model to assess the potential in-human efficacy of an antibody that has reduced affinity for the inhibitory human FcγRIIb, an appropriate proxy variant would have reduced affinity for mouse FcγRII. It should also be noted that the proxy antibodies could be created in the context of a human antibody, an animal antibody, or both.

In one embodiment, the testing of antibodies may include study of efficacy in primates (e.g. cynomolgus monkey model) to facilitate the evaluation of depletion of specific target cells harboring target antigen. Additional primate models include but are not limited to that of the rhesus monkey and Fc polypeptides in therapeutic studies of autoimmune, transplantation, and cancer.

Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity, and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the antibodies of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg)

can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life ($T_{1/2}$). Additional measured parameters could include compartmental analysis of concentration-time data obtained following i.v. administration and bioavailability. Examples of pharmacological/toxicological studies using cynomolgus have been established for Rituxan® and Zevalin® in which monoclonal antibodies to CD20 are cross-reactive. Biodistribution, dosimetry (for radiolabled antibodies), and PK studies can also be done in rodent models. Such studies would evaluate tolerance at all doses administered, toxicity to local tissues, localization to rodent xenograft animal models, depletion of target cells (e.g. CD20 positive cells).

The antibodies of the present invention may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of antibodies of the present invention. Because antibodies of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The antibodies of the present invention may target particular effector cell populations and thereby direct Fc-containing drugs to recruit certain activities to improve potency or to increase penetration into a particularly favorable physiological compartment. For example, neutrophil activity and localization can be targeted, e.g., by an antibody that targets FcγRIIIb. Such pharmacodynamic effects may be demonstrated in animal models or in humans.

Clinical Use

The antibodies of the present invention may be used for various therapeutic purposes. As will be appreciated by those in the art, the antibodies of the present invention may be used for any therapeutic purpose that uses antibodies and the like. In one embodiment, the antibodies are administered to a patient to treat disorders including but not limited to cancer, autoimmune and inflammatory diseases, and infectious diseases.

A "patient" for the purposes of the present invention includes both humans and other animals, e.g., mammals, e.g., humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an optimized antibody after clinical manifestation of the disease to combat the symptoms of the disease comprises treatment of the disease. "Treatment" and "treating" also encompasses administration of an optimized antibody after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an antibody of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and the measurement may play an important role in the development and/or clinical testing of the antibodies of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as non-Hodgkin's lymphomas (NHL). NHL cancers include but are not limited to Burkitt's lymphoma (BL), small lymphocytic lymphoma/chronic lymphocytic leukemia (SLL/CLL), mantle cell lymphoma (MCL), follicular lymphoma (FL), diffuse large B-cell lymphoma (DLCL), marginal zone lymphoma (MZL), hairy cell leukemia (HCL) and lymphoplasmacytic leukemia (LPL), extranodal marginal zone B-cell lymphoma of mucosa-associated lymphoid tissue (MALT), nodal marginal zone B cell lymphoma, mediastinal large cell lymphoma, intravascular large cell lymphoma, primary effusion lymphoma, precursor B-lymphoblastic leukemia/lymphoma, precursor T- and NK-cells lymphoma (precursor T lymphoblastic lymphoma, blastic NK cell lymphoma), tumors of the mature T and NK cells, including peripheral T-cell lymphoma and leukemia (PTL), adult T-cell leukemia/T-cell lymphomas and large granular lymphocytic leukemia, T-cell chronic lymphocytic leukemia/prolymphocytic leukemia, T-cell large granular lymphocytic leukemia, aggressive NK-cell leukemia, extranodal T-/NK cell lymphoma, enteropathy-type T-cell lymphoma, hepatosplenic T-cell lymphoma, anaplastic large cell lymphoma (ALCL), angiocetric and angioimmunoblastic T-cell lymphoma, mycosis fungoides/Sezary syndrome, and cutaneous T-cell lymphoma (CTCL). Other cancers that may be treatable by the antibodies of the invention include but are not limited to Hodgkin's lymphoma, tumors of lymphocyte precursor cells, including B-cell acute lymphoblastic leukemia/lymphoma (B-ALL), and T-cell acute lymphoblastic leukemia/lymphoma (T-ALL), thymoma, Langerhans cell histocytosis, multiple myeloma (MM), myeloid neoplasias such as acute myelogenous leukemias (AML), including AML with maturation, AML without differentiation, acute promyelocytic leukemia, acute myelomonocytic leukemia, and acute monocytic leukemias, myelodysplastic syndromes, and chronic myeloproliferative disorders (MDS), including chronic myelogenous leukemia (CML). Other cancers that may be treatable by the antibodies of the invention include but are not limited to tumors of the central nervous system such as glioma, glioblastoma, neuroblastoma, astrocytoma, medulloblastoma, ependymoma, and retinoblastoma; solid tumors of the head and neck (e.g. nasopharyngeal cancer, salivary gland carcinoma, and esophageal cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

Indications that may be treated by anti-CD40 antibodies of the invention include but are not limited to all non-Hodgkin's lymphomas (NHL), especially refractory/resistant NHL, chronic lymphocytic leukemia (CLL), B-cell acute lymphoblastic leukemia/lymphoma (B-ALL), mantle cell lymphoma (MCL), and multiple myeloma (MM).

Autoimmunity results from a breakdown of self-tolerance involving humoral and/or cell-mediated immune mechanisms. Among the consequences of failure in central and/or peripheral tolerance are survival and activation of self-reactive B cells and T cells. Several autoimmune diseases are defined by excessive activation of both B and/or T lymphocytes. Activation of these cells requires in cooperation, antigen engagement and co-stimulatory signals from interacting lymphocytes. Thus antibody-mediated depletion, inhibition, anti-proliferation, and/or blockade of B cells and/or T cells are therapeutic approaches for the treatment of autoimmune disease.

By "autoimmune diseases" herein include allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erythematosus, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiffman syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

By "inflammatory disorders" herein include acute respiratory distress syndrome (ARDS), acute septic arthritis, adjuvant arthritis, juvenile idiopathic arthritis, allergic encephalomyelitis, allergic rhinitis, allergic vasculitis, allergy, asthma, atherosclerosis, chronic inflammation due to chronic bacterial or viral infections, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus (HIV), human papilloma virus (HPV), influenza, measles, mumps, papova virus, polio, respiratory syncytial virus (RSV), rinderpest, rhinovirus, rotavirus, rubella, SARS virus, smallpox, viral meningitis, and the like. Infections diseases may also be caused by bacteria including *Bacillus anthracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibrio cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, leishmania, malaria, rickettsia, trypanosoma, and the like.

Furthermore, antibodies of the present invention may be used to prevent or treat additional conditions including but not limited to heart conditions such as congestive heart failure (CHF), myocarditis and other conditions of the myocardium;

skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

A number of the receptors that may interact with the antibodies of the present invention are polymorphic in the human population. For a given patient or population of patients, the efficacy of the antibodies of the present invention may be affected by the presence or absence of specific polymorphisms in proteins. For example, FcγRIIIA is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et al. (2004) Cancer Res. 64:4664-9, incorporated herein it its entirety by reference). Additional polymorphisms include but are not limited to FcγRIIA R131 or H131, and such polymorphisms are known to either increase or decrease Fc binding and subsequent biological activity, depending on the polymorphism. antibodies of the present invention may bind to a particular polymorphic form of a receptor, for example FcγRIIIA 158 V, or to bind with equivalent affinity to all of the polymorphisms at a particular position in the receptor, for example both the 158V and 158F polymorphisms of FcγRIIIA. In one embodiment, antibodies of the present invention may have equivalent binding to polymorphisms that may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In one embodiment, antibodies of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIB could receive a drug containing an antibody with reduced binding to such polymorphic form of the receptor, creating a more efficacious drug.

In one embodiment, patients are screened for one or more polymorphisms in order to predict the efficacy of the antibodies of the present invention. This information may be used, for example, to select patients to include or exclude from clinical trials or, post-approval, to provide guidance to physicians and patients regarding appropriate dosages and treatment options. For example, in patients that are homozygous or heterozygous for FcγRIIIA 158F antibody drugs such as the anti-CD20 mAb, Rituxan® are minimally effective (Carton 2002 Blood 99: 754-758; Weng 2003 J. Clin. Oncol. 21:3940-3947, each incorporated herein it its entirety by reference); such patients may show a much better clinical response to the antibodies of the present invention. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an antibody engineered to be specifically efficacious for such population, or alternatively where such therapy contains an antibody that does not show differential activity to the different forms of the polymorphism.

Included in the present invention are diagnostic tests to identify patients who are likely to show a favorable clinical response to an antibody of the present invention, or who are likely to exhibit a significantly better response when treated with an antibody of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In one embodiment, ADCC assays, such as those described previously, are used to predict, for a specific patient, the efficacy of a given antibody of the present invention. Such information may be used to identify patients for inclusion or exclusion in clinical trials, or to inform decisions regarding appropriate dosages and treatment regimens. Such information may also be used to select a drug that contains a particular antibody that shows superior activity in such assay.

Formulation

Pharmaceutical compositions are contemplated wherein an antibody of the present invention and one or more therapeutically active agents are formulated. Formulations of the antibodies of the present invention are prepared for storage by mixing the antibody having the desired degree of purity with optional pharmaceutically acceptable carriers, excipients or stabilizers (Remington's Pharmaceutical Sciences 16th edition, Osol, A. Ed., 1980, incorporated herein it its entirety by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG).

In one embodiment, the pharmaceutical composition that comprises the antibody of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration should be sterile. This is readily accomplished by filtration through sterile filtration membranes or other methods.

The antibodies disclosed herein may also be formulated as immunoliposomes. A liposome is a small vesicle comprising various types of lipids, phospholipids and/or surfactant that is useful for delivery of a therapeutic agent to a mammal. Liposomes containing the antibody are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. No. 4,485,045; U.S. Pat. No. 4,544,545; and PCT WO 97/38731, each incorporated herein it its entirety by reference. Liposomes with enhanced circulation time are disclosed in U.S. Pat. No. 5,013,556, incorporated herein it its entirety by reference. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, incorporated herein it its entirety by reference).

The antibody and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated herein it its entirety by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919, incorporated herein it its entirety by reference), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an antibody of the present invention, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the antibody may be directly applied as a solution or spray. As is known in the art, the pharmaceutical composition may be formulated accordingly depending upon the manner of introduction.

Subcutaneous administration may be desirable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658, incorporated herein it its entirety by reference). Antibodies of the present invention may be more amenable to subcutaneous administration due to, for example, increased potency, improved serum half-life, or enhanced solubility.

As is known in the art, protein therapeutics are often delivered by IV infusion or bolus. The antibodies of the present invention may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies of the present invention may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101:9763-8, each incorporated herein it its entirety by reference). Accordingly, antibodies that bind FcRn more effectively in the lung or that are released more efficiently in the bloodstream may have improved bioavailability following intrapulmonary administration. Antibodies of the present invention may also be more amenable to intrapulmonary administration due to, for example, improved solubility or altered isoelectric point.

Furthermore, antibodies of the present invention may be more amenable to oral delivery due to, for example, improved stability at gastric pH and increased resistance to proteolysis. Furthermore, FcRn appears to be expressed in the intestinal epithelia of adults (Dickinson et al. (1999) J. Clin. Invest. 104:903-11, incorporated herein it its entirety by reference), so antibodies of the present invention with improved FcRn interaction profiles may show enhanced bioavailability following oral administration. FcRn mediated transport of antibodies may also occur at other mucus membranes such as those in the gastrointestinal, respiratory, and genital tracts (Yoshida et al. (2004) Immunity 20:769-83, incorporated herein it its entirety by reference).

In addition, any of a number of delivery systems are known in the art and may be used to administer the antibodies of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol),polylactides, copolymers of L-glutamic acid and ethyl-L-glutamate, ethylene-vinyl acetate, lactic acid-glycolic acid copolymers such as the Lupron Depot®, and poly-D-(−)-3-hydroxyburyric acid. It is also possible to administer a nucleic acid encoding the antibody of the current invention, for example by retroviral infection, direct injection, or coating with lipids, cell surface receptors, or other transfection agents. In all cases, controlled release systems may be used to release the antibody at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In one embodiment, the concentration of the antibody is in the range of 0.003 µM to 1.0 molar. In order to treat a patient, a therapeutically effective dose of the antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, e.g., 1 to 10 mg/kg of body weight.

In some embodiments, only a single dose of the antibody is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The antibodies of the present invention may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody of the present invention may be administered to the patient along with chemotherapy, radiation therapy, or both chemotherapy and radiation therapy. The antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of the prophylactic or therapeutic agents at exactly the same time. Instead, it is meant that the antibody of the present invention and the other agent or agents are administered in a sequence and within a time interval such that they may act together to provide a benefit that is increased versus treatment with only either the antibody of the present invention or the other agent or agents. In one embodiment, that the antibody and the other agent or agents act additively, e.g., they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the antibodies of the present invention are administered with one or more additional molecules comprising antibodies or Fc. The antibodies of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti-17-1A cell surface antigen antibodies such as Panorex™ (edrecolomab); anti-4-1 BB antibodies; anti-4Dc antibodies; anti-A33 antibodies such as A33 and CDP-833; anti-αVβ1 integrin antibodies such as natalizumab; anti-αVβ7 integrin antibodies such as LDP-02; anti-αVβ1 integrin antibodies such as F-200, M-200, and SJ-749; anti-αVβ3 integrin antibodies such as abciximab, CNTO-95, Mab-17E6, and Vitaxin™; anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX- CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab, I-131 labeled anti-CD20), Rituxan® (rituximab), and Zevalin® (Ibritumomab tiuxetan, Y-90 labeled anti-CD20); anti-CD22 antibodies such as Lymphocide™ (epratuzumab, Y-90 labeled anti-CD22); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™, and IDEC-131; anti-CD44 antibodies such as bivatuzumab; anti-CD46 antibodies; anti-CD402 antibodies such as Campath® (alemtuzumab); anti-CD405 antibodies such as SC-1; anti-CD406 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, labetuzumab, and Pentacea™; anti-CTLA-4 antibodies such as MDX-101; anti-CXCR4 antibodies; anti-EGFR antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Muc1 antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antibodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcγR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the antibodies of the present invention may be co-administered or with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function. Fc receptor inhibitors include, but are not limited to, Fc molecules that are engineered to act as competitive inhibitors for binding to FcγRIIb, FcγRIIIa, or other Fc receptors, as well as other immunoglobulins and specifically the treatment called IVIg (intravenous immunoglobulin). In one embodiment, the inhibitor is administered and allowed to act before the antibody is administered. An alternative way of achieving the effect of sequential dosing would be to provide an immediate release dosage form of the Fc receptor inhibitor and then a sustained release formulation of the antibody of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the antibodies of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11;retinoic acid; esperamicins; capecitabine. Pharmaceutically acceptable salts, acids, or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985, each incorporated herein it its entirety by reference. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies of the present invention include but are not limited to any of the aforementioned chemotherapeutic agents.

A variety of other therapeutic agents may find use for administration with the antibodies of the present invention. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. one such anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD409 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activator inhibitor (PAI), platelet factor-4 (PF4), prinomastat, prolactin 16 kDa fragment, proliferin-related protein (PRP), PTK 7871ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (caireticulin fragment), ZS6126,and ZD6474.

In one embodiment, the antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo(2,3-d) pyrimidines; curcumin (diferuloyl methane, 4,5-bis (4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571,Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech), each patent publications incorporated herein it its entirety by reference.

In another embodiment, the antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to: non-steroidal anti-inflammatory drugs (NSAIDs) such as aspirin, ibuprofen, celecoxib, diclofenac, etodolac, fenoprofen, indomethacin, ketoralac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD402, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (e.g. leflunomide), methotrexate, minocycline, mizoribine, mycophenolate mofetil, rapamycin, and sulfasasazine.

In an alternate embodiment, antibodies of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In one embodiment, cytokines or other agents that stimulate cells of the immune system are co-administered with the antibody of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand. J. Immunol. 57: 221-8, incorporated herein it its entirety by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the antibody of the present invention. Such a mode of treatment may limit unwanted effector function.

In an additional embodiment, the antibody is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefmetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg.

flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetracyclenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine.

The antibodies of the present invention may be combined with other therapeutic regimens. For example, in one embodiment, the patient to be treated with an antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient.

It is of course contemplated that the antibodies of the invention may employ in combination with still other therapeutic techniques such as surgery or phototherapy.

EXAMPLES

Examples are provided below to illustrate the present invention. These examples are not meant to constrain the present invention to any particular application or theory of operation.

For reference to immunoglobulin constant regions, positions are numbered according to the EU index as in Kabat (Kabat et al., 1991, *Sequences of Proteins of Immunological Interest*, 5th Ed., United States Public Health Service, National Institutes of Health, Bethesda).

Example 1

Anti-CD40 Antibodies with Amino Acid Modifications that Enhance Effector Function The anti-CD40 antibodies of the invention are intended as clinical candidates for anti-cancer therapeutics. To investigate the possibility of improving the effector function of an antibody that targets CD40, variant versions of anti-CD40 antibodies were engineered.

FIG. 5 provides some heavy and light chain variable region sequences of the anti-CD40 antibodies S2C6 (Paulie S. et al., 1984. Cancer Immunol Immunother. 17:173-179), G28-5 (Clark E. A. et al., 1988. Eur J Immunol. 18:451-457), and 5D12 (de Boer M. et al., 1992. J Immunol Methods. 152:15-23), each incorporated herein it its entirety by reference, used in the present study. The mouse, parent chimeric heavy and light chains are labeled H0 and L0, respectively. The genes for the murine WT antibody VH and VL, designated H0 and L0 respectively, were constructed using gene synthesis techniques and subcloned into the mammalian expression vector pcDNA3.1Zeo (Invitrogen) comprising the full length light kappa (Cκ) and heavy chain IgG1 constant regions. Variant S239D/I332E (effector function enhanced anti-CD40) was constructed in the Fc region of a hybrid IgG1/IgG2 (FIG. 1) antibody in the pcDNA3.1Zeo vector using QuikChange mutagenesis techniques (Stratagene). All sequences were sequenced to confirm the fidelity of the sequence. Plasmids containing heavy chain gene (VH-CH1-CH2-CH3) (wild-type or variants) were co-transfected with plasmid containing light chain gene (VL-CLK) into 293T cells. Media were harvested 5 days after transfection, and antibodies were purified from the supernatant using protein A affinity chromatography (Pierce, Catalog #20334).

To assess the capacity of the antibody variants to mediate effector function against CD40 expressing cells, effector function enhanced anti-CD40 antibodies were tested in a cell-based ADCC assay. Human peripheral blood monocytes (PBMCs) were isolated from leukopaks and used as effector cells, and CD40 positive cancer cells were used as target cells. Target cells were seeded at 20,000 cells/well and treated with designated antibodies in triplicates. PBMCs isolated using a Ficoll gradient were added in excess to target cells and co-cultured for 4 hrs before processing for LDH activity using the Cytotoxicity Detection Kit according to the manufacturer's instructions. FIG. 6 shows the results of ADCC assays comparing WT IgG1, effector function enhanced anti-CD40 antibodies (hybrid S239D/I332E), and/or effector function enhanced rituximab (hybrid S239D/I332E) on the cell lines Daudi (Burkitt's Lymphoma), Raji (Burkitt's Lymphoma), and RPMI8226 (Multiple Myeloma) for antibodies S2C6 (FIG. 6a), 5D12 (FIG. 6b), and G28-5 (FIG. 6c). The graphs show that the antibodies differ not only in their EC50, reflecting their relative potency, but also in the maximal level of ADCC attainable by the antibodies at saturating concentrations, reflecting their relative efficacy. These two terms, potency and efficacy, are sometimes used loosely to refer to desired clinical properties. In the current experimental context, however, they are denoted as specific quantities, and therefore are here explicitly defined. By "potency" as used in the current experimental context is meant the EC50 of an antibody. By "efficacy" as used in the current experimental context is meant the maximal possible effector function of an antibody at saturating levels. Considerable enhancements in potency and efficacy are observed for the Fc variant antibodies with enhanced effector function as compared to the antibodies with WT Fc region. All three effector function enhanced antibodies displayed ADCC on the Multiple Myeloma cell line RPMI8226, with S2C6 showing the most efficacy, indicating that this antibody may be an effective treatment option for Multiple Myeloma.

Example 2

Platelet Activation Assay with Anti-CD40 Antibody S2C6

To determine if anti-CD40 antibody S2C6 has any effect of platelet activation, a platelet activation assay was performed. Platelets were obtained from fresh blood drawn by venipuncture in NaCitrate and spun at low speed (100×g) for 15 minutes from which the straw colored upper phase was removed as platelet rich plasma (PRP). The PRP was further spun at 700×g for 2.5 minutes and the pellet was saved and washed twice with 10 mM EDTA, 1% FBS in $CaCl_2$ and $MgCl_2$ free PBS. The platelet pellet was resuspended in EDTA/FBS/PBS at 1.5× of the PRP volume and used in the experiment. Antibody serial dilutions were performed in EDTA/FBS/PBS in 50 μl volume in 96 well microtiter plates with 5× molar access of cross linking antibody. For IV.3 antibody (mouse anti-human IgG FcgRIIa specific antibody), goat anti-mouse IgG Fc specific antibody was used for cross-linking and for all other antibodies goat anti-human IgG Fc specific biotinylated antibody was used for cross-linking. To the antibody dilution wells, 50 μL of prepared washed platelets were added. Samples were incubated for 35 minutes at 37° C. and developed with the ATP dependent luminescence without SDS kit (ATP-Lite, PerkinElmer). Results for the platelet activation assay are shown in FIG. 7. The results show that neither S2C6 IgG1 or effector function enhanced S2C6 activated platelets at concentrations of less than 10000 ng/mL, while the positive control antibody IV.3 clearly mediates platelet activation at all concentrations.

Example 3

Anti-Proliferation Assay of Anti-CD40 Antibodies on the Burkitt's Lymphoma Cell Line HS-Sultan To observe an anti-proliferative effect in vitro, many antibodies require cross-linking, usually accomplished by a secondary antibody. It has been proposed that corresponding in vivo effects for these antibodies may be dependent on cross-linking mediated by Fc receptors expressed on the surface of effector cells. In this experiment, anti-proliferative effects of the chimeric antibodies S2C6 and 5D12 were assayed using the Burkitt's Lymphoma cell line HS-Sultan (FIG. 8). The HS-Sultan cells were maintained in 10% FBS/RPMI1640 with NaPyruvate and HEPES. The antibody serial dilutions were prepared in 96 well microtiter plates with 10× molar access of cross-linking antibodies in 50 μl of 2% FBS/RPMI1640 with HEPES and NaPyruvate. In some cases, additional factors are added at a fixed concentration as indicated. The cross-linking antibodies used were goat anti-human IgG Fc specific biotinylated antibody and goat anti-mouse IgG Fc specific antibody for human or mouse antibodies, respectively. HS-Sultan cells were pelleted and resuspended in 2% FBS/RPMI1640 with HEPES and NaPyruvate at 100,000 cells/ml and 50 μl was added to the prepared antibody dilutions. After 4 days at 37° C., the amount of ATP present in the live cells was detected using the ATP dependent luminescent viability assay kit (Cell TiterGlo, Promega Corp.). Human IgG with and without CD40 ligand and cells only were used as controls. Both S2C6 and 5D12 show anti-proliferative effects on the HS-Sultan cell line.

Example 4

Anti-CD40 Antibodies with Reduced Potential for Immunogenicity

In order to reduce the potential for immunogenicity of the H0 and L0 S2C6 variable regions, the immunogenicity was reduced using a method described in U.S. Ser. No. 11/004, 590, entitled "Methods of Generating Variant Proteins with Increased Host String Content and Compositions Thereof", filed on Dec. 6, 2004. The method reduces the potential for immunogenicity by increasing the human string content of the antibody through mutations. The anti-CD40 variable region variants with reduced potential for immunogenicity are named H1, H2, H3, and H4 for the heavy chain, and L1, L2, and L3 for the light chain. The sequences for these variants are provided in FIG. 9. Light and heavy chains were constructed by gene synthesis. Light chains were subcloned into the pcDNA3.1Zeo vector comprising the full length light kappa (G0 constant region, and heavy chains were subcloned into pcNDA3.1Zeo vectors comprising both the WT IgG1 constant chain (designated IgG1_WT), as well as the heavy chain Hybrid IgG constant region with mutations S239D/I332E (designated Hybrid_S239D/I332E). All sequences were sequenced to confirm the fidelity of the sequence. Combinations of the different heavy and light chains were expressed in 293T cells and purified as described above. For example, an S2C6 antibody comprising the H3 heavy chain and L1 light chain would be designated as S2C6_H3L1.

ADCC was used to differentiate the reduced immunogenicity templates. Templates were incubated at 60° C. for up to 48 hrs and ADCC measured on RAMOS cells at various time points in order to assess the relative stability of each template (FIG. 11). Human peripheral blood monocytes (PBMCs) were isolated from leukopaks and used as effector cells, and CD40 positive cancer cells were used as target cells. Target cells were seeded in 96-well plates and treated with designated antibodies in triplicate. PBMCs isolated using a Ficoll gradient were added in excess to target cells and co-cultured for 4 hrs before processing for LDH activity using the Cytotoxicity Detection Kit according to the manufacturer's instructions. After a 48 hr incubation, reduced immunogenicity templates H1L1, H1L3, H2L1, and H2L3 still maintained acceptable ADCC potency and efficacy. Based on ADCC potency and relative stability, a reduced immunogenicity (humanized) S2C6 antibody was chosen for further development.

Example 5

ADCC of Reduced Immunogenicity S2C6 on Ramos, Namalwa, IM-9, and RPMI Cells

Figure 12B:
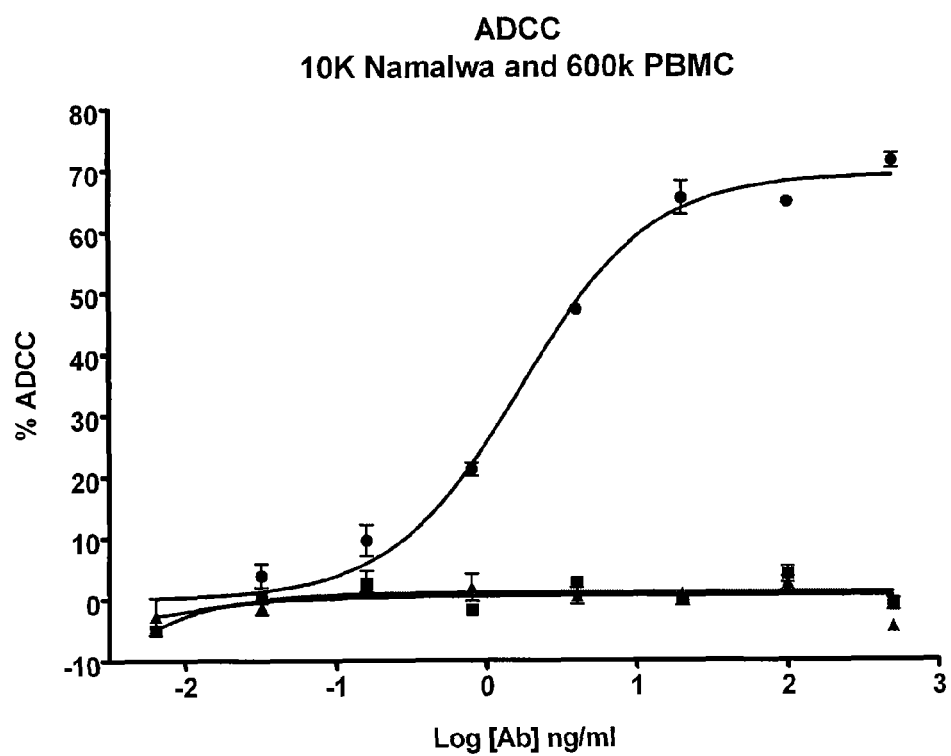

In order to evaluate cytotoxic properties of effector function enhanced and reduced immunogenicity S2C6 we performed ADCC assays on the cell lines Ramos (Burkitt's Lymphoma), Namalwa (Burkitt's Lymphoma), IM-9 (B-lymphoblastoid), and RPMI8226 (Multiple Myeloma) (FIGS. 12a-12d, respectively). For Ramos and Namalwa cell lines, human peripheral blood monocytes (PBMCs) were isolated from leukopaks and used as effector cells, and the CD40 positive cancer cells were used as target cells. Target cells were seeded at 10,000 cells/well in 96-well plates and treated with designated antibodies in triplicate. PBMCs isolated using a Ficoll gradient were added in excess to target cells and co-cultured for 4 hrs before processing for LDH activity using the Cytotoxicity Detection Kit according to the manufacturer's instructions. For IM-9 and RPMI8226, ADCC assays were performed with purified NK cells. ADCC with purified NK cells is done in 96-well microtiter plates. The NK cells were purified from human PBMC using the kit from Miltenyi Biotec (Cat #130-091-152) and incubated in 10% FBS/RPMI1640 overnight with 10 ng/ml IL-2. The following day, 10,000 cancer target cells are opsonized with varying concentrations of antibody and 50k NK cells are used for each antibody concentration in triplicates. The target cells are washed three times while NK cells are washed twice with RPMI1640 and both resuspended in 1% FBS/RPMI1640 and added to the antibody solutions. After 4 hours of incubation at 37° C. in a humidified incubator with 5% $CO_2$, the assay was quantified using LDH dependent CytoTox-One fluorescence dependent detection system from Promega (#PAG7891). Total LDH signal is determined from the Triton-X100 lysed target cells (Total Target LDH) and used to normalize against the spontaneous LDH background (Spontaneous Background) adjusted experimental values. Thus % ADCC=((Experimental Value−Spontaneous Background)/(Total Target LDH−Target LDH))*100. Spontaneous background is the value obtained from the Target and NK cells co-incubated in the absence of antibody. Target LDH is the value from the target cancer cells alone spontaneously releasing LDH during the incubation. As can be seen in FIG. 12a, S2C6 H3L1 Hybrid S239D/I332 mediates very high levels of ADCC on the Burkitt's Lymphoma cell line Ramos. In FIG. 12b, S2C6 H4L3 Hybrid S239D/I332E mediates a high levels of ADCC on the Burkitt's Lymphoma cell line Namalwa. In FIG. 12c, S2C6 H1L1 Hybrid S239D/I332E mediates high levels of ADCC on the B-lymphoblastoid cell line IM-9. Finally, in FIG. 12d, S2C6 H1L1 Hybrid S239D/I332E mediates high levels of ADCC on the multiple myeloma cell line RPMI8226. Rituximab and WT IgG1 antibodies are also used in some of the assays for comparison. These assays show that humanized and effector function enhanced S2C6 has potent in vitro efficacy on several different cell lines representing B-cell malignancies.

Example 6

ADCC of an Enhanced Effector Function Anti-CD40 Antibody with Reduced Fucose Content Anti-CD40 antibodies with enhanced effector function (e.g., S2C6 H1 L1 Hybrid S239D/I332E) are evaluated with reduced fucose content. The Lec13 cell line (Ripka et al. Arch. Biochem. Biophys. 49:533-545 (1986)) is utilized to express anti-CD40 antibodies with reduced fucose content. Lec13 refers to the lectin-resistant Chinese Hamster Ovary (CHO) mutant cell line which displays a defective fucose metabolism and therefore has a diminished ability to add fucose to complex carbohydrates. That cell line is described in Ripka & Stanley, 1986, Somatic Cell & Molec. Gen. 12(1): 51-62; and Ripka et al., 1986, Arch. Biochem. Biophys. 249 (2):533-545. Lec13 cells are believed to lack the transcript for GDP-D-mannose-4,6-dehydratase, a key enzyme for fucose metabolism. Ohyama et al., 1988, J. Biol. Chem. 273(23): 14582-14587. GDP-D-mannose-4,6-dehydratase generates GDP-mannose-4-keto-6-D-deoxymannose from GDP-mannose, which is then converted by the FX protein to GDP-L-fucose. Expression of fucosylated oligosaccharides is dependent on the GDP-L-fucose donor substrates and fucosyltransferase(s). The Lec13 CHO cell line is deficient in its ability to add fucose, but provides IgG with oligosaccharide which is otherwise similar to that found in normal CHO cell lines and from human serum (Jefferis, R. et al., 1990, Biochem. J. 268, 529-537; Raju, S. et al., 2000, Glycobiology 10, 477-486; Routier, F. H., et al., 1997, Glycoconj. J. 14, 201-207). Normal CHO and HEK293 cells add fucose to IgG oligosaccharide to a high degree, typically from 80-98%, and IgGs from sera are also highly fucosylated (Jefferis, R. et al., 1990, Biochem. J. 268, 529-537; Raju, S. et al., 2000, Glycobiology 10, 477-486; Routier, F. H., et al., 1997, Glycoconj. J. 14, 201-207; Shields et al., 2002, J Biol Chem 277(90): 26733-26740). It is well established that antibodies expressed in transfected Lec13 cells consistently produce about 10% fucosylated carbohydrate (Shields et al., 2002, J Biol Chem 277(90):26733-26740).

ADCC assays are performed with purified NK cells on Raji and RPMI8226 cells using anti-CD40 antibodies with and without enhanced effector function variants and with and without reduced fucosylation. It is expected that both ADCC potency and efficacy for anti-CD40 antibody with reduced fucose content (S2C6_H1L1__1gG1_WT-fucose) are significantly higher than those of the antibody with native fucose content (S2C6_H1L1_IgG1_WT) and similar to those of the antibody with amino acid modification (S2C6_H1L1_Hybrid__239D/I332E+fucose). This experiment will illustrate that combinations of amino acid modifications and modified glycoforms may be used to optimize anti-CD40 antibodies for effector function properties.

The use of the Lec13 cell line is not meant to limit the present invention to that particular mode of reducing fucose content. A variety of other methods are known in the art for controlling the level of fucosylated and/or bisecting oligosaccharides that are covalently attached to the Fc region, including but not limited to expression in various organisms or cell lines, engineered or otherwise (for example Lec13 CHO cells or rat hybridoma YB2/0 cells), regulation of enzymes involved in the glycosylation pathway (for example FUT8 [α1,6-fucosyltransarase] and/or β1-4-N-acetylglucosaminyltransferase III [GnTIII]), and modification of modifying carbohydrate(s) after the IgG has been expressed (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; Yamane-Ohnuki et al., 2004, Biotechnology and Bioengineering 87(5):614-621); (U.S. Pat. No. 6,602, 684; U.S. Ser. No. 10/277,370; U.S. Ser. No. 10/113,929; PCT WO 00/61739A1; PCT WO 01/29246A1; PCT WO 02/31140A1; PCT WO 02/30954A1).

Example 7

Human Tumor Xenograft Models

In the first study, five to six week old SCID mice were injected subcutaneously (s.c.) with $5\times10^6$ human Ramos Burkitt's lymphoma cells. On day 14, mice bearing tumors of 40-100 mm³ were injected intraperitoneally (i.p.) with 6 mg/kg of S2C6 H1L1 Hybrid S239D/I332E, isotype control (Hybrid S239D/I332E Fc), or with PBS, 3× per week for 3 weeks. Tumors were measured twice per week and tumor volume was determined using the formula L×W²/2, where L=length and W=width. Tumor growth was monitored for 40 days post tumor cell injection.

Figure 13:
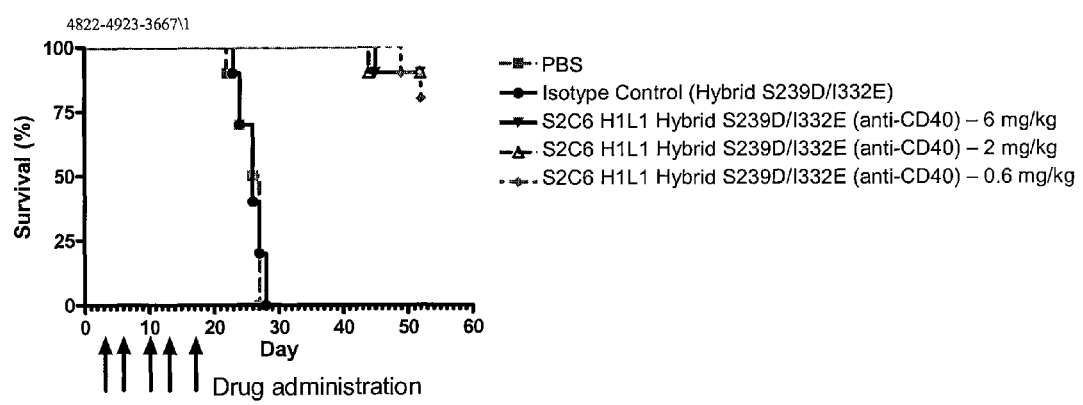
FIG. 13. Survival of SCID mice in a model of Ramos Burkitt's lymphoma after treatment with several humanized S2C6 templates.

In a separate study, five to six week old SCID mice were injected intravenously (i.v.) with 5×10⁶ human Ramos Burkitt's lymphoma cells. On days 3, 6, 10, 13 and 17 post tumor cell injection, mice were injected intraperitoneally (i.p.) with 6, 2 or 0.6 mg/kg of S2C6 H1L1 Hybrid S239D/I332E, isotype control (Hybrid S239D/I332E Fc), or with PBS. Mice were monitored for survival for 60 days. As shown in FIG. 13, S2C6 H1 L1 Hybrid S239/I332E significantly prolonged the survival of these animals.

The use of particular modifications, for example the substitutions 239D and 332E, to enhance effector function are not meant to constrain the anti-CD40 antibodies to these particular modifications. As described above in the section entitled "Modifications for optimizing effector function", a large number of modifications, including amino acid modifications and modified glycoforms, are contemplated for anti-CD40 antibodies to improve their effector function properties.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

What is claimed is:

1. An antibody that binds CD40, said antibody comprising a heavy chain and/or a light chain, wherein said heavy chain comprises a $V_H$ domain having an amino acid sequence selected from the group consisting of the amino acid sequence of SEQ ID NOs:34-37, and wherein said light chain comprises a $V_L$ domain having an amino acid sequence selected from the group consisting of SEQ ID NOs: 38 and 40.

2. The antibody of claim 1, wherein said heavy chain comprises a $V_H$ domain having an amino acid sequence selected from the group consisting of the amino acid sequence of SEQ ID NOs:34-35, and wherein said light chain comprises a $V_L$ domain having an amino acid sequence selected from the group consisting of SEQ ID NOs: 38 and 40.

3. The antibody of claim 2 further comprising a modification in the constant region relative to the parent anti-CD40 antibody, wherein said modification is an amino acid substitution selected from the group consisting of 236A, 239D, 268D, 330Y, 330L, and 332E, and wherein the numbering system is as in Kabat, and wherein said antibody binds with increased affinity to the FcγRIIIa receptor as compared to the parent antibody.

4. The antibody of claim 3, wherein said antibody comprises a heavy chain $V_H$ domain having an amino acid sequence of SEQ ID NO:34 and a light chain $V_L$ domain having an amino acid sequence of SEQ ID NO:38.

5. A variant anti-CD40 antibody variable domain relative to antibody S2C6 variable domain comprising a heavy chain, SEQ ID NO:10, and a light chain, SEQ ID NO:11, wherein said variant comprises at least one set selected from the group consisting of: a first set, a second set, a third set, a fourth set, a fifth set, and a sixth set, wherein said first set consists of substitutions Q5V, P9A, D10E, L11V and V12K relative to SEQ ID NO:10, wherein said second set consists of substitutions K38R, S40A, and H41P relative to SEQ ID NO:10, wherein said third set consists of substitutions K67R, A68V, I69T, L70I, and T71S relative to SEQ ID NO:10, wherein said fourth set consists of substitutions T109L and L110V relative to SEQ ID NO:10, wherein said fifth set consists of substitutions T7S, A17E and Q18P relative to SEQ ID NO:11, and, wherein said sixth set consists of substitutions K50Q, L88V and Q112K relative to SEQ ID NO:11.

6. A method of treating a B-cell related disease selected from the group consisting of:
non-Hodgkin's lymphomas (NHL), chronic lymphocytic leukemia (CLL), B-cell acute lymphoblastic leukemia/lymphoma (B-ALL), mantle cell lymphoma (MCL), hairy cell leukemia (HCL), chronic myelogenous leukemia (CML), and multiple myeloma (MM), wherein said method comprises administering an antibody according to claim 1.

7. A method of treating a human solid tumor expressing CD40, wherein said method comprises administering an antibody according to claim 1.

8. The method of claim 6 or 7, wherein said antibody is administered in combination with at least one agent selected from the group consisting of a cytotoxic agent, a chemotherapeutic agent, a cytokine, a growth inhibitory agent, an anti-hormonal agent, a kinase inhibitor, an anti-angiogenic agent, a cardioprotectant, an immunostimulatory agent, an immunosuppressive agent, an agent that promotes proliferation of hematological cells, an angiogenesis inhibitor, a protein tyrosine kinase inhibitor, and a second antibody.

9. A composition comprising an antibody according to claim 1 and an acceptable carrier.

10. A method of inhibiting proliferation of a cell expressing CD40, wherein said method comprises contacting said cell with an antibody according to claim 1.

11. A method of enhancing antibody dependent cell cytotoxicity toward a cell expressing CD40, wherein said method comprises contacting said cell with an antibody according to claim 1.

12. A method of depleting a mammal of at least one cell expressing CD40, wherein said method comprises administering to the mammal an antibody according to claim 1.

13. The antibody of claim 3, wherein said antibody comprises a heavy chain $V_H$ domain having an amino acid sequence of SEQ ID NO:34 and a light chain $V_L$ domain having an amino acid sequence of SEQ ID NO:40.

14. A method of treating a B-cell related disease selected from the group consisting of:
non-Hodgkin's lymphomas (NHL), chronic lymphocytic leukemia (CLL), B-cell acute lymphoblastic leukemia/lymphoma (B-ALL), mantle cell lymphoma (MCL), hairy cell leukemia (HCL), chronic myelogenous leukemia (CML), and multiple myeloma (MM), wherein said method comprises administering an antibody according to claim 13.

15. A method of treating a human solid tumor expressing CD40, wherein said method comprises administering an antibody according to claim 13.

16. The method of claim 14, wherein said antibody is administered in combination with at least one agent selected from the group consisting of a cytotoxic agent, a chemotherapeutic agent, a cytokine, a growth inhibitory agent, an anti-hormonal agent, a kinase inhibitor, an anti-angiogenic agent, a cardioprotectant, an immunostimulatory agent, an immunosuppressive agent, an agent that promotes proliferation of hematological cells, an angiogenesis inhibitor, a protein tyrosine kinase inhibitor, and a second antibody.

17. The method of claim 15, wherein said antibody is administered in combination with at least one agent selected from the group consisting of a cytotoxic agent, a chemotherapeutic agent, a cytokine, a growth inhibitory agent, an anti-hormonal agent, a kinase inhibitor, an anti-angiogenic agent, a cardioprotectant, an immunostimulatory agent, an immunosuppressive agent, an agent that promotes proliferation of hematological cells, an angiogenesis inhibitor, a protein tyrosine kinase inhibitor, and a second antibody.

18. A composition comprising an antibody according to claim 13 and an acceptable carrier.

19. A method of inhibiting proliferation of a cell expressing CD40, wherein said method comprises contacting said cell with an antibody according to claim 13.

20. A method of enhancing antibody dependent cell cytotoxicity toward a cell expressing CD40, wherein said method comprises contacting said cell with an antibody according to claim 13.

21. A method of depleting a mammal of at least one cell expressing CD40, wherein said method comprises administering to the mammal an antibody according to claim 13.

22. A method of inhibiting the proliferation of a cell expressing CD40 in a patient having an autoimmune disease selected from the group consisting of allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orehitis, autoimmune thrombocytopenia, autoimmune urticaria, Behcet's disease, bullous pemphigoid, cardiomyopathy, Castleman's syndrome, celiac spruce-dermatitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erythematosus, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff man syndrome, systemic lupus erythematosus, takayasu arteritis, temporal arterists/giant cell arteritis, thrombotic thrombocytopenia purpura, ulcerative colitis, uveitis, vasculitides such as dermatitis herpetiformis vasculitis, vitiligo, and Wegner's granulomatosis,
the method comprising administering the antibody of claim 1.

23. A method of inhibiting the proliferation of a cell expressing CD40 in a patient having an autoimmune disease selected from the group consisting of allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orehitis, autoimmune thrombocytopenia, autoimmune urticaria, Behcet's disease, bullous pemphigoid, cardiomyopathy, Castleman's syndrome, celiac spruce-dermatitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erythematosus, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff man syndrome, systemic lupus erythematosus, takayasu arteritis, temporal arterists/giant cell arteritis, thrombotic thrombocytopenia purpura, ulcerative colitis, uveitis, vasculitides such as dermatitis herpetiformis vasculitis, vitiligo, and Wegner's granulomatosis,
the method comprising administering an antibody according to claim 13.

24. A method of inhibiting the proliferation of a cell expressing CD40 in a patient having a cancer selected from the group consisting of Burkitt's lymphoma (BL), small lymphocytic lymphoma/chronic lymphocytic leukemia (SLL/CLL), mantle cell lymphoma (MCL), follicular lymphoma (FL), diffuse large B-cell lymphoma (DLCL), marginal zone lymphoma (MZL), hairy cell leukemia (HCL) lymphoplasmacytic leukemia (LPL), extranodal marginal zone B-cell lymphoma of mucosa-associated lymphoid tissue (MALT), nodal marginal zone B cell lymphoma, mediastinal large cell lymphoma, intravascular large cell lymphoma, primary effusion lymphoma, precursor B-lymphoblastic leukemia/lymphoma, blastic NK cell lymphoma, large granular lymphocytic leukemia, aggressive NK-cell leukemia, extranodal NK cell lymphoma, anaplastic large cell lymphoma (ALCL), mycosis fungoides/Sezary syndrome, Hodgkin's lymphoma, B-cell acute lymphoblastic leukemia/lymphoma (B-ALL), Langerhans cell histocytosis, multiple myeloma (MM), myelogenous leukemia, acute myelogenous leukemia (AML), AML with maturation, AML without differentiation, acute promyelocytic leukemia, acute myelomonocytic leukemia, acute monocytic leukemia, myelodysplastic syndrome, chronic myeloproliferative disorder (MDS), and chronic myelogenous leukemia (CML),
the method comprising administering an antibody according to claim 1.

25. A method of inhibiting the proliferation of a cell expressing CD40 in a patient having a cancer selected from the group consisting of Burkitt's lymphoma (BL), small lymphocytic lymphoma/chronic lymphocytic leukemia (SLL/CLL), mantle cell lymphoma (MCL), follicular lymphoma (FL), diffuse large B-cell lymphoma (DLCL), marginal zone lymphoma (MZL), hairy cell leukemia (HCL) lymphoplasmacytic leukemia (LPL), extranodal marginal zone B-cell lymphoma of mucosa-associated lymphoid tissue (MALT), nodal marginal zone B cell lymphoma, mediastinal large cell lymphoma, intravascular large cell lymphoma, primary effusion lymphoma, precursor B-lymphoblastic leukemia/lymphoma, blastic NK cell lymphoma, large granular lymphocytic leukemia, aggressive NK-cell leukemia, extranodal NK cell lymphoma, anaplastic large cell lymphoma (ALCL), mycosis fungoides/Sezary syndrome, Hodgkin's lymphoma, B-cell acute lymphoblastic leukemia/lymphoma (B-ALL), Langerhans cell histocytosis, multiple myeloma (MM), myelogenous leukemia, acute myelogenous leukemia (AML), AML with maturation, AML without differentiation, acute promyelocytic leukemia, acute myelomonocytic leukemia, acute monocytic leukemia, myelodysplastic syndrome, chronic myeloproliferative disorder (MDS), and chronic myelogenous leukemia (CML), the method comprising administering an antibody according to claim 13.

26. A method of inhibiting the proliferation of a cell expressing CD40 in a patient having a cancer selected from the group consisting of glioma, glioblastoma, neuroblastoma, astrocytoma, medulloblastoma, ependymoma, retinoblastoma, nasopharyngeal cancer, salivary gland carcinoma, esophageal cancer, small-cell lung cancer, non-small cell lung cancer, adenocarcinoma of the lung, squamous carcinoma of the lung, gastrointestinal cancer, cancer of the bile duct, cancer of the biliary tract, colon cancer, rectal cancer, colorectal cancer, anal carcinoma, testicular cancer, penile cancer, prostate cancer, uterine cancer, vaginal cancer, vulval cancer, cervical cancer, ovarian cancer, endometrial cancer, melanoma, basal cell carcinoma, squamous cell cancer, actinic keratosis, liver cancer, hepatic carcinoma, hepatocellular cancer, hepatoma, osteoclastoma, osteolytic bone cancer, pancreatic cancer, bladder cancer, kidney cancer, renal cancer, thyroid cancer, breast cancer, cancer of the peritoneum, Kaposi's sarcoma, angiosarcoma, and hemagiopericytoma, the method comprising administering an antibody according to claim 1.

27. A method of inhibiting the proliferation of a cell expressing CD40 in a patient having a cancer selected from the group consisting of glioma, glioblastoma, neuroblastoma, astrocytoma, medulloblastoma, ependymoma, retinoblastoma, nasopharyngeal cancer, salivary gland carcinoma, esophageal cancer, small-cell lung cancer, non-small cell lung cancer, adenocarcinoma of the lung, squamous carcinoma of the lung, gastrointestinal cancer, cancer of the bile duct, cancer of the biliary tract, colon cancer, rectal cancer, colorectal cancer, anal carcinoma, testicular cancer, penile cancer, prostate cancer, uterine cancer, vaginal cancer, vulval cancer, cervical cancer, ovarian cancer, endometrial cancer, melanoma, basal cell carcinoma, squamous cell cancer, actinic keratosis, liver cancer, hepatic carcinoma, hepatocellular cancer, hepatoma, osteoclastoma, osteolytic bone cancer, pancreatic cancer, bladder cancer, kidney cancer, renal cancer, thyroid cancer, breast cancer, cancer of the peritoneum, Kaposi's sarcoma, angiosarcoma, and hemagiopericytoma, the method comprising administering an antibody according to claim 13.

\* \* \* \* \*

UNITED STATES PATENT AND TRADEMARK OFFICE
CERTIFICATE OF CORRECTION

PATENT NO.         : 8,551,485 B2                                    Page 1 of 1
APPLICATION NO.    : 12/864075
DATED              : October 8, 2013
INVENTOR(S)        : Bernett et al.

It is certified that error appears in the above-identified patent and that said Letters Patent is hereby corrected as shown below:

In the Claims

| Column | Line | PTO | Should Be |
|---|---|---|---|
| 115 | 11 | "greata" | -- areata -- |
| 115 | 42 | "temporal arteristis" | -- temporal arteritis -- |
| 115 | 51 | "greata" | -- areata -- |
| 116 | 15 | "temporal arteristis" | -- temporal arteritis -- |

Signed and Sealed this

Thirty-first Day of December, 2013

Margaret A. Focarino
*Commissioner for Patents of the United States Patent and Trademark Office*

SEQUENCE LISTING

```
<160> NUMBER OF SEQ ID NOS: 40

<210> SEQ ID NO 1
<211> LENGTH: 107
<212> TYPE: PRT
<213> ORGANISM: Homo sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

-continued

```
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 3
<211> LENGTH: 326
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 4
<211> LENGTH: 377
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190
```

-continued

```
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 5
<211> LENGTH: 327
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 6
<211> LENGTH: 330
<212> TYPE: PRT
<213> ORGANISM: Artificial Sequence
<220> FEATURE:
<223> OTHER INFORMATION: Hybrid constant heavy chain (CH)

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
```

```
            225                 230                 235                 240
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 330
<212> TYPE: PRT
<213> ORGANISM: Artificial Sequence
<220> FEATURE:
<223> OTHER INFORMATION: Hybrid constant heavy chain (CH) with 239D and
      332E substitutions

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                        260                 265                 270
Asn Tyr Lys Thr Thr Pro Met Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 276
<212> TYPE: PRT
<213> ORGANISM: Homo sapiens

<400> SEQUENCE: 8

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg
        275

<210> SEQ ID NO 9
<211> LENGTH: 203
<212> TYPE: PRT
```

<213> ORGANISM: Homo sapiens

<400> SEQUENCE: 9

```
Met Val Arg Leu Pro Leu Gln Cys Val Leu Trp Gly Cys Leu Leu Thr
1               5                   10                  15
Ala Val His Pro Glu Pro Pro Thr Ala Cys Arg Glu Lys Gln Tyr Leu
            20                  25                  30
Ile Asn Ser Gln Cys Cys Ser Leu Cys Gln Pro Gly Gln Lys Leu Val
        35                  40                  45
Ser Asp Cys Thr Glu Phe Thr Glu Thr Glu Cys Leu Pro Cys Gly Glu
    50                  55                  60
Ser Glu Phe Leu Asp Thr Trp Asn Arg Glu Thr His Cys His Gln His
65                  70                  75                  80
Lys Tyr Cys Asp Pro Asn Leu Gly Leu Arg Val Gln Gln Lys Gly Thr
                85                  90                  95
Ser Glu Thr Asp Thr Ile Cys Thr Cys Glu Glu Gly Trp His Cys Thr
            100                 105                 110
Ser Glu Ala Cys Glu Ser Cys Val Leu His Arg Ser Cys Ser Pro Gly
        115                 120                 125
Phe Gly Val Lys Gln Ile Ala Thr Gly Val Ser Asp Thr Ile Cys Glu
    130                 135                 140
Pro Cys Pro Val Gly Phe Phe Ser Asn Val Ser Ser Ala Phe Glu Lys
145                 150                 155                 160
Cys His Pro Trp Thr Arg Ser Pro Gly Ser Ala Glu Ser Pro Gly Gly
                165                 170                 175
Asp Pro His His Leu Arg Asp Pro Val Cys His Pro Leu Gly Ala Gly
            180                 185                 190
Leu Tyr Gln Lys Gly Gly Gln Glu Ala Asn Gln
        195                 200
```

<210> SEQ ID NO 10
<211> LENGTH: 114
<212> TYPE: PRT
<213> ORGANISM: Mus musculus

<400> SEQUENCE: 10

```
Glu Val Gln Leu Gln Gln Ser Gly Pro Asp Leu Val Lys Pro Gly Ala
1               5                   10                  15
Ser Val Lys Ile Ser Cys Lys Ala Ser Gly Tyr Ser Phe Thr Gly Tyr
            20                  25                  30
Tyr Ile His Trp Val Lys Gln Ser His Gly Lys Ser Leu Glu Trp Ile
        35                  40                  45
Gly Arg Val Ile Pro Asn Asn Gly Gly Thr Ser Tyr Asn Gln Lys Phe
    50                  55                  60
Lys Gly Lys Ala Ile Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Glu Gly Ile Tyr Trp Trp Gly His Gly Thr Thr Leu Thr Val
            100                 105                 110
Ser Ser
```

<210> SEQ ID NO 11
<211> LENGTH: 112
<212> TYPE: PRT
<213> ORGANISM: Mus musculus

```
<400> SEQUENCE: 11

Asp Val Val Thr Gln Thr Pro Leu Ser Leu Pro Val Ser Leu Gly
1               5                   10                  15

Ala Gln Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Gln
            100                 105                 110

<210> SEQ ID NO 12
<211> LENGTH: 112
<212> TYPE: PRT
<213> ORGANISM: Mus musculus

<400> SEQUENCE: 12

Asp Ile Gln Leu Gln Gln Ser Gly Pro Gly Leu Val Lys Pro Ser Gln
1               5                   10                  15

Ser Leu Ser Leu Thr Cys Ser Val Thr Gly Tyr Ser Ile Thr Thr Asn
            20                  25                  30

Tyr Asn Trp Asn Trp Ile Arg Gln Phe Pro Gly Asn Lys Leu Glu Trp
        35                  40                  45

Met Gly Tyr Ile Arg Tyr Asp Gly Thr Ser Glu Tyr Thr Pro Ser Leu
    50                  55                  60

Lys Asn Arg Val Ser Ile Thr Arg Asp Thr Ser Met Asn Gln Phe Phe
65                  70                  75                  80

Leu Arg Leu Thr Ser Val Thr Pro Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110

<210> SEQ ID NO 13
<211> LENGTH: 112
<212> TYPE: PRT
<213> ORGANISM: Mus musculus

<400> SEQUENCE: 13

Asp Ala Val Met Thr Gln Asn Pro Leu Ser Leu Pro Val Ser Leu Gly
1               5                   10                  15

Asp Glu Ala Ser Ile Ser Cys Arg Ser Ser Gln Ser Leu Glu Asn Ser
            20                  25                  30

Asn Gly Asn Thr Phe Leu Asn Trp Phe Phe Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Leu Glu Ile Lys
            100                 105                 110
```

<210> SEQ ID NO 14
<211> LENGTH: 113
<212> TYPE: PRT
<213> ORGANISM: Mus musculus

<400> SEQUENCE: 14

```
Gln Val Lys Leu Glu Glu Ser Gly Pro Gly Leu Val Ala Pro Ser Gln
 1               5                  10                  15

Ser Leu Ser Ile Thr Cys Thr Val Ser Gly Phe Ser Leu Ser Arg Tyr
             20                  25                  30

Ser Val Tyr Trp Val Arg Gln Pro Pro Gly Lys Gly Leu Glu Trp Leu
         35                  40                  45

Gly Met Met Trp Gly Gly Ser Thr Asp Tyr Asn Ser Ala Leu Lys
     50                  55                  60

Ser Arg Leu Ser Ile Ser Lys Asp Thr Ser Lys Ser Gln Val Phe Leu
65                  70                  75                  80

Lys Met Asn Ser Leu Gln Thr Asp Asp Thr Ala Met Tyr Tyr Cys Val
                 85                  90                  95

Arg Thr Asp Gly Asp Tyr Trp Gly Gln Gly Thr Ser Val Thr Val Ser
            100                 105                 110

Ser
```

<210> SEQ ID NO 15
<211> LENGTH: 112
<212> TYPE: PRT
<213> ORGANISM: Mus musculus

<400> SEQUENCE: 15

```
Glu Leu Gln Leu Thr Gln Ser Pro Leu Ser Leu Pro Val Ser Leu Gly
 1               5                  10                  15

Asp Gln Ala Ser Ile Ser Cys Arg Ser Ser Gln Ser Leu Val Asn Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110
```

<210> SEQ ID NO 16
<211> LENGTH: 7
<212> TYPE: PRT
<213> ORGANISM: Mus musculus

<400> SEQUENCE: 16

```
Tyr Ser Phe Thr Gly Tyr Tyr
 1               5
```

<210> SEQ ID NO 17
<211> LENGTH: 6
<212> TYPE: PRT
<213> ORGANISM: Mus musculus

<400> SEQUENCE: 17

```
Ile Pro Asn Asn Gly Gly
1               5

<210> SEQ ID NO 18
<211> LENGTH: 5
<212> TYPE: PRT
<213> ORGANISM: Mus musculus

<400> SEQUENCE: 18

Glu Gly Ile Tyr Trp
1               5

<210> SEQ ID NO 19
<211> LENGTH: 11
<212> TYPE: PRT
<213> ORGANISM: Mus musculus

<400> SEQUENCE: 19

Gln Ser Leu Val His Ser Asn Gly Asn Thr Phe
1               5                   10

<210> SEQ ID NO 20
<211> LENGTH: 7
<212> TYPE: PRT
<213> ORGANISM: Mus musculus

<400> SEQUENCE: 20

Thr Val Ser Asn Arg Phe Ser
1               5

<210> SEQ ID NO 21
<211> LENGTH: 7
<212> TYPE: PRT
<213> ORGANISM: Mus musculus

<400> SEQUENCE: 21

Thr Thr His Val Pro Trp Thr
1               5

<210> SEQ ID NO 22
<211> LENGTH: 8
<212> TYPE: PRT
<213> ORGANISM: Mus musculus

<400> SEQUENCE: 22

Tyr Ser Ile Thr Thr Asn Tyr Asn
1               5

<210> SEQ ID NO 23
<211> LENGTH: 5
<212> TYPE: PRT
<213> ORGANISM: Mus musculus

<400> SEQUENCE: 23

Arg Tyr Asp Gly Thr
1               5

<210> SEQ ID NO 24
<211> LENGTH: 3
<212> TYPE: PRT
<213> ORGANISM: Mus musculus

<400> SEQUENCE: 24

Leu Asp Tyr
1
```

```
<210> SEQ ID NO 25
<211> LENGTH: 11
<212> TYPE: PRT
<213> ORGANISM: Mus musculus

<400> SEQUENCE: 25

Gln Ser Leu Glu Asn Ser Asn Gly Asn Thr Phe
1               5                   10

<210> SEQ ID NO 26
<211> LENGTH: 7
<212> TYPE: PRT
<213> ORGANISM: Mus musculus

<400> SEQUENCE: 26

Arg Val Ser Asn Arg Phe Ser
1               5

<210> SEQ ID NO 27
<211> LENGTH: 7
<212> TYPE: PRT
<213> ORGANISM: Mus musculus

<400> SEQUENCE: 27

Val Thr His Val Pro Tyr Thr
1               5

<210> SEQ ID NO 28
<211> LENGTH: 9
<212> TYPE: PRT
<213> ORGANISM: Mus musculus

<400> SEQUENCE: 28

Phe Ser Leu Ser Arg Tyr Ser Val Tyr
1               5

<210> SEQ ID NO 29
<211> LENGTH: 3
<212> TYPE: PRT
<213> ORGANISM: Mus musculus

<400> SEQUENCE: 29

Gly Gly Ser
1

<210> SEQ ID NO 30
<211> LENGTH: 5
<212> TYPE: PRT
<213> ORGANISM: Mus musculus

<400> SEQUENCE: 30

Thr Asp Gly Asp Tyr
1               5

<210> SEQ ID NO 31
<211> LENGTH: 11
<212> TYPE: PRT
<213> ORGANISM: Mus musculus

<400> SEQUENCE: 31

Gln Ser Leu Val Asn Ser Asn Gly Asn Thr Tyr
1               5                   10

<210> SEQ ID NO 32
<211> LENGTH: 7
```

```
<212> TYPE: PRT
<213> ORGANISM: Mus musculus

<400> SEQUENCE: 32

Lys Val Ser Asn Arg Phe Ser
1               5

<210> SEQ ID NO 33
<211> LENGTH: 7
<212> TYPE: PRT
<213> ORGANISM: Mus musculus

<400> SEQUENCE: 33

Ser Thr His Val Pro Trp Thr
1               5

<210> SEQ ID NO 34
<211> LENGTH: 114
<212> TYPE: PRT
<213> ORGANISM: Artificial Sequence
<220> FEATURE:
<223> OTHER INFORMATION: S2C6 VH (H1)

<400> SEQUENCE: 34

Gln Val Gln Leu Val Gln Ser Gly Ala Glu Val Lys Pro Gly Ala
1               5                   10                  15

Ser Val Lys Val Ser Cys Lys Ala Ser Gly Tyr Ser Phe Thr Gly Tyr
                20                  25                  30

Tyr Ile His Trp Val Arg Gln Ala Pro Gly Gln Ser Leu Glu Trp Met
            35                  40                  45

Gly Arg Val Ile Pro Asn Asn Gly Gly Thr Tyr Asn Gln Lys Phe
50                  55                  60

Gln Gly Arg Val Thr Ile Ser Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Tyr Trp Trp Gly His Gly Thr Leu Val Thr Val
                100                 105                 110

Ser Ser

<210> SEQ ID NO 35
<211> LENGTH: 114
<212> TYPE: PRT
<213> ORGANISM: Artificial Sequence
<220> FEATURE:
<223> OTHER INFORMATION: S2C6 VH (H2)

<400> SEQUENCE: 35

Glu Val Gln Leu Val Gln Ser Gly Ala Glu Val Lys Pro Gly Glu
1               5                   10                  15

Ser Leu Lys Ile Ser Cys Lys Ala Ser Gly Tyr Ser Phe Thr Gly Tyr
                20                  25                  30

Tyr Ile His Trp Val Arg Gln Ala Pro Gly Lys Ser Leu Glu Trp Met
            35                  40                  45

Gly Arg Val Ile Pro Asn Asn Gly Gly Thr Tyr Asn Pro Ser Leu
50                  55                  60

Lys Ser Arg Val Thr Ile Ser Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

-continued

Ala Arg Glu Gly Ile Tyr Trp Trp Gly His Gly Thr Leu Val Thr Val
            100                 105                 110

Ser Ser

<210> SEQ ID NO 36
<211> LENGTH: 114
<212> TYPE: PRT
<213> ORGANISM: Artificial Sequence
<220> FEATURE:
<223> OTHER INFORMATION: S2C6 VH (H3)

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Lys Ser Leu Glu Trp Met
        35                  40                  45

Gly Arg Val Ile Pro Asn Asn Gly Gly Thr Ser Tyr Asn Pro Ser Leu
    50                  55                  60

Lys Ser Arg Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Ile Tyr Trp Trp Gly His Gly Thr Leu Val Thr Val
            100                 105                 110

Ser Ser

<210> SEQ ID NO 37
<211> LENGTH: 114
<212> TYPE: PRT
<213> ORGANISM: Artificial Sequence
<220> FEATURE:
<223> OTHER INFORMATION: S2C6 VH (H4)

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Ser Leu Glu Trp Val
        35                  40                  45

Ser Arg Val Ile Pro Asn Asn Gly Gly Thr Ser Tyr Asn Pro Ser Leu
    50                  55                  60

Lys Ser Arg Val Thr Ile Ser Val Asp Lys Ser Ile Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Gly Ile Tyr Trp Trp Gly His Gly Thr Leu Val Thr Val
            100                 105                 110

Ser Ser

<210> SEQ ID NO 38
<211> LENGTH: 112
<212> TYPE: PRT
<213> ORGANISM: Artificial Sequence
<220> FEATURE:
<223> OTHER INFORMATION: S2C6 VL (L1)

<400> SEQUENCE: 38

```
Asp Val Val Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Phe Cys Ser Gln Thr
            85                  90                  95

Thr His Val Pro Trp Thr Phe Gly Gly Gly Thr Lys Leu Glu Ile Lys
                100                 105                 110
```

<210> SEQ ID NO 39
<211> LENGTH: 112
<212> TYPE: PRT
<213> ORGANISM: Artificial Sequence
<220> FEATURE:
<223> OTHER INFORMATION: S2C6 VL (L2)

<400> SEQUENCE: 39

```
Asp Val Val Thr Gln Ser Pro Ala Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gly Asn Thr Phe Leu His Trp Tyr Gln Gln Lys Pro Asp Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Thr Ile
65              70                  75                  80

Ser Arg Leu Glu Pro Glu Asp Phe Ala Val Tyr Phe Cys Ser Gln Thr
            85                  90                  95

Thr His Val Pro Trp Thr Phe Gly Gly Gly Thr Lys Leu Glu Ile Lys
                100                 105                 110
```

<210> SEQ ID NO 40
<211> LENGTH: 112
<212> TYPE: PRT
<213> ORGANISM: Artificial Sequence
<220> FEATURE:
<223> OTHER INFORMATION: S2C6 VL (L3)

<400> SEQUENCE: 40

```
Asp Val Val Val Thr Gln Ser Pro Asp Ser Leu Ala Val Ser Leu Gly
1               5                   10                  15

Glu Arg Ala Thr Ile Asn Cys Lys Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Thr Ile
65              70                  75                  80

Ser Ser Leu Gln Ala Glu Asp Val Gly Val Tyr Phe Cys Ser Gln Thr
            85                  90                  95
```

```
Thr His Val Pro Trp Thr Phe Gly Gly Gly Thr Lys Leu Glu Ile Lys
        100                 105                 110
```